(12) United States Patent
Mackenzie et al.

(10) Patent No.: US 10,364,438 B1
(45) Date of Patent: *Jul. 30, 2019

(54) METHODS AND COMPOSITIONS FOR OBTAINING USEFUL PLANT TRAITS

(71) Applicant: NUtech Ventures, Lincoln, NE (US)

(72) Inventors: Sally A. Mackenzie, Lincoln, NE (US); Kamaldeep Virdi, Lincoln, NE (US)

(73) Assignee: NUTECH VENTURES, Lincoln, NE (US)

( * ) Notice: Subject to any disclaimer, the term of this patent is extended or adjusted under 35 U.S.C. 154(b) by 672 days.

This patent is subject to a terminal disclaimer.

(21) Appl. No.: 14/688,760

(22) Filed: Apr. 16, 2015

Related U.S. Application Data

(60) Provisional application No. 61/980,096, filed on Apr. 16, 2014.

(51) Int. Cl.
*C12N 15/82* (2006.01)

(52) U.S. Cl.
CPC .................. *C12N 15/8269* (2013.01)

(58) Field of Classification Search
None
See application file for complete search history.

(56) References Cited

U.S. PATENT DOCUMENTS

| | | | |
|---|---|---|---|
| 9,476,040 B2 | 10/2016 | Mackenzie et al. | |
| 9,708,672 B2 | 7/2017 | Mackenzie et al. | |
| 10,058,044 B2 | 8/2018 | Mackenzie et al. | |
| 2002/0010953 A1 | 1/2002 | Vliet | |
| 2004/0210962 A1* | 10/2004 | Mackenzie ............ | C07H 21/04 800/278 |
| 2006/0248613 A1 | 11/2006 | MacKenzie et al. | |
| 2006/0248614 A1 | 11/2006 | MacKenzie et al. | |
| 2012/0284814 A1* | 11/2012 | Mackenzie ............... | A01H 1/04 800/260 |
| 2014/0157452 A1 | 6/2014 | Mackenzie et al. | |
| 2015/0052630 A1 | 2/2015 | Mackenzie et al. | |
| 2015/0113679 A1 | 4/2015 | Mackenzie et al. | |
| 2015/0189842 A1 | 7/2015 | Mackenzie et al. | |
| 2017/0009308 A1 | 1/2017 | Mackenzie et al. | |

FOREIGN PATENT DOCUMENTS

| | | |
|---|---|---|
| WO | 2005/118805 A1 | 12/2005 |
| WO | 2007/033436 A1 | 3/2007 |
| WO | 2012/151254 A1 | 11/2012 |

OTHER PUBLICATIONS

Morrison et al. Current opinion in chemical biology 5.3 (2001): 302-307. (Year: 2001).*
Abdelnoor, R. V. et al., "Substoichiometric shifting in the plant mitochondrial genome is influenced by a gene homologous to MutS", Proc. Natl. Acad. Sci. U S A, May 13, 2003, 100(10):5968-73, Epub May 1, 2003.
Abdelnoor, R. V. et al., "Mitochondrial genome dynamics in plants and animals: convergent gene fusions of a MutS homologue", J. Mol. Evol. Aug. 2006, 63(2):165-73, Epub Jul. 7, 2006.
Arrieta-Montiel, M. P. et al., "Diversity of the Arabidopsis mitochondrial genome occurs via nuclear-controlled recombination activity", Genetics. Dec. 2009, 183(4):1261-8, doi: 10.1534/genetics.109.108514, Epub Oct. 12, 2009 (Abstract Only).
Davila, J. I. et al., "Double-strand break repair processes drive evolution of the mitochondrial genome in *Arabidopsis*", BMC Biol., Sep. 27, 2011, 9:64, doi: 10.1186/1741-7007-9-64.
Sandhu, A. P. et al., "Transgenic induction of mitochondrial rearrangements for cytoplasmic male sterility in crop plants", Proc. Natl. Acad. Sci. U S A, Feb. 6, 2007, 104(6):1766-70, Epub Jan. 29, 2007.
Shedge, V. et al., "Plant mitochondrial recombination surveillance requires unusual RecA and MutS homologs", Plant Cell., Apr. 2007, 19(4):1251-64, Epub Apr. 27, 2007.
Shedge, V. et al., "Extensive rearrangement of the *Arabidopsis* mitochondrial genome elicits cellular conditions for thermotolerance", Plant Physiol., Apr. 2010, 52(4):1960-70, doi: 10.1104/pp. 109.152827, Epub Feb. 5, 2010. (Abstract Only).
Sun, P. et al., "Utility of in vitro culture to the study of plant mitochondrial genome configuration and its dynamic features", Theor. Appl. Genet., Aug. 2012, 25(3):449-54, doi: 10.1007/s00122-012-1844-4, Epub Mar. 18, 2012.
Virdi, K. S. et al., "*Arabidopsis* MSH1 mutation alters the epigenome and produces heritable changes in plant growth", Nat. Commun., Feb. 27, 2015, 6386, doi: 10.1038/ncomms7386.
Xu, Y. Z. et al., "The chloroplast triggers developmental reprogramming when mutS HOMOLOG1 is suppressed in plants", Plant Physiol., Jun. 2012, 59(2):710-20, doi: 10.1104/pp. 112.196055, Epub Apr. 9, 2012.
Xu, Y. Z. et al., "MutS HOMOLOG1 is a nucleoid protein that alters mitochondrial and plastid properties and plant response to high light", Plant Cell., Sep. 2011, 23(9):3428-41, doi: 10.1105/tpc.111. 089136, Epub Sep. 20, 2011.

(Continued)

*Primary Examiner* — Mykola V. Kovalenko
*Assistant Examiner* — Charles Logsdon
(74) *Attorney, Agent, or Firm* — Thompson Coburn LLP; Charles P. Romano

(57) ABSTRACT

The present disclosure provides methods for obtaining plants that exhibit useful traits or that are useful for plant breeding by suppression of plastidic MSH1 in the presence of mitochondrial-targeted MSH1 in plants. Methods for identifying genetic loci that provide for useful traits in plants and plants produced with those loci are also provided. In addition, plants that exhibit the useful traits, parts of the plants including seeds, and products of the plants are provided as well as methods of using the plants. Recombinant DNA vectors and transgenic plants comprising those vectors that provide for suppression of plastidic MSH1 in the presence of mitochondrial-targeted MSH1 are also provided.

3 Claims, 6 Drawing Sheets
(4 of 6 Drawing Sheet(s) Filed in Color)
Specification includes a Sequence Listing.

(56) References Cited

OTHER PUBLICATIONS

Raju et al., "An Epigenetic Breeding System in Soybean for Increased Yield and Stability," Plant Biotechnology Journal, Mar. 2018, 37 pages.
Shag et al., "Stress-Responsive Pathways and Small RNA Changes Distinguish Variable Developmental Phenotypes Caused by MSH1 Loss," BMC Plant Biology, 2017, 14 pages, vol. 17, Issue 47.
Shao et al., "Ws-2 Introgression in a Proportion of *Arabidopsis thaliana* Col-0 Stock Seed Produces Specific Phenotypes and Highlights the Importance of Routine Genetic Verification", The Plant Cell, Mar. 2016, pp. 603-605, vol. 28.
Virdi et al., "*Arabidopsis* MSH1 Mutation Alters the Epigenome and Produces Heritable Changes in Plant Growth", Nature Communications, Feb. 27, 2015, 23 pages including Supplemental Figures_2015b.
Accession No. NP_565131 dated Jan. 22, 2014.
Arrieta-Montiel et al., "Diversity of the *Arabidopsis* Mitochondrial Genome Occurs via Nuclear-Controlled Recombination Activitiy", Genetics, 2009, pp. 1261-1268, vol. 183.
Becker et al., "Spontaneous epigenetic variation in the *Arabidopsis thaliana* methylome" Nature, 2011, vol. 480, pp. 245-249.
Boyko et al., "Transgenerational Adaptation of *Arabidopsis* to Stress Requires DNA Methylation and the Function of Dicer-Like Proteins", Public Library in Science One, Mar. 2010, pp. 1-12, vol. 5, Issue 3, e9514.
Dahlgren et al., "Analysis of siRNA Specificity on Targets with Double-Nucleotide Mismatches", Nucleic Acids Research, 2008, pp. 1-7, vol. 36 No. 9.
Du et al., "A Systematic Analysis of the Silencing Effects of an Active siRNA at all Single-Nucleotide Mismatched Target Sites", Nucleic Acids Research, 2005, pp. 1671-1677, vol. 33, No. 5.
European Search Report and Written Opinion dated Feb. 11, 2015 issued in EP Patent Application No. EP 14 18 6459.
Galloway et al., "Transgenerational Plasticity is Adaptive in the Wild", Science, Nov. 16, 2007, pp. 1134-1136, vol. 318, No. 5853.
Gao et al., "Analysis of the Leaf Methylomes of Parents and Their Hybrids Provides New Insight Into Hybrid Vigor in Populus Deltoides", BMC Genetics, 2014, 17 pages, vol. 15, Suppl. 1, No. S8.
Giannelos et al., "Tobacco Seed Oil as an Alternative Diesel Fuel: Physical and Chemical Properties", Industrial Crops and Products, Jul. 2002, pp. 1-9, vol. 16 Issue 1.
Greaves et al., "Inheritance of Trans Chromosomal Methylation Patterns from *Arabidopsis* F1 Hybrids", Proceedings of the National Academy of Sciences, Feb. 4, 2014, pp. 2017-2022, vol. 111, No. 5.
Groszmann et al. "Epigenetics in plants-vernalisation and hybrid vigour", Biochimica et Biophysica Acta, 2011, 1809, pp. 427-437.
Groszmann et al., "Intraspecific *Arabidopsis* Hybrids Show Different Patterns of Heterosis Despite the Close Relatedness of the Parental Genomes", Plant Physiology, Sep. 2014, pp. 265-280, vol. 166.
Groszmann et al., "The Role of Epigenetics in Hybrid Vigour", Trends in Genetics, Dec. 2013, pp. 684-690, vol. 29 No. 12.
Grouneva et al., "Phylogenetic viewpoints on regulation of light harvesting and electron transport in eukaryotic photosynthetic organisms", Planta, 2013, vol. 237, pp. 399-412.
Hauben et al. "Energy use efficiency is characterized by an epigenetic component that can be directed through artificial selection to increase yield", PNAS, 2009, vol. 106, No. 47, pp. 20109-20114.
Ifuku et al., "Molecular Functions of Oxygen-Evolving Complex Family Proteins in Photosynthetic Electron Flow", Journal of Integrative Plant Biology, Aug. 2010, pp. 723-734, vol. 52 No. 8.
Johannes et al., "Assessing the Impact of Transgenerational Epigenetic Variation on Complex Traits", Plos Genetics, 2009, vol. 5, Issue 6, e1000530.
Kimura et al., "Identification of *Arabidopsis* Genes Regulated by High Light-Stress Using cDNA Microarray", Photochemistry and Photobiology, Feb. 2003, pp. 226-233, vol. 77, No. 2.
Machczynska et al., "DNA Methylation Changes in Triticale Due to In Vitro Culture Plant Regeneration and Consecutive Reproduction", Plant Cell Tiss Organ Cult, Jun. 2014, pp. 289-299, vol. 119.
Molinier et al., "Transgeneration Memory of Stress in Plants", Nature, Aug. 31, 2006, pp. 1046-1049, vol. 442, Nature Publishing Group, 2006.
Nisar et al., "Inflorescence Stem Grafting Made Easy in *Arabidopsis*", Plant Methods, Dec. 19, 2012, pp. 50, vol. 8 No. 1.
Palauqui et al., "Systemic Acquired Silencing: Transgene-Specific Post-Transcriptional Silencing is Transmitted by Grafting from Silenced Stocks to Non-Silenced Scions," The EMBO Journal, 1997, pp. 4738-4745, vol. 16 No. 15.
Reinders et al., "Compromised Stability of DNA methylation and transposon immobilization in mosaic *Arabidopsis epigenomes*", Genes & Development, 2009, vol. 23, pp. 939-950.
Roux et al., "Genome-Wide Epigenetic Perturbation Jump-Starts Patterns of Heritable Variation Found in Nature", Genetics, 2011, vol. 188, pp. 1015-1017.
Santamaria et al., "MSH1-Induced Non-Genetic Variation Provides a Source of Phenotypic Diversity in Sorghum Bicolor", PLOS One, Oct. 2014, 8 pages, vol. 9, Issue 10, e108407.
Schmitz et al., "Transgenerational Epigenetic Instability is a Source of Novel Methylation Variants" Science, 2011, 334(6054): 369-373, 10 pages.
Shao et al., "Ws-2 Introgression in a Proportion of *Arabidopsis thaliana* Col-0 Stock Seed Produces Specific Phenotypes and Highlights the Importance of Routine Genetic Verification", Department of Agronomy and Horticulture, University of Nebraska, pp. 1-47, manuscript received for publication in The Plant Cell Jan. 26, 2016.
Shen et al., "Genome-Wide Analysis of DNA Methylation and Gene Expression Changes in Two *Arabidopsis* Ecotypes and Their Reciprocal Hybrids", The Plant Cell, Mar. 2012, pp. 875-892, vol. 24.
Stroud et al., "Plants regenerated from tissue culture contain stable epigenome changes in rice", eLife, 2013, No. 2: e00354, 14 pages.
Virdi et al., "*Arabidopsis* MSH1 Mutation Alters the Epigenome and Produces Heritable Changes in Plant Growth", Nature Communications, Feb. 27, 2015, 9 pages.
Virdi et al., "MSH1 is a Plant Organellar DNA Binding and Thylakoid Protein under Precise Spatial Regulation to Alter Development", Molecular Plant, 2015, pp. 1-16.
Wesley et al., "Construct Design for Efficient, Effective and High-Throughput Gene Silencing in Plants", The Plant Journal, Sep. 2001, pp. 581-590, vol. 27 Issue 6.
Yang et al., "MSH1-Derived Epigenetic Breeding Potential in Tomato", Plant Physiology Preview, Mar. 3, 2015, 34 pages.

* cited by examiner

| | Rosette diameter | | | | | Fresh biomass | | | | |
|---|---|---|---|---|---|---|---|---|---|---|
| | Mean (cm) | N | S.E.M. | S.D. | p-value | Mean (g) | N | S.E.M. | S.D. | p-value |
| AOX-MSH1 | 11.07 | 36 | 0.37 | 2.23 | < 0.001 | 8.86 | 10 | 0.47 | 1.33 | NS |
| SSU-MSH1 | 11.76 | 18 | 0.26 | 1.10 | < 0.001 | 10.00 | 10 | 0.55 | 1.56 | NS |
| Col-0 | 12.98 | 42 | 0.24 | 1.59 | - | 9.45 | 10 | 0.43 | 1.36 | - |
| F-2 (AOX-MSH1xCol-0) | 12.83 | 21 | 0.34 | 1.57 | NS | 15.07 | 10 | 0.66 | 2.07 | < 0.001 |
| F-22 (AOX-MSH1xCol-0) | 13.82 | 21 | 0.42 | 1.92 | < 0.10 | 14.62 | 10 | 0.92 | 2.24 | < 0.001 |
| F-28 (AOX-MSH1xCol-0) | 14.85 | 21 | 0.31 | 1.42 | < 0.001 | 13.27 | 10 | 0.70 | 1.99 | < 0.001 |
| F-26 (SSU-MSH1xCol-0) | 12.82 | 20 | 0.25 | 1.12 | NS | 10.57 | 10 | 0.66 | 1.74 | NS |
| F-29 (SSU-MSH1xCol-0) | 11.90 | 21 | 0.27 | 1.25 | < 0.001 | 10.50 | 10 | 0.45 | 1.19 | NS |

P-values are based on two-tailed Student t-tests compared to Col-0.
NS = not significant

Mitochondrial DNA recombination assay

Figure 5.

1      Wheat MSH1 RNAi (At4g02840 intron 2)
//HindIII/5'-Maize Ubiquitin promoter/intron/Wheat MSH1 Domain VI (SEQ ID NO: 3 reverse orientation)/ At4g02840 intron 2/ Wheat MSH1 Domain VI (SEQ ID NO: 3 forward orientation)/CaMV35S terminator/HindIII//

2      T-DNA of pCAMBIA1300-BAR binary plasmid
L Br < //T35S/BAR (SEQ ID NO: 6)/CaMV 35S Pro// MCS// >R Br

3      T-DNA of pCAMBIA1300-BAR//Arab-AOX1-Rice-MSH1
L Br < //T35S-BAR-CaMV 35S Pro// Rice MSH1 Promoter (SEQ ID NO: 4)-Arab AOX1-Rice MSH1-NOS3' (SEQ ID NO: 5)//SbfI HindIII/ >R Br

4      Rice MSH1 RNAi
//SbfI/ maize Ubiquitin promoter/intron/reverse rice MSH1 domain VI (SEQ ID NO: 7)/catalase intron/EcoRI/forward rice MSH1 domain VI (SEQ ID NO: 7)/ OCS 3' /HindIII//

5      T-DNA of pCAMBIA1300-BAR//Arab-AOX1-Rice-MSH1//Rice MSH1 RNAi
L Br < //T35S-BAR-CaMV 35S Pro// Rice MSH1 Promoter (SEQ ID NO: 4)-Arab AOX1-Rice MSH1-NOS3' (SEQ ID NO: 5)//SbfI/ maize Ubiquitin promoter/intron/reverse rice MSH1 domain VI (SEQ ID NO: 7)/catalase intron/EcoRI/forward rice MSH1 domain VI (SEQ ID NO: 7)/ OCS 3' /HindIII//>R Br

6      T-DNA of pCAMBIA1300-BAR//Rice-AOX1-Rice-MSH1
L Br < //T35S-BAR-CaMV 35S Pro// Rice MSH1 Promoter (SEQ ID NO: 4)-Rice AOX1-rice MSH1-NOS3'(SEQ ID NO: 8)//SbfI HindIII/ >R Br

7      T-DNA of pCAMBIA1300-BAR//Rice-AOX1-Rice-MSH1// Rice MSH1 RNAi
L Br < //T35S-BAR-CaMV 35S Pro// Rice MSH1 Promoter (SEQ ID NO: 4)-Rice AOX1-rice MSH1-NOS3'(SEQ ID NO: 8)//SbfI/ maize Ubiquitin promoter/intron/reverse rice MSH1 domain VI (SEQ ID NO: 7)/catalase intron/EcoRI/forward rice MSH1 domain VI (SEQ ID NO: 7)/ OCS 3' /HindIII//>R Br

8      Wheat MSH1 RNAi
//5' SbfI/maize Ubiquitin promoter/intron/reverse wheat MSH1 domain VI (SEQ ID NO: 3)/catalase intron/EcoRI/forward wheat MSH1 domain VI (SEQ ID NO: 3)/ OCS 3' /HindIII//

9      T-DNA of pCAMBIA1300-BAR//Arab-AOX1-Rice-MSH1//Wheat MSH1 RNAi
L Br < //T35S-BAR-CaMV 35S Pro// Rice MSH1 Promoter (SEQ ID NO: 4)-Arab AOX1-Rice MSH1-NOS3' (SEQ ID NO: 5)//5' SbfI/maize Ubiquitin promoter/intron/reverse wheat MSH1 domain VI (SEQ ID NO: 3)/catalase intron/EcoRI/forward wheat MSH1 domain VI (SEQ ID NO: 3)/ OCS 3' /HindIII//>
R Br

10     T-DNA of pCAMBIA1300-BAR//Rice-AOX1-Rice-MSH1//Wheat MSH1 RNAi
L Br < //T35S-BAR-CaMV 35S Pro// Rice MSH1 Promoter (SEQ ID NO: 4)-Rice AOX1-rice MSH1-NOS3'(SEQ ID NO: 8) //5' SbfI/maize Ubiquitin promoter/intron/reverse wheat MSH1 domain VI (SEQ ID NO: 3)/catalase intron/EcoRI/forward wheat MSH1 domain VI (SEQ ID NO: 3)/ OCS 3' /HindIII//>
R Br

Figure 6.

11   Maize MSH1 RNAi
//5' SbfI/maize Ubiquitin promoter/intron/reverse maize MSH1 domain VI (SEQ ID NO: 9)/catalase intron/EcoRI/forward maize MSH1 domain VI (SEQ ID NO: 9)/ OCS 3' /HindIII//>R Br

12   T-DNA of pCAMBIA1300-BAR//Arab-AOX1-Rice-MSH1// Maize MSH1 RNAi
L Br < //T35S-BAR-CaMV 35S Pro// Rice MSH1 Promoter (SEQ ID NO: 4)-Arab AOX1-Rice MSH1-NOS3' (SEQ ID NO: 5) //5' SbfI/maize Ubiquitin promoter/intron/reverse maize MSH1 domain VI (SEQ ID NO: 9)/catalase intron/EcoRI/forward maize MSH1 domain VI (SEQ ID NO: 9)/ OCS 3' /HindIII//>
R Br

13   T-DNA of pCAMBIA1300-BAR//Rice-AOX1-Rice-MSH1//Maize MSH1 RNAi
L Br < //T35S-BAR-CaMV 35S Pro// Rice MSH1 Promoter (SEQ ID NO: 4)-Rice AOX1-rice MSH1-NOS3' (SEQ ID NO: 8) //5' SbfI/maize Ubiquitin promoter/intron/reverse maize MSH1 domain VI (SEQ ID NO: 9)/catalase intron/EcoRI/forward maize MSH1 domain VI (SEQ ID NO: 9)/ OCS 3' /HindIII//>
R Br

14   T-DNA of pCAMBIA1300-BAR//Arab PRO-Arab-AOX1-Soy-MSH1
L Br < //T35S-BAR-CaMV 35S Pro//Arabidopsis MSH1 Promoter-Arab AOX1-Soy-MSH1-NOS3' (SEQ ID NO: 10)/SbfI/HindIII// >R Br

15   Soy MSH1 RNAi
// SbfI/ CaMV 35S promoter/reverse Soy MSH1 domain VI (SEQ ID NO: 11)/catalase intron/EcoRI/forward Soy MSH1 domain VI (SEQ ID NO: 11)/Octapine Synthase 3' polyadenyation region/HindIII//

16   T-DNA of pCAMBIA1300-BAR//Arab PRO-Arab-AOX1-Soy-MSH1//Soy MSH1 RNAi
L Br < //T35S-BAR-CaMV 35S Pro//Arabidopsis MSH1 Promoter-Arab AOX1-Soy-MSH1-NOS3' (SEQ ID NO: 10) // SbfI/ CaMV 35S promoter/reverse Soy MSH1 domain VI (SEQ ID NO: 11)/catalase intron/EcoRI/forward Soy MSH1 domain VI (SEQ ID NO: 11)/Octapine Synthase 3' polyadenyation region/HindIII//>R Br

17   T-DNA of pCAMBIA2300 //Arab PRO-Arab-AOX1-Potato-MSH1
L Br < //T35S-BAR-CaMV 35S Pro//Arabidopsis MSH1 Promoter-Arab AOX1-Potato-MSH1-NOS3' (SEQ ID NO: 12)//SbfI/HindIII// >R Br

18   Tomato MSH1 RNAi
// SbfI/ CaMV 35S promoter/reverse Tomato MSH1 domain VI (SEQ ID NO: 13)/catalase intron/EcoRI/forward Tomato MSH1 domain VI (SEQ ID NO: 13)/Octapine Synthase 3' polyadenyation region/HindIII//

19   pCAMBIA2300 //Arab PRO-Arab-AOX1-Potato-MSH1//Tomato MSH1 RNAi
L Br < //T35S-BAR-CaMV 35S Pro//Arabidopsis MSH1 Promoter-Arab AOX1-Potato-MSH1-NOS3' (SEQ ID NO: 12) // SbfI/ CaMV 35S promoter/reverse Tomato MSH1 domain VI (SEQ ID NO: 13)/catalase intron/EcoRI/forward Tomato MSH1 domain VI (SEQ ID NO: 13)/Octapine Synthase 3' polyadenyation region/HindIII//>R Br

```
                        SEQUENCE LISTING

<160> NUMBER OF SEQ ID NOS: 28

<210> SEQ ID NO 1
<211> LENGTH: 1122
<212> TYPE: PRT
<213> ORGANISM: Triticum aestivum
<220> FEATURE:
<221> NAME/KEY: PEPTIDE
<222> LOCATION: (1)..(1122)
<220> FEATURE:
<221> NAME/KEY: PEPTIDE
<222> LOCATION: (1)..(1122)
<223> OTHER INFORMATION: Triticum_aestivum partial MSH1 protein sequence

<400> SEQUENCE: 1

Ser Ser Val Val Ala Ala Ala Pro Arg Trp Leu Pro Val Ala Asp Ser
1               5                   10                  15

Ile Leu Arg Arg Arg Pro Arg Ser Pro Leu Pro Ile Leu Leu
            20                  25                  30

Phe Asn Arg Ser Trp Ser Lys Pro Lys Lys Val Ser Arg Ser Ile Ser
            35                  40                  45

Met Val Ser Ser Lys Val Asn Lys Gln Gly Asn Leu Cys Asn Glu Gly
    50                  55                  60

Met Leu Ser His Ile Met Trp Trp Lys Glu Arg Met Glu Ser Cys Arg
65                  70                  75                  80

Lys Pro Ser Ser Val Gln Leu Thr Gln Arg Leu Val Tyr Ser Asn Ile
                85                  90                  95

Leu Gly Leu Asp Pro Thr Leu Arg Asn Gly Ser Leu Lys Asp Gly Thr
            100                 105                 110

Leu Asn Met Glu Met Leu Gln Phe Lys Ser Lys Phe Pro Arg Glu Val
        115                 120                 125

Leu Leu Cys Arg Val Gly Asp Phe Tyr Glu Ala Ile Gly Phe Asp Ala
130                 135                 140

Cys Ile Leu Val Glu His Ala Gly Leu Asn Pro Phe Gly Gly Leu Arg
145                 150                 155                 160

Ser Asp Ser Ile Pro Lys Ala Gly Cys Pro Ile Met Asn Leu Arg Gln
                165                 170                 175

Thr Leu Asp Asp Leu Thr Arg Cys Gly Tyr Ser Val Cys Ile Val Glu
            180                 185                 190

Glu Ile Gln Gly Pro Thr Gln Ala Arg Ala Arg Lys Gly Arg Phe Ile
        195                 200                 205

Ser Gly His Ala His Pro Gly Ser Pro Tyr Val Phe Gly Leu Ala Glu
    210                 215                 220

Val Asp His Asp Leu Glu Phe Pro Asp Pro Met Pro Val Val Gly Ile
225                 230                 235                 240

Ser Arg Ser Ala Lys Gly Tyr Cys Leu Ile Ser Val Leu Glu Thr Met
                245                 250                 255

Lys Thr Tyr Ser Ala Glu Glu Gly Leu Thr Glu Glu Ala Ile Val Thr
            260                 265                 270
```

```
Lys Leu Arg Ile Cys Arg Tyr His Leu Tyr Leu His Ser Ser Leu
            275                 280                 285
Arg Asn Asn Ser Ser Gly Thr Ser Arg Trp Gly Glu Phe Gly Glu Gly
            290                 295                 300
Gly Leu Leu Trp Gly Glu Cys Asn Gly Lys Ser Phe Asp Trp Phe Asp
305                 310                 315                 320
Gly Ser Pro Ile Asp Glu Leu Leu Cys Lys Val Arg Glu Ile Tyr Gly
                325                 330                 335
Leu Asp Glu Lys Thr Ser Phe Arg Asn Val Thr Ile Ser Leu Glu Gly
            340                 345                 350
Arg Pro Gln Pro Leu Tyr Leu Gly Thr Ala Thr Gln Ile Gly Val Ile
            355                 360                 365
Pro Thr Glu Gly Ile Pro Ser Leu Pro Lys Met Leu Leu Pro Pro Asn
            370                 375                 380
Cys Ala Gly Leu Pro Ser Met Tyr Ile Arg Asp Leu Leu Leu Asn Pro
385                 390                 395                 400
Pro Ser Phe Asp Val Ala Ser Ala Ile Gln Glu Ala Cys Arg Leu Met
                405                 410                 415
Cys Ser Ile Thr Cys Ser Ile Pro Glu Phe Thr Cys Ile Pro Ser Ala
            420                 425                 430
Lys Leu Val Lys Leu Leu Glu Ser Lys Glu Val Asn His Ile Glu Phe
            435                 440                 445
Cys Arg Ile Lys Asn Val Leu Asp Glu Ile Met Leu Met Asn Gly Asn
            450                 455                 460
Thr Glu Leu Ser Ala Ile Gln Asn Lys Leu Leu Glu Pro Ala Ser Val
465                 470                 475                 480
Val Thr Gly Leu Lys Val Asp Ala Asp Ile Leu Ile Lys Glu Cys Arg
                485                 490                 495
Phe Ile Ser Lys Arg Ile Gly Glu Val Ile Ser Leu Ala Gly Glu Ser
            500                 505                 510
Asp Gln Ala Ile Thr Ser Ser Glu Tyr Ile Pro Lys Glu Phe Phe Asn
            515                 520                 525
Asp Met Glu Ser Phe Trp Lys Gly Arg Val Lys Arg Val His Ala Glu
            530                 535                 540
Glu Glu Phe Thr Asn Val Asp Val Ala Ala Gln Ala Leu Ser Thr Val
545                 550                 555                 560
Val Thr Glu Asp Phe Leu Pro Ile Ile Val Arg Val Lys Ala Val Met
                565                 570                 575
Ser Ser His Gly Ser Ser Lys Gly Glu Ile Ser Tyr Ala Lys Glu His
            580                 585                 590
Gly Ala Val Trp Phe Lys Gly Arg Arg Leu Ala Pro Thr Val Trp Ala
            595                 600                 605
Asn Thr Pro Gly Glu Glu Gln Ile Lys Gln Leu Lys Pro Ala Ile Asp
            610                 615                 620
Ser Lys Gly Arg Arg Val Gly Glu Glu Trp Phe Thr Thr Thr Lys Val
625                 630                 635                 640
Glu Asn Ala Leu Ala Arg Tyr His Glu Ala Cys Asp Asn Ala Lys Gly
                645                 650                 655
Lys Val Leu Glu Leu Leu Arg Gly Leu Ser Ser Glu Leu Gln Asp Lys
            660                 665                 670
Ile Asn Ile Leu Val Phe Cys Ser Thr Leu Leu Ile Ile Thr Lys Ala
            675                 680                 685
Leu Phe Gly His Val Ser Glu Gly Leu Arg Arg Gly Trp Val Leu Pro
```

-continued

```
            690             695             700
Ala Ile Tyr Pro Leu Ser Lys Asp Tyr Ser Thr Glu Glu Ser Ser
705                 710                 715                 720

Glu Met Asp Leu Leu Arg Leu Phe Pro Tyr Trp Leu Asp Thr Asn Gln
                725                 730                 735

Gly Asn Ala Ile Leu Asn Asp Val Asn Met Arg Ser Leu Phe Ile Leu
            740                 745                 750

Thr Gly Pro Asn Gly Gly Lys Ser Ser Met Leu Arg Ser Val Cys
                755                 760                 765

Ala Ala Ala Leu Leu Gly Val Cys Gly Leu Met Val Pro Ala Ala Ser
770                 775                 780

Ala Val Ile Pro His Phe Asp Ser Ile Met Leu His Met Lys Ala Tyr
785                 790                 795                 800

Asp Ser Pro Ala Asp Gly Lys Ser Ser Phe Gln Ile Glu Met Ser Glu
                805                 810                 815

Ile Arg Ser Leu Val Ser Arg Ala Thr Gly Arg Ser Leu Val Leu Ile
                820                 825                 830

Asp Glu Ile Cys Arg Gly Thr Glu Thr Ala Lys Gly Thr Cys Ile Ala
                835                 840                 845

Gly Ser Ile Ile Glu Arg Leu Asp Asp Val Gly Cys Leu Gly Ile Val
850                 855                 860

Ser Thr His Leu His Gly Ile Phe Asp Leu Pro Leu Ser Leu Asn Asn
865                 870                 875                 880

Thr Asp Phe Lys Ala Met Gly Thr Glu Val Val Asn Gly Cys Ile Gln
                885                 890                 895

Pro Thr Trp Arg Leu Met Asp Gly Ile Cys Arg Glu Ser Leu Ala Phe
                900                 905                 910

Gln Thr Ala Arg Lys Glu Gly Met Pro Asp Leu Ile Ile Lys Arg Ala
                915                 920                 925

Glu Glu Leu Tyr Leu Thr Met Ser Arg Ser Asn Lys Gln Thr Ser Ser
930                 935                 940

Thr Ala His His Gly Pro Ser Val Gly Tyr Ser Asn Val Asn Asp Leu
945                 950                 955                 960

Val Asp Met Pro Asp Gly Leu Gly Asn Phe Phe Glu Pro Ser Gly
                965                 970                 975

Ala Thr Gly Leu Leu Pro Lys Asp Val Glu Ser Ile Val Thr Thr Ile
                980                 985                 990

Cys Lys Asp Lys Leu Leu Asp Leu Tyr Asn Lys Arg Ser Ile Ser Glu
                995                 1000                1005

Leu Val Glu Val Val Cys Val Thr Val Gly Ala Arg Glu Gln Pro
    1010                1015                1020

Pro Pro Ser Thr Val Gly Arg Ser Ser Ile Tyr Ile Ile Arg
    1025                1030                1035

Arg Asp Asn Lys Leu Tyr Val Gly Gln Thr Asp Asp Leu Val Gly
    1040                1045                1050

Arg Leu Gly Ala His Arg Ser Lys Glu Gly Met Gln Asp Ala Thr
    1055                1060                1065

Ile Leu Tyr Ile Ile Val Pro Gly Lys Ser Val Ala Cys Gln Leu
    1070                1075                1080

Glu Thr Leu Leu Ile Asn Gln Leu Pro Thr Lys Gly Phe Lys Leu
    1085                1090                1095

Thr Asn Lys Ala Asp Gly Lys His Arg Asn Phe Gly Met Ser Val
    1100                1105                1110
```

```
                Thr Ser  Gly Glu Ala Met Ala  Ala His
                    1115                1120

<210> SEQ ID NO 2
<211> LENGTH: 3369
<212> TYPE: DNA
<213> ORGANISM: Triticum aestivum
<220> FEATURE:
<221> NAME/KEY: CDS
<222> LOCATION: (1)..(3369)
<223> OTHER INFORMATION: Triticum_aestivum partial MSH1 cDNA sequence

<400> SEQUENCE: 2 agc tcg gtc gtg gcc gcc gcg ccg cgg tgg ctc ccc gtt gcc gac tcg       48
Ser Ser Val Val Ala Ala Ala Pro Arg Trp Leu Pro Val Ala Asp Ser
1               5                   10                  15 atc ctc cgg cgc cgc cgc ccg cgc cgt tcc ccg ctc ccc atc ctg tta       96
Ile Leu Arg Arg Arg Arg Pro Arg Arg Ser Pro Leu Pro Ile Leu Leu
            20                  25                  30 ttc aac agg tct tgg tcc aaa cca aag aag gtt tca cgg agc att tcg      144
Phe Asn Arg Ser Trp Ser Lys Pro Lys Lys Val Ser Arg Ser Ile Ser
        35                  40                  45 atg gtg tct agt aag gtg aac aaa cag ggg aat ctc tgc aac gaa ggc      192
Met Val Ser Ser Lys Val Asn Lys Gln Gly Asn Leu Cys Asn Glu Gly
    50                  55                  60 atg ctg tct cat att atg tgg tgg aaa gag aga atg gag agc tgc agg      240
Met Leu Ser His Ile Met Trp Trp Lys Glu Arg Met Glu Ser Cys Arg
65                  70                  75                  80 aaa cca tca tct gtc caa ttg act cag aga ctc gtg tat tcg aac ata      288
Lys Pro Ser Ser Val Gln Leu Thr Gln Arg Leu Val Tyr Ser Asn Ile
                85                  90                  95 tta ggg ttg gat cca act tta agg aat gga agc tta aag gat gga acc      336
Leu Gly Leu Asp Pro Thr Leu Arg Asn Gly Ser Leu Lys Asp Gly Thr
            100                 105                 110 ctg aac atg gag atg tta caa ttc aaa tcg aag ttt cct cgc gag gtc      384
Leu Asn Met Glu Met Leu Gln Phe Lys Ser Lys Phe Pro Arg Glu Val
        115                 120                 125 cta ctt tgc aga gta gga gat ttc tac gaa gcc att gga ttt gat gcc      432
Leu Leu Cys Arg Val Gly Asp Phe Tyr Glu Ala Ile Gly Phe Asp Ala
    130                 135                 140 tgc att ctt gta gag cat gcg ggc tta aat cct ttt gga ggc ttg cgt      480
Cys Ile Leu Val Glu His Ala Gly Leu Asn Pro Phe Gly Gly Leu Arg
145                 150                 155                 160 tct gac agt att cca aaa gct gga tgt cca atc atg aat ttg cgg caa      528
Ser Asp Ser Ile Pro Lys Ala Gly Cys Pro Ile Met Asn Leu Arg Gln
                165                 170                 175 aca ttg gat gat ttg act cgg tgt ggt tat tct gtg tgc ata gtt gag      576
Thr Leu Asp Asp Leu Thr Arg Cys Gly Tyr Ser Val Cys Ile Val Glu
            180                 185                 190 gaa att caa ggc cca act caa gcc cgt gct cgg aaa ggt cga ttt att      624
Glu Ile Gln Gly Pro Thr Gln Ala Arg Ala Arg Lys Gly Arg Phe Ile
        195                 200                 205 tct ggc cat gca cat cct ggt agt cct tat gta ttt ggg ctt gct gaa      672
Ser Gly His Ala His Pro Gly Ser Pro Tyr Val Phe Gly Leu Ala Glu
    210                 215                 220 gta gac cat gat ctt gag ttt cct gac cca atg ccg gta gtt ggg att      720
Val Asp His Asp Leu Glu Phe Pro Asp Pro Met Pro Val Val Gly Ile
225                 230                 235                 240 tca cgc tcc gcg aaa ggc tat tgc ttg att tct gtg cta gaa acc atg      768
Ser Arg Ser Ala Lys Gly Tyr Cys Leu Ile Ser Val Leu Glu Thr Met
                245                 250                 255
```

-continued

```
aaa act tat tca gct gag gag ggc cta aca gag gaa gcc ata gtc act         816
Lys Thr Tyr Ser Ala Glu Glu Gly Leu Thr Glu Glu Ala Ile Val Thr
            260                 265                 270 aag ctg cgt ata tgc cgt tat cat cat tta tac ctt cac agt tct ctg         864
Lys Leu Arg Ile Cys Arg Tyr His His Leu Tyr Leu His Ser Ser Leu
        275                 280                 285 agg aat aat tct tca ggg aca tca cgc tgg gga gaa ttt ggc gag gga         912
Arg Asn Asn Ser Ser Gly Thr Ser Arg Trp Gly Glu Phe Gly Glu Gly
    290                 295                 300 ggg ctc ttg tgg gga gag tgc aac gga aag tct ttt gac tgg ttt gat         960
Gly Leu Leu Trp Gly Glu Cys Asn Gly Lys Ser Phe Asp Trp Phe Asp
305                 310                 315                 320 ggc tct cct att gac gaa ctt tta tgc aag gta agg gaa ata tat ggc        1008
Gly Ser Pro Ile Asp Glu Leu Leu Cys Lys Val Arg Glu Ile Tyr Gly
                325                 330                 335 ctg gat gag aaa act agt ttt cgc aac gtc act atc tcg ttg gaa ggg        1056
Leu Asp Glu Lys Thr Ser Phe Arg Asn Val Thr Ile Ser Leu Glu Gly
            340                 345                 350 agg cct caa cct tta tat ctt gga act gct act caa att gga gtg ata        1104
Arg Pro Gln Pro Leu Tyr Leu Gly Thr Ala Thr Gln Ile Gly Val Ile
        355                 360                 365 cca act gag ggg atc ccc agt tta cca aaa atg cta ctc cct cca aat        1152
Pro Thr Glu Gly Ile Pro Ser Leu Pro Lys Met Leu Leu Pro Pro Asn
    370                 375                 380 tgt gcc ggg ctt cca tca atg tat ata aga gat ctt ctt ctt aat cct        1200
Cys Ala Gly Leu Pro Ser Met Tyr Ile Arg Asp Leu Leu Leu Asn Pro
385                 390                 395                 400 cca tct ttt gat gtt gcc tct gca att caa gag gct tgc agg ctt atg        1248
Pro Ser Phe Asp Val Ala Ser Ala Ile Gln Glu Ala Cys Arg Leu Met
                405                 410                 415 tgc agc ata act tgt tcg att cca gaa ttt act tgc ata cca tcc gcg        1296
Cys Ser Ile Thr Cys Ser Ile Pro Glu Phe Thr Cys Ile Pro Ser Ala
            420                 425                 430 aag ctt gtg aaa tta ctt gag tca aaa gag gtt aat cac atc gaa ttt        1344
Lys Leu Val Lys Leu Leu Glu Ser Lys Glu Val Asn His Ile Glu Phe
        435                 440                 445 tgt aga ata aaa aat gtc ctt gac gag att atg tta atg aat gga aac        1392
Cys Arg Ile Lys Asn Val Leu Asp Glu Ile Met Leu Met Asn Gly Asn
    450                 455                 460 act gag ctt tca gct atc cag aac aaa ttg ctc gaa cct gct tcg gtg        1440
Thr Glu Leu Ser Ala Ile Gln Asn Lys Leu Leu Glu Pro Ala Ser Val
465                 470                 475                 480 gtt act ggg ttg aaa gtt gat gct gat ata cta att aaa gaa tgt aga        1488
Val Thr Gly Leu Lys Val Asp Ala Asp Ile Leu Ile Lys Glu Cys Arg
                485                 490                 495 ttt att tcc aaa cgt ata ggt gaa gtg ata tct tta gct ggc gaa agt        1536
Phe Ile Ser Lys Arg Ile Gly Glu Val Ile Ser Leu Ala Gly Glu Ser
            500                 505                 510 gat cag gca ata act tca tcg gaa tat att ccc aag gag ttc ttt aat        1584
Asp Gln Ala Ile Thr Ser Ser Glu Tyr Ile Pro Lys Glu Phe Phe Asn
        515                 520                 525 gat atg gag tca ttt tgg aag ggg cgt gtg aaa agg gtc cat gcc gaa        1632
Asp Met Glu Ser Phe Trp Lys Gly Arg Val Lys Arg Val His Ala Glu
    530                 535                 540 gaa gag ttc acc aat gtt gat gtc gct gct cag gca tta tca aca gtg        1680
Glu Glu Phe Thr Asn Val Asp Val Ala Ala Gln Ala Leu Ser Thr Val
545                 550                 555                 560 gtc act gaa gat ttt ctg cca att att gta aga gta aaa gcc gtg atg        1728
Val Thr Glu Asp Phe Leu Pro Ile Ile Val Arg Val Lys Ala Val Met
```

|  |  |  |  |  |  |  |  |  |  |  |  |  |  |  |  |  |
|---|---|---|---|---|---|---|---|---|---|---|---|---|---|---|---|---|
| | | | 565 | | | | | 570 | | | | | 575 | | | |
| tcc | tcg | cat | gga | agt | tct | aaa | ggg | gaa | atc | tct | tac | gca | aaa | gaa | cac | 1776 |
| Ser | Ser | His | Gly | Ser | Ser | Lys | Gly | Glu | Ile | Ser | Tyr | Ala | Lys | Glu | His | |
| | | | 580 | | | | | 585 | | | | | 590 | | | |
| ggg | gct | gtt | tgg | ttt | aaa | ggg | agg | cga | ctc | gca | cca | act | gtg | tgg | gcc | 1824 |
| Gly | Ala | Val | Trp | Phe | Lys | Gly | Arg | Arg | Leu | Ala | Pro | Thr | Val | Trp | Ala | |
| | | | 595 | | | | | 600 | | | | | 605 | | | |
| aac | aca | cct | ggt | gaa | gaa | cag | ata | aaa | caa | cta | aag | cct | gcg | att | gat | 1872 |
| Asn | Thr | Pro | Gly | Glu | Glu | Gln | Ile | Lys | Gln | Leu | Lys | Pro | Ala | Ile | Asp | |
| | | | 610 | | | | | 615 | | | | | 620 | | | |
| tca | aaa | ggt | aga | aga | gtt | ggg | gaa | gaa | tgg | ttt | aca | aca | acc | aaa | gtt | 1920 |
| Ser | Lys | Gly | Arg | Arg | Val | Gly | Glu | Glu | Trp | Phe | Thr | Thr | Thr | Lys | Val | |
| 625 | | | | | 630 | | | | | 635 | | | | | 640 | |
| gag | aat | gct | tta | gcc | agg | tat | cat | gaa | gct | tgt | gat | aat | gca | aaa | ggt | 1968 |
| Glu | Asn | Ala | Leu | Ala | Arg | Tyr | His | Glu | Ala | Cys | Asp | Asn | Ala | Lys | Gly | |
| | | | | 645 | | | | | 650 | | | | | 655 | | |
| aaa | gtt | cta | gag | cta | ttg | aga | ggt | ctt | tca | agc | gaa | tta | cag | gac | aag | 2016 |
| Lys | Val | Leu | Glu | Leu | Leu | Arg | Gly | Leu | Ser | Ser | Glu | Leu | Gln | Asp | Lys | |
| | | | 660 | | | | | 665 | | | | | 670 | | | |
| atc | aat | atc | ctt | gtc | ttc | tgc | tca | acg | ttg | ctc | atc | ata | aca | aaa | gca | 2064 |
| Ile | Asn | Ile | Leu | Val | Phe | Cys | Ser | Thr | Leu | Leu | Ile | Ile | Thr | Lys | Ala | |
| | | | 675 | | | | | 680 | | | | | 685 | | | |
| ctt | ttt | ggt | cat | gtt | agt | gag | ggt | cta | aga | agg | ggc | tgg | gtg | ctt | cct | 2112 |
| Leu | Phe | Gly | His | Val | Ser | Glu | Gly | Leu | Arg | Arg | Gly | Trp | Val | Leu | Pro | |
| | | | 690 | | | | | 695 | | | | | 700 | | | |
| gcc | ata | tat | ccc | tta | tct | aag | gat | tat | agt | acg | gaa | gaa | agc | tca | agc | 2160 |
| Ala | Ile | Tyr | Pro | Leu | Ser | Lys | Asp | Tyr | Ser | Thr | Glu | Glu | Ser | Ser | Ser | |
| 705 | | | | | 710 | | | | | 715 | | | | | 720 | |
| gaa | atg | gat | tta | tta | aga | ctc | ttt | cct | tac | tgg | ctt | gat | act | aat | caa | 2208 |
| Glu | Met | Asp | Leu | Leu | Arg | Leu | Phe | Pro | Tyr | Trp | Leu | Asp | Thr | Asn | Gln | |
| | | | | 725 | | | | | 730 | | | | | 735 | | |
| ggg | aat | gca | ata | ctg | aat | gat | gtc | aac | atg | cgt | tct | ttg | ttt | att | ttg | 2256 |
| Gly | Asn | Ala | Ile | Leu | Asn | Asp | Val | Asn | Met | Arg | Ser | Leu | Phe | Ile | Leu | |
| | | | 740 | | | | | 745 | | | | | 750 | | | |
| act | ggt | cca | aat | ggt | gga | ggt | aaa | tcc | agt | atg | ctg | cga | tca | gtc | tgc | 2304 |
| Thr | Gly | Pro | Asn | Gly | Gly | Gly | Lys | Ser | Ser | Met | Leu | Arg | Ser | Val | Cys | |
| | | | 755 | | | | | 760 | | | | | 765 | | | |
| gcg | gct | gca | ttg | ctt | gga | gta | tgt | ggc | ctg | atg | gtg | cca | gct | gct | tca | 2352 |
| Ala | Ala | Ala | Leu | Leu | Gly | Val | Cys | Gly | Leu | Met | Val | Pro | Ala | Ala | Ser | |
| 770 | | | | | 775 | | | | | 780 | | | | | | |
| gct | gtc | att | cca | cac | ttt | gat | tct | ata | atg | ctg | cat | atg | aag | gcc | tat | 2400 |
| Ala | Val | Ile | Pro | His | Phe | Asp | Ser | Ile | Met | Leu | His | Met | Lys | Ala | Tyr | |
| 785 | | | | | 790 | | | | | 795 | | | | | 800 | |
| gac | agt | cca | gct | gat | ggg | aaa | agt | tcg | ttt | cag | atc | gaa | atg | tca | gag | 2448 |
| Asp | Ser | Pro | Ala | Asp | Gly | Lys | Ser | Ser | Phe | Gln | Ile | Glu | Met | Ser | Glu | |
| | | | | 805 | | | | | 810 | | | | | 815 | | |
| ata | cga | tct | tta | gtt | agt | cga | gct | act | ggt | agg | agt | ctt | gtt | ctc | atc | 2496 |
| Ile | Arg | Ser | Leu | Val | Ser | Arg | Ala | Thr | Gly | Arg | Ser | Leu | Val | Leu | Ile | |
| | | | 820 | | | | | 825 | | | | | 830 | | | |
| gat | gaa | att | tgt | aga | ggc | aca | gaa | act | gca | aaa | gga | act | tgt | ata | gct | 2544 |
| Asp | Glu | Ile | Cys | Arg | Gly | Thr | Glu | Thr | Ala | Lys | Gly | Thr | Cys | Ile | Ala | |
| | | | 835 | | | | | 840 | | | | | 845 | | | |
| ggt | agc | atc | att | gaa | agg | ctg | gat | gac | gtt | ggc | tgc | ctg | ggc | atc | gta | 2592 |
| Gly | Ser | Ile | Ile | Glu | Arg | Leu | Asp | Asp | Val | Gly | Cys | Leu | Gly | Ile | Val | |
| 850 | | | | | 855 | | | | | 860 | | | | | | |
| tca | acc | cat | tta | cat | ggc | att | ttt | gac | ctt | cct | ctt | tca | ctc | aac | aat | 2640 |
| Ser | Thr | His | Leu | His | Gly | Ile | Phe | Asp | Leu | Pro | Leu | Ser | Leu | Asn | Asn | |
| 865 | | | | | 870 | | | | | 875 | | | | | 880 | |
| act | gat | ttc | aag | gct | atg | gga | aca | gaa | gtg | gtc | aat | ggg | tgc | att | cag | 2688 |

```
                Thr Asp Phe Lys Ala Met Gly Thr Glu Val Val Asn Gly Cys Ile Gln
                                885                 890                 895 cca aca tgg aga ctt atg gat ggc atc tgt aga gaa agc ctt gct ttt          2736
Pro Thr Trp Arg Leu Met Asp Gly Ile Cys Arg Glu Ser Leu Ala Phe
            900                 905                 910 caa aca gcc agg aag gaa ggt atg cct gac ttg ata att aaa aga gca          2784
Gln Thr Ala Arg Lys Glu Gly Met Pro Asp Leu Ile Ile Lys Arg Ala
            915                 920                 925 gag gag cta tat ttg acc atg agc aga agc aac aaa cag aca tca tca          2832
Glu Glu Leu Tyr Leu Thr Met Ser Arg Ser Asn Lys Gln Thr Ser Ser
        930                 935                 940 aca gcc cac cat ggg cct tcc gtt ggc tac tcc aat gta aat gac ttg          2880
Thr Ala His His Gly Pro Ser Val Gly Tyr Ser Asn Val Asn Asp Leu
945                 950                 955                 960 gtt gat atg cct gat ggt ctg gga aat ttc ttc gaa cct ccg tca ggt          2928
Val Asp Met Pro Asp Gly Leu Gly Asn Phe Phe Glu Pro Pro Ser Gly
                965                 970                 975 gct act gga ctg ctg cca aag gat gtc gag agc att gtt acc aca ata          2976
Ala Thr Gly Leu Leu Pro Lys Asp Val Glu Ser Ile Val Thr Thr Ile
            980                 985                 990 tgc aaa gat aaa ctg ttg gat ctc tac aac aag aga agc atc tca gaa          3024
Cys Lys Asp Lys Leu Leu Asp Leu Tyr Asn Lys Arg Ser Ile Ser Glu
        995                 1000                1005 ctg gtt gag gtg gtc tgc gtt act gta ggt gct agg gag caa ccg             3069
Leu Val Glu Val Val Cys Val Thr Val Gly Ala Arg Glu Gln Pro
    1010                1015                1020 cca cct tca act gtt ggg agg tcc agc atc tat atc atc atc aga             3114
Pro Pro Ser Thr Val Gly Arg Ser Ser Ile Tyr Ile Ile Ile Arg
    1025                1030                1035 cgt gac aac aag ctc tat gtt gga cag acg gat gat ctt gtg ggc             3159
Arg Asp Asn Lys Leu Tyr Val Gly Gln Thr Asp Asp Leu Val Gly
    1040                1045                1050 cgt ctt ggt gct cat aga tcg aag gaa ggt atg cag gat gcc aca             3204
Arg Leu Gly Ala His Arg Ser Lys Glu Gly Met Gln Asp Ala Thr
    1055                1060                1065 ata tta tac atc att gtt cct ggc aag agt gtt gcc tgc caa ctg             3249
Ile Leu Tyr Ile Ile Val Pro Gly Lys Ser Val Ala Cys Gln Leu
    1070                1075                1080 gag act ctt ctc ata aat cag cta ccc acg aaa ggt ttt aag ctc             3294
Glu Thr Leu Leu Ile Asn Gln Leu Pro Thr Lys Gly Phe Lys Leu
    1085                1090                1095 acc aac aag gca gat ggc aag cat cgg aac ttt ggt atg tct gta             3339
Thr Asn Lys Ala Asp Gly Lys His Arg Asn Phe Gly Met Ser Val
    1100                1105                1110 acc tct gga gaa gcc atg gct gca cac tga                                 3369
Thr Ser Gly Glu Ala Met Ala Ala His
    1115                1120

<210> SEQ ID NO 3
<211> LENGTH: 1122
<212> TYPE: PRT
<213> ORGANISM: Triticum aestivum

<400> SEQUENCE: 3

Ser Ser Val Val Ala Ala Ala Pro Arg Trp Leu Pro Val Ala Asp Ser
1               5                   10                  15

Ile Leu Arg Arg Arg Pro Arg Arg Ser Pro Leu Pro Ile Leu Leu
            20                  25                  30

Phe Asn Arg Ser Trp Ser Lys Pro Lys Lys Val Ser Arg Ser Ile Ser
        35                  40                  45
```

```
Met Val Ser Ser Lys Val Asn Lys Gln Gly Asn Leu Cys Asn Glu Gly
     50                  55                  60

Met Leu Ser His Ile Met Trp Trp Lys Glu Arg Met Glu Ser Cys Arg
 65                  70                  75                  80

Lys Pro Ser Ser Val Gln Leu Thr Gln Arg Leu Val Tyr Ser Asn Ile
                 85                  90                  95

Leu Gly Leu Asp Pro Thr Leu Arg Asn Gly Ser Leu Lys Asp Gly Thr
                100                 105                 110

Leu Asn Met Glu Met Leu Gln Phe Lys Ser Lys Phe Pro Arg Glu Val
            115                 120                 125

Leu Leu Cys Arg Val Gly Asp Phe Tyr Glu Ala Ile Gly Phe Asp Ala
    130                 135                 140

Cys Ile Leu Val Glu His Ala Gly Leu Asn Pro Phe Gly Gly Leu Arg
145                 150                 155                 160

Ser Asp Ser Ile Pro Lys Ala Gly Cys Pro Ile Met Asn Leu Arg Gln
                165                 170                 175

Thr Leu Asp Asp Leu Thr Arg Cys Gly Tyr Ser Val Cys Ile Val Glu
            180                 185                 190

Glu Ile Gln Gly Pro Thr Gln Ala Arg Ala Arg Lys Gly Arg Phe Ile
    195                 200                 205

Ser Gly His Ala His Pro Gly Ser Pro Tyr Val Phe Gly Leu Ala Glu
210                 215                 220

Val Asp His Asp Leu Glu Phe Pro Asp Pro Met Pro Val Val Gly Ile
225                 230                 235                 240

Ser Arg Ser Ala Lys Gly Tyr Cys Leu Ile Ser Val Leu Glu Thr Met
                245                 250                 255

Lys Thr Tyr Ser Ala Glu Glu Gly Leu Thr Glu Glu Ala Ile Val Thr
            260                 265                 270

Lys Leu Arg Ile Cys Arg Tyr His His Leu Tyr Leu His Ser Ser Leu
    275                 280                 285

Arg Asn Asn Ser Ser Gly Thr Ser Arg Trp Gly Glu Phe Gly Glu Gly
290                 295                 300

Gly Leu Leu Trp Gly Glu Cys Asn Gly Lys Ser Phe Asp Trp Phe Asp
305                 310                 315                 320

Gly Ser Pro Ile Asp Glu Leu Leu Cys Lys Val Arg Glu Ile Tyr Gly
                325                 330                 335

Leu Asp Glu Lys Thr Ser Phe Arg Asn Val Thr Ile Ser Leu Glu Gly
            340                 345                 350

Arg Pro Gln Pro Leu Tyr Leu Gly Thr Ala Thr Gln Ile Gly Val Ile
    355                 360                 365

Pro Thr Glu Gly Ile Pro Ser Leu Pro Lys Met Leu Leu Pro Pro Asn
370                 375                 380

Cys Ala Gly Leu Pro Ser Met Tyr Ile Arg Asp Leu Leu Asn Pro
385                 390                 395                 400

Pro Ser Phe Asp Val Ala Ser Ala Ile Gln Glu Ala Cys Arg Leu Met
                405                 410                 415

Cys Ser Ile Thr Cys Ser Ile Pro Glu Phe Thr Cys Ile Pro Ser Ala
            420                 425                 430

Lys Leu Val Lys Leu Leu Glu Ser Lys Glu Val Asn His Ile Glu Phe
    435                 440                 445

Cys Arg Ile Lys Asn Val Leu Asp Glu Ile Met Leu Met Asn Gly Asn
450                 455                 460
```

```
Thr Glu Leu Ser Ala Ile Gln Asn Lys Leu Leu Glu Pro Ala Ser Val
465                 470                 475                 480

Val Thr Gly Leu Lys Val Asp Ala Asp Ile Leu Ile Lys Glu Cys Arg
                485                 490                 495

Phe Ile Ser Lys Arg Ile Gly Glu Val Ile Ser Leu Ala Gly Glu Ser
                500                 505                 510

Asp Gln Ala Ile Thr Ser Ser Glu Tyr Ile Pro Lys Glu Phe Phe Asn
                515                 520                 525

Asp Met Glu Ser Phe Trp Lys Gly Arg Val Lys Arg Val His Ala Glu
            530                 535                 540

Glu Glu Phe Thr Asn Val Asp Val Ala Ala Gln Ala Leu Ser Thr Val
545                 550                 555                 560

Val Thr Glu Asp Phe Leu Pro Ile Ile Val Arg Val Lys Ala Val Met
                565                 570                 575

Ser Ser His Gly Ser Ser Lys Gly Glu Ile Ser Tyr Ala Lys Glu His
                580                 585                 590

Gly Ala Val Trp Phe Lys Gly Arg Arg Leu Ala Pro Thr Val Trp Ala
            595                 600                 605

Asn Thr Pro Gly Glu Glu Gln Ile Lys Gln Leu Lys Pro Ala Ile Asp
610                 615                 620

Ser Lys Gly Arg Arg Val Gly Glu Glu Trp Phe Thr Thr Thr Lys Val
625                 630                 635                 640

Glu Asn Ala Leu Ala Arg Tyr His Glu Ala Cys Asp Asn Ala Lys Gly
                645                 650                 655

Lys Val Leu Glu Leu Leu Arg Gly Leu Ser Ser Glu Leu Gln Asp Lys
                660                 665                 670

Ile Asn Ile Leu Val Phe Cys Ser Thr Leu Leu Ile Ile Thr Lys Ala
                675                 680                 685

Leu Phe Gly His Val Ser Glu Gly Leu Arg Arg Gly Trp Val Leu Pro
            690                 695                 700

Ala Ile Tyr Pro Leu Ser Lys Asp Tyr Ser Thr Glu Glu Ser Ser Ser
705                 710                 715                 720

Glu Met Asp Leu Leu Arg Leu Phe Pro Tyr Trp Leu Asp Thr Asn Gln
                725                 730                 735

Gly Asn Ala Ile Leu Asn Asp Val Asn Met Arg Ser Leu Phe Ile Leu
            740                 745                 750

Thr Gly Pro Asn Gly Gly Lys Ser Ser Met Leu Arg Ser Val Cys
                755                 760                 765

Ala Ala Ala Leu Leu Gly Val Cys Gly Leu Met Val Pro Ala Ala Ser
            770                 775                 780

Ala Val Ile Pro His Phe Asp Ser Ile Met Leu His Met Lys Ala Tyr
785                 790                 795                 800

Asp Ser Pro Ala Asp Gly Lys Ser Ser Phe Gln Ile Glu Met Ser Glu
                805                 810                 815

Ile Arg Ser Leu Val Ser Arg Ala Thr Gly Arg Ser Leu Val Leu Ile
            820                 825                 830

Asp Glu Ile Cys Arg Gly Thr Glu Thr Ala Lys Gly Thr Cys Ile Ala
            835                 840                 845

Gly Ser Ile Ile Glu Arg Leu Asp Asp Val Gly Cys Leu Gly Ile Val
            850                 855                 860

Ser Thr His Leu His Gly Ile Phe Asp Leu Pro Leu Ser Leu Asn Asn
865                 870                 875                 880

Thr Asp Phe Lys Ala Met Gly Thr Glu Val Val Asn Gly Cys Ile Gln
```

```
                        885                 890                 895
Pro Thr Trp Arg Leu Met Asp Gly Ile Cys Arg Glu Ser Leu Ala Phe
                    900                 905                 910

Gln Thr Ala Arg Lys Glu Gly Met Pro Asp Leu Ile Ile Lys Arg Ala
                915                 920                 925

Glu Glu Leu Tyr Leu Thr Met Ser Arg Ser Asn Lys Gln Thr Ser Ser
            930                 935                 940

Thr Ala His His Gly Pro Ser Val Gly Tyr Ser Asn Val Asn Asp Leu
945                 950                 955                 960

Val Asp Met Pro Asp Gly Leu Gly Asn Phe Phe Glu Pro Pro Ser Gly
                965                 970                 975

Ala Thr Gly Leu Leu Pro Lys Asp Val Glu Ser Ile Val Thr Thr Ile
            980                 985                 990

Cys Lys Asp Lys Leu Leu Asp Leu Tyr Asn Lys Arg Ser Ile Ser Glu
        995                 1000                1005

Leu Val Glu Val Val Cys Val  Thr Val Gly Ala Arg  Glu Gln Pro
    1010                1015                1020

Pro Pro Ser Thr Val Gly Arg  Ser Ser Ile Tyr Ile  Ile Ile Arg
    1025                1030                1035

Arg Asp Asn Lys Leu Tyr Val  Gly Gln Thr Asp Asp  Leu Val Gly
    1040                1045                1050

Arg Leu Gly Ala His Arg Ser  Lys Glu Gly Met Gln  Asp Ala Thr
    1055                1060                1065

Ile Leu Tyr Ile Ile Val Pro  Gly Lys Ser Val Ala  Cys Gln Leu
    1070                1075                1080

Glu Thr Leu Leu Ile Asn Gln  Leu Pro Thr Lys Gly  Phe Lys Leu
    1085                1090                1095

Thr Asn Lys Ala Asp Gly Lys  His Arg Asn Phe Gly  Met Ser Val
    1100                1105                1110

Thr Ser Gly Glu Ala Met Ala  Ala His
    1115                1120

<210> SEQ ID NO 4
<211> LENGTH: 327
<212> TYPE: DNA
<213> ORGANISM: Triticum aestivum
<220> FEATURE:
<221> NAME/KEY: CDS
<222> LOCATION: (1)..(327)
<223> OTHER INFORMATION: Domain VI of wheat MSH1
<220> FEATURE:
<221> NAME/KEY: exon
<222> LOCATION: (1)..(327)

<400> SEQUENCE: 4 agc atc tca gag ctg gtt gag gtg gtt tgt gtt act gta ggt gct agg      48
Ser Ile Ser Glu Leu Val Glu Val Val Cys Val Thr Val Gly Ala Arg
1               5                   10                  15 gag caa ccg cca cct tca act gtt ggc agg tcc agc atc tat atc att      96
Glu Gln Pro Pro Pro Ser Thr Val Gly Arg Ser Ser Ile Tyr Ile Ile
                20                  25                  30 atc aga cgt gac aac aag ctc tac gtc gga cag acg gat gat ctc atg     144
Ile Arg Arg Asp Asn Lys Leu Tyr Val Gly Gln Thr Asp Asp Leu Met
            35                  40                  45 ggc cgt ctt ggt gct cat aga tcc aag gaa ggt atg cag gat gcc aca     192
Gly Arg Leu Gly Ala His Arg Ser Lys Glu Gly Met Gln Asp Ala Thr
        50                  55                  60 ata tta tac atc atg gtt cct ggc aag agc att gca tgc caa ctg gag     240
```

```
Ile Leu Tyr Ile Met Val Pro Gly Lys Ser Ile Ala Cys Gln Leu Glu
 65                  70                  75                  80 act ctt ctc ata aat cag cta ccc tcg aaa ggt ttt aag ctc acg aac    288
Thr Leu Leu Ile Asn Gln Leu Pro Ser Lys Gly Phe Lys Leu Thr Asn
                 85                  90                  95 aag gca gat ggc aag cat cgg aac ttc gaa ggg cga att                327
Lys Ala Asp Gly Lys His Arg Asn Phe Glu Gly Arg Ile
            100                 105

<210> SEQ ID NO 5
<211> LENGTH: 109
<212> TYPE: PRT
<213> ORGANISM: Triticum aestivum

<400> SEQUENCE: 5

Ser Ile Ser Glu Leu Val Glu Val Val Cys Val Thr Val Gly Ala Arg
  1               5                  10                  15

Glu Gln Pro Pro Ser Thr Val Gly Arg Ser Ser Ile Tyr Ile Ile
             20                  25                  30

Ile Arg Arg Asp Asn Lys Leu Tyr Val Gly Gln Thr Asp Asp Leu Met
         35                  40                  45

Gly Arg Leu Gly Ala His Arg Ser Lys Glu Gly Met Gln Asp Ala Thr
     50                  55                  60

Ile Leu Tyr Ile Met Val Pro Gly Lys Ser Ile Ala Cys Gln Leu Glu
 65                  70                  75                  80

Thr Leu Leu Ile Asn Gln Leu Pro Ser Lys Gly Phe Lys Leu Thr Asn
                 85                  90                  95

Lys Ala Asp Gly Lys His Arg Asn Phe Glu Gly Arg Ile
            100                 105

<210> SEQ ID NO 6
<211> LENGTH: 2047
<212> TYPE: DNA
<213> ORGANISM: Oryza sativa
<220> FEATURE:
<221> NAME/KEY: promoter
<222> LOCATION: (1)..(2047)
<223> OTHER INFORMATION: Rice Msh1 promoter

<400> SEQUENCE: 6
agatctacgg ccagcttctt gcaatccatc ggcggtctcc ggctcctgca gcagcggagc      60
atgccgcggc gtgcgctgct cggcggcgaa caagccttct ccttccaccg ctccgggcac     120
cgaggtaagg tagccggcta gccgcccccc atattcttgt ttctgtgttg atcggagctc     180
gatggctggg gtgctctggg ctcgtcgtcg tcggtcgatc gtcatggctt gcttcgtttc     240
ttgcagctcg acctccatgg caaagataag gagtgaggtg ctgtcccgt tccgctccgt      300 gcggatgttc ttctacctcg cgttcatggc cagcgccggg ctcggggccc tcatcgcgct     360
cacgcagctc atcccggcgc tgtccagccc ggcgagggcg gccgccgcgg gggagacgct     420
caagggcctg ggcatcgacg tcgcggcggt ctccgtcttc gcgttcctct actggcgcga     480
gagcaaggcc aaggacgcgc aggtggcgaa gctcacgcgg gaggagaacc tgtccaggct     540
caggatccgc gccggcgagg gccgcccgcc cgtcccgctc ggcgagctga ggggcaccgc     600
gcggctcgtc atcgtcgccg gccccgcggc gttcgtcacc gagtcgttcc gccggagcaa     660
gccgttcttg aaggacctca tggagcgcgg cgtgcttgtc gtgcccttct cgacggacgg     720
caacgcgccg gacctgcagt cgacgaggc cgacgaggag gaggaggagg cggcggcggc     780
ggctgggaag atgaagcgga ggctctggca gctcactccg gtttacactt ctgaatgggc     840
```

```
caagtacgcg caaagccggg atcccatgaa tttagctgct taaatttctt cttcatgtca      900
atcgaaattc aaatgcaaat tagtatctca ttttcaaatc gattgctgct tcttgcagat      960
ggctagatga gcagaagaag ctagccaacg tgtcacctga ttcccccgtg tgagtatcaa     1020
aaactactct gaatttgtct gaaaatataa ctgaagtttc tgcagctgct gaactgaaac     1080
cgcatcactc ttgcaggtat ctctcgctcc ggctggacgg ccgcgtccgt ggcagcggcg     1140
tcgggtaccc gccgtggcaa gcgttcgtgg cgcagctgcc gccggtgaag gggatgtggt     1200
ccggcctcct tgatgggatg acgggaggg tgctttgaat atttgactga tacagaccgt      1260
gaaaacatta gttgattgga gaaaaaaaag gacggccggg ttcgatctat agcttatact     1320
agaacaagaa caggaagagt ttgatgattg ctttaacttc tgtggggttg attttgcttc     1380
ctgcatccca gcgacatcgc ccaagtgaat gtgatatgcc atgtgcccat gtacatgttg     1440
ttttgcagcc tacgtgactt gattattaac gagaatcctg tgtcaaagat cgcttttcc      1500 gtggtaggct tctccatttt atttattttt tgaatatata tacgaaccgt gacaaatctg     1560
atggaacact ggaccatggg ggtaatgata ctgtagtcgc ctggtctttt tatcaggcgc     1620
taaatgcaaa caatcagaca gcttaaacaa cctgaggttg ttcagccagc ccagaataca     1680
aaaagcccat ggaccgtgag cccgtgaaac catggcccac ccatcagtca cgtcacgtcg     1740
ggacgtgtgc gcactacccc gagaagcgcg cggccgtaag ccacaaccac aaccccacac     1800
cgcctcttgg ctgctcgcgc cctgacactt cccaaaaccc caaaccgccc atatctctct     1860
cctcttctcc gctcctcgct tcccccaaaa ccctcgcggt ggcggtgggc cgccggtctc     1920
attccgccgg cgtccacgga ggcggccgga gccaggcgct ccgcgggccg gggagccacc     1980
ggaaggctgg aaccctagcg gcggcgggtc tcctcccct ccccgcgcgc cgggcggcgc      2040
cctcgag                                                              2047

<210> SEQ ID NO 7
<211> LENGTH: 3707
<212> TYPE: DNA
<213> ORGANISM: Artificial Sequence
<220> FEATURE:
<223> OTHER INFORMATION: Synthetic gene for a rice MSH1 with an
      Arabidopsis AOX1 mitochondrial targeting sequence, designed with
      monocot codons and a NOS 3' polyadenylation region
<220> FEATURE:
<221> NAME/KEY: 5'UTR
<222> LOCATION: (1)..(9)
<220> FEATURE:
<221> NAME/KEY: CDS
<222> LOCATION: (10)..(201)
<223> OTHER INFORMATION: Arabidopsis AOX1 mitochondrial targeting signal
<220> FEATURE:
<221> NAME/KEY: CDS
<222> LOCATION: (202)..(3369)
<223> OTHER INFORMATION: synthetic rice MSH1 CDS lacking its native
      targeting signal
<220> FEATURE:
<221> NAME/KEY: polyA_site
<222> LOCATION: (3370)..(3707)
<223> OTHER INFORMATION: NOS 3' polyadenylation region

<400> SEQUENCE: 7 gtcgacacc atg atg atc acc cgc ggc gga gcc aag gcg gcg aag agc ctg     51
           Met Met Ile Thr Arg Gly Gly Ala Lys Ala Ala Lys Ser Leu
           1               5                  10 ctg gtg gcg gcc gga ccc cgc ctg ttc agc acc gtc cgc acc gtg agc     99
Leu Val Ala Ala Gly Pro Arg Leu Phe Ser Thr Val Arg Thr Val Ser
15                  20                  25                  30
```

| | | |
|---|---|---|
| tcg cac gag gcg ctg agc gcc agc cac atc ctg aag ccc ggt gtg acc<br>Ser His Glu Ala Leu Ser Ala Ser His Ile Leu Lys Pro Gly Val Thr<br>              35                    40                  45 | 147 |
| agc gcc tgg atc tgg acc cgc gcc ccg acg atc gga ggc atg cgc ttc<br>Ser Ala Trp Ile Trp Thr Arg Ala Pro Thr Ile Gly Gly Met Arg Phe<br>        50                    55                    60 | 195 |
| gtg gac ccg cat atc ctc tgg tgg aag gag aag atg gag cgc tgc agg<br>Val Asp Pro His Ile Leu Trp Trp Lys Glu Lys Met Glu Arg Cys Arg<br>              65                    70                75 | 243 |
| aag ccc agc tcg atg cag ctg acc cag cgc ctg gtc tac agc aac atc<br>Lys Pro Ser Ser Met Gln Leu Thr Gln Arg Leu Val Tyr Ser Asn Ile<br>     80                    85                    90 | 291 |
| ctg ggc ctg gac ccg acc ctg cgc aac ggc agc ctg aag gac ggc tcg<br>Leu Gly Leu Asp Pro Thr Leu Arg Asn Gly Ser Leu Lys Asp Gly Ser<br>95                    100                  105                  110 | 339 |
| ctg aac acg gag atg ctg cag ttc aag agc aag ttc ccg cgc gag gtc<br>Leu Asn Thr Glu Met Leu Gln Phe Lys Ser Lys Phe Pro Arg Glu Val<br>                  115                  120                  125 | 387 |
| ctg ctc tgc cgc gtc ggc gac ttc tac gag gcc gtc ggc ttc gac gcg<br>Leu Leu Cys Arg Val Gly Asp Phe Tyr Glu Ala Val Gly Phe Asp Ala<br>            130                  135                  140 | 435 |
| tgc atc ctg gtg gag cac gcc ggc ctg aac ccc ttc gga ggc ctg cgc<br>Cys Ile Leu Val Glu His Ala Gly Leu Asn Pro Phe Gly Gly Leu Arg<br>        145                    150                  155 | 483 |
| agc gac agc att cca aag gcg ggc tgc cca gtg atg aac ttg cgc cag<br>Ser Asp Ser Ile Pro Lys Ala Gly Cys Pro Val Met Asn Leu Arg Gln<br>            160                  165                  170 | 531 |
| acc ctg gac gac ctg acc cga tgt ggt tac agc gtc tgc atc gtc gag<br>Thr Leu Asp Asp Leu Thr Arg Cys Gly Tyr Ser Val Cys Ile Val Glu<br>175                   180                  185                  190 | 579 |
| gaa atc cag ggg cca acc cag gcc agg gct cgc aag ggc cga ttc atc<br>Glu Ile Gln Gly Pro Thr Gln Ala Arg Ala Arg Lys Gly Arg Phe Ile<br>                  195                  200                  205 | 627 |
| agc ggc cac gcg cac cct ggc agc cct tac gtc ttc ggt ctg gct gag<br>Ser Gly His Ala His Pro Gly Ser Pro Tyr Val Phe Gly Leu Ala Glu<br>            210                  215                  220 | 675 |
| gtc gac cac gac gtc gag ttc ccc gac cca atg ccc gtc gtc ggg att<br>Val Asp His Asp Val Glu Phe Pro Asp Pro Met Pro Val Val Gly Ile<br>        225                    230                  235 | 723 |
| agc cgc agc gcc aag ggc tac tgc ctg atc agc gtg ctg gag acc atg<br>Ser Arg Ser Ala Lys Gly Tyr Cys Leu Ile Ser Val Leu Glu Thr Met<br>        240                    245                  250 | 771 |
| aag acc tac agc gcc gag gag ggc ctg acc gag gag gcc gtc gtc act<br>Lys Thr Tyr Ser Ala Glu Glu Gly Leu Thr Glu Glu Ala Val Val Thr<br>255                   260                  265                  270 | 819 |
| aag ctg cgc atc tgc cgc tac cac cat ctg tac ctg cac agc agc ctg<br>Lys Leu Arg Ile Cys Arg Tyr His His Leu Tyr Leu His Ser Ser Leu<br>                  275                  280                  285 | 867 |
| cgc aac aac agc tca ggg acc agc cgc tgg ggc gag ttc ggc gag ggc<br>Arg Asn Asn Ser Ser Gly Thr Ser Arg Trp Gly Glu Phe Gly Glu Gly<br>            290                  295                  300 | 915 |
| ggg ctg ctg tgg ggc gag tgc agc ggc aag agc ttc gag tgg ttc gac<br>Gly Leu Leu Trp Gly Glu Cys Ser Gly Lys Ser Phe Glu Trp Phe Asp<br>        305                    310                  315 | 963 |
| ggg aac ccc atc gag gaa ctc tgt aag gtg cgc gaa atc tac ggc<br>Gly Asn Pro Ile Glu Glu Leu Cys Lys Val Arg Glu Ile Tyr Gly<br>        320                    325                  330 | 1011 |
| ctc gag gag aag acc gtg ttc cgc aac gtg agc gtc agc ctg gag ggg<br>Leu Glu Glu Lys Thr Val Phe Arg Asn Val Ser Val Ser Leu Glu Gly<br>335                   340                  345                  350 | 1059 |

```
cgc cca cag ccc ctg tac ctg gga acc gcg acc cag att ggc gtg atc     1107
Arg Pro Gln Pro Leu Tyr Leu Gly Thr Ala Thr Gln Ile Gly Val Ile
            355                 360                 365 ccg acc gag gga atc ccc agc ctg ctg aag atc gtg ctg cct ccg aac     1155
Pro Thr Glu Gly Ile Pro Ser Leu Leu Lys Ile Val Leu Pro Pro Asn
        370                 375                 380 ttc ggt ggc ctg ccc agc ctg tac atc cgc gac ctg ctc ctg aac cct     1203
Phe Gly Gly Leu Pro Ser Leu Tyr Ile Arg Asp Leu Leu Leu Asn Pro
    385                 390                 395 ccg agc ttc gac gtg gcg agc tcg gtg cag gag gcg tgc cgc ctg atg     1251
Pro Ser Phe Asp Val Ala Ser Ser Val Gln Glu Ala Cys Arg Leu Met
400                 405                 410 ggc agc atc acc tgc agc atc cct gag ttc acc tgc atc ccg gct gcc     1299
Gly Ser Ile Thr Cys Ser Ile Pro Glu Phe Thr Cys Ile Pro Ala Ala
415                 420                 425                 430 aag ctg gtg aag ctg ctc gag agc aag gag gtg aac cac atc gag ttc     1347
Lys Leu Val Lys Leu Leu Glu Ser Lys Glu Val Asn His Ile Glu Phe
                435                 440                 445 tgc cgc atc aag aac gtc ctg gac gag gtc ctg ttc atg ggc agc aac     1395
Cys Arg Ile Lys Asn Val Leu Asp Glu Val Leu Phe Met Gly Ser Asn
            450                 455                 460 gcg gag ctc agc gcc atc ctg aac aag ctg ctc gac cct gcg gcc ata     1443
Ala Glu Leu Ser Ala Ile Leu Asn Lys Leu Leu Asp Pro Ala Ala Ile
        465                 470                 475 gtg acc ggg ttc aag gtc gag gcc gac atc ctg gtg aac gag tgc agc     1491
Val Thr Gly Phe Lys Val Glu Ala Asp Ile Leu Val Asn Glu Cys Ser
    480                 485                 490 ttc atc agc cag cgc atc gcg gag gtc atc agc ctg ggt ggc gag agc     1539
Phe Ile Ser Gln Arg Ile Ala Glu Val Ile Ser Leu Gly Gly Glu Ser
495                 500                 505                 510 gac cag gcg atc acc agc tcc gag tac atc ccg aag gag ttc ttc aac     1587
Asp Gln Ala Ile Thr Ser Ser Glu Tyr Ile Pro Lys Glu Phe Phe Asn
                515                 520                 525 gac atg gag agc tcg tgg aag gga cgc gtg aag cgc gtg cac gcc gag     1635
Asp Met Glu Ser Ser Trp Lys Gly Arg Val Lys Arg Val His Ala Glu
            530                 535                 540 gaa gag ttc agc aac gtc gac ata gcg gct gag gcc ctg agc acc gcg     1683
Glu Glu Phe Ser Asn Val Asp Ile Ala Ala Glu Ala Leu Ser Thr Ala
        545                 550                 555 gtc att gag gac ttc ctg cca atc atc agc cgc gtg aag agc gtg atg     1731
Val Ile Glu Asp Phe Leu Pro Ile Ile Ser Arg Val Lys Ser Val Met
560                 565                 570 agc tcc aac gga agc tcc aag gga gag atc agc tac gcg aag gag cac     1779
Ser Ser Asn Gly Ser Ser Lys Gly Glu Ile Ser Tyr Ala Lys Glu His
575                 580                 585                 590 gag agc gtg tgg ttc aag ggc agg cgc ttc acc cca aac gtg tgg gcg     1827
Glu Ser Val Trp Phe Lys Gly Arg Arg Phe Thr Pro Asn Val Trp Ala
                595                 600                 605 aac acc cct ggg gag ctg cag atc aag cag ctg aag cct gcg atc gac     1875
Asn Thr Pro Gly Glu Leu Gln Ile Lys Gln Leu Lys Pro Ala Ile Asp
            610                 615                 620 agc aag ggt cgc aag gtg gga gag gaa tgg ttc acg acc atc aag gtg     1923
Ser Lys Gly Arg Lys Val Gly Glu Glu Trp Phe Thr Thr Ile Lys Val
        625                 630                 635 gag aac gcc ctg acc cgc tac cac gag gcg tgc gac aac gcg aag cgc     1971
Glu Asn Ala Leu Thr Arg Tyr His Glu Ala Cys Asp Asn Ala Lys Arg
    640                 645                 650 aag gtc ctg gag ctg ctg cgc gga ctg agc agc gag ctg cag gac aag     2019
Lys Val Leu Glu Leu Leu Arg Gly Leu Ser Ser Glu Leu Gln Asp Lys
```

```
                        655                 660                 665                 670
atc aac gtg ctg gtc ttc tgc agc acc atg ctg atc atc acc aag gca      2067
Ile Asn Val Leu Val Phe Cys Ser Thr Met Leu Ile Ile Thr Lys Ala
                        675                 680                 685 ctg ttc ggt cac gtg agc gag gga cgc agg cgc ggt tgg gtc ctg cct      2115
Leu Phe Gly His Val Ser Glu Gly Arg Arg Arg Gly Trp Val Leu Pro
                        690                 695                 700 acc atc tcg ccc ctg tgc aag gac aac gtc acc gag gag atc agc agt      2163
Thr Ile Ser Pro Leu Cys Lys Asp Asn Val Thr Glu Glu Ile Ser Ser
                        705                 710                 715 gag atg gag ctg agc gga acc ttc cct tac tgg ctg gac acc aac cag      2211
Glu Met Glu Leu Ser Gly Thr Phe Pro Tyr Trp Leu Asp Thr Asn Gln
                        720                 725                 730 ggg aac gca atc ctg aac gac gtc cac atg cac agc ctg ttc atc ctg      2259
Gly Asn Ala Ile Leu Asn Asp Val His Met His Ser Leu Phe Ile Leu
735                     740                 745                 750 act ggt ccc aac ggt ggc ggt aag agc agc atg ctg cgc agc gtc tgc      2307
Thr Gly Pro Asn Gly Gly Gly Lys Ser Ser Met Leu Arg Ser Val Cys
                        755                 760                 765 gct gcc gcg ctg ctt ggg atc tgc ggc ctg atg gtc cca gcg gct agc      2355
Ala Ala Ala Leu Leu Gly Ile Cys Gly Leu Met Val Pro Ala Ala Ser
                        770                 775                 780 gct gtg atc cca cac ttc gac agc atc atg ctg cac atg aag gca tac      2403
Ala Val Ile Pro His Phe Asp Ser Ile Met Leu His Met Lys Ala Tyr
                        785                 790                 795 gac agc cca gcg gac ggt aag agc tcg ttc cag atc gag atg agc gag      2451
Asp Ser Pro Ala Asp Gly Lys Ser Ser Phe Gln Ile Glu Met Ser Glu
                        800                 805                 810 atc cgc agc ctg gtc tgc cgc gct acc gct agg agc ctg gtg ctg atc      2499
Ile Arg Ser Leu Val Cys Arg Ala Thr Ala Arg Ser Leu Val Leu Ile
815                     820                 825                 830 gac gaa atc tgc agg ggg acc gag acc gcg aag gga acc tgc atc gct      2547
Asp Glu Ile Cys Arg Gly Thr Glu Thr Ala Lys Gly Thr Cys Ile Ala
                        835                 840                 845 ggc agc atc atc gag cgc ctc gac aac gtg ggc tgc atc ggc atc atc      2595
Gly Ser Ile Ile Glu Arg Leu Asp Asn Val Gly Cys Ile Gly Ile Ile
                        850                 855                 860 agc acc cac ctg cac ggc atc ttc gac ctg cca ctg agc ctg cac aac      2643
Ser Thr His Leu His Gly Ile Phe Asp Leu Pro Leu Ser Leu His Asn
                        865                 870                 875 acc gac ttc aag gct atg ggc acc gag atc atc gac cgc tgc atc cag      2691
Thr Asp Phe Lys Ala Met Gly Thr Glu Ile Ile Asp Arg Cys Ile Gln
                        880                 885                 890 cca acc tgg aag ctg atg gac ggc atc tgc aga gag agc ctg gcg ttc      2739
Pro Thr Trp Lys Leu Met Asp Gly Ile Cys Arg Glu Ser Leu Ala Phe
895                     900                 905                 910 cag acc gcc agg aag gag ggt atg ccg gac ctg atc atc aga cgc gct      2787
Gln Thr Ala Arg Lys Glu Gly Met Pro Asp Leu Ile Ile Arg Arg Ala
                        915                 920                 925 gag gag ctg tac ctc gct atg agc acc aac agc aag cag acc agc tcg      2835
Glu Glu Leu Tyr Leu Ala Met Ser Thr Asn Ser Lys Gln Thr Ser Ser
                        930                 935                 940 gct gtg cac cat gag atc agc atc gcc aac agc acc gtg aac agc ctg      2883
Ala Val His His Glu Ile Ser Ile Ala Asn Ser Thr Val Asn Ser Leu
                        945                 950                 955 gtg gag aag cct aac tac ctg cgc aac ggg ctg gag ctg cag agc ggt      2931
Val Glu Lys Pro Asn Tyr Leu Arg Asn Gly Leu Glu Leu Gln Ser Gly
                        960                 965                 970 agc ttc gga ctg ctg aga aag gag atc gag agc gtg gtc acc aca atc      2979
```

```
Ser Phe Gly Leu Leu Arg Lys Glu Ile Glu Ser Val Val Thr Thr Ile
975                 980                 985                 990 tgc aag aag aaa ctg ctg gac ctg tac aac aag cgc agc atc tcg gag    3027
Cys Lys Lys Lys Leu Leu Asp Leu Tyr Asn Lys Arg Ser Ile Ser Glu
                995                 1000                1005 ctg atc gag gtc gtg tgc gtg gct gtg ggt gcg cgc gag cag ccg        3072
Leu Ile Glu Val Val Cys Val Ala Val Gly Ala Arg Glu Gln Pro
        1010                1015                1020 cca cct agc acc gtg ggc agg agc tcg atc tac gtg att atc cgc        3117
Pro Pro Ser Thr Val Gly Arg Ser Ser Ile Tyr Val Ile Ile Arg
        1025                1030                1035 cgc gac agc aag ctg tac atc gga cag acg gac gac ctg gtg ggt        3162
Arg Asp Ser Lys Leu Tyr Ile Gly Gln Thr Asp Asp Leu Val Gly
        1040                1045                1050 cgc ctg agc gct cac agg agc aag gag ggt atg cag gac gcg acg        3207
Arg Leu Ser Ala His Arg Ser Lys Glu Gly Met Gln Asp Ala Thr
        1055                1060                1065 atc ctg tac atc ctg gta cct ggc aag agc atc gca tgc cag ctg        3252
Ile Leu Tyr Ile Leu Val Pro Gly Lys Ser Ile Ala Cys Gln Leu
        1070                1075                1080 gag acc ctg ctc atc aac cag ctg cct ctg aag ggt ttc aag ctg        3297
Glu Thr Leu Leu Ile Asn Gln Leu Pro Leu Lys Gly Phe Lys Leu
        1085                1090                1095 atc aac aag gcg gac ggc aag cac cga aac ttc ggt atc tct ctg        3342
Ile Asn Lys Ala Asp Gly Lys His Arg Asn Phe Gly Ile Ser Leu
        1100                1105                1110 gtc cca ggc gag gca atc gcg gca tag aatgagctct gtccaacagt          3389
Val Pro Gly Glu Ala Ile Ala Ala
        1115 ctcagggtta atgtctatgt atcttaaata atgttgtcgg cgatcgttca aacatttggc  3449 aataaagttt cttaagattg aatcctgttg ccggtcttgc gatgattatc atataatttc  3509 tgttgaatta cgttaagcat gtaataatta acatgtaatg catgacgtta tttatgagat  3569 gggttttat gattagagtc ccgcaattat acatttaata cgcgatagaa acaaaatat    3629 agcgcgcaaa ctaggataaa ttatcgcgcg cggtgtcatc tatgttacta gatccctgca  3689 ggatatataa gcttaaaa                                                3707

<210> SEQ ID NO 8
<211> LENGTH: 64
<212> TYPE: PRT
<213> ORGANISM: Artificial Sequence
<220> FEATURE:
<223> OTHER INFORMATION: Synthetic Construct

<400> SEQUENCE: 8

Met Met Ile Thr Arg Gly Gly Ala Lys Ala Ala Lys Ser Leu Leu Val
1               5                   10                  15

Ala Ala Gly Pro Arg Leu Phe Ser Thr Val Arg Thr Val Ser Ser His
            20                  25                  30

Glu Ala Leu Ser Ala Ser His Ile Leu Lys Pro Gly Val Thr Ser Ala
        35                  40                  45

Trp Ile Trp Thr Arg Ala Pro Thr Ile Gly Gly Met Arg Phe Val Asp
    50                  55                  60

<210> SEQ ID NO 9
<211> LENGTH: 1055
<212> TYPE: PRT
<213> ORGANISM: Artificial Sequence
<220> FEATURE:
```

<223> OTHER INFORMATION: Synthetic Construct

<400> SEQUENCE: 9

```
Pro His Ile Leu Trp Trp Lys Glu Lys Met Glu Arg Cys Arg Lys Pro
 1               5                  10                  15

Ser Ser Met Gln Leu Thr Gln Arg Leu Val Tyr Ser Asn Ile Leu Gly
             20                  25                  30

Leu Asp Pro Thr Leu Arg Asn Gly Ser Leu Lys Asp Gly Ser Leu Asn
         35                  40                  45

Thr Glu Met Leu Gln Phe Lys Ser Lys Phe Pro Arg Glu Val Leu Leu
     50                  55                  60

Cys Arg Val Gly Asp Phe Tyr Glu Ala Val Gly Phe Asp Ala Cys Ile
 65                  70                  75                  80

Leu Val Glu His Ala Gly Leu Asn Pro Phe Gly Gly Leu Arg Ser Asp
                 85                  90                  95

Ser Ile Pro Lys Ala Gly Cys Pro Val Met Asn Leu Arg Gln Thr Leu
             100                 105                 110

Asp Asp Leu Thr Arg Cys Gly Tyr Ser Val Cys Ile Val Glu Glu Ile
         115                 120                 125

Gln Gly Pro Thr Gln Ala Arg Ala Arg Lys Gly Arg Phe Ile Ser Gly
     130                 135                 140

His Ala His Pro Gly Ser Pro Tyr Val Phe Gly Leu Ala Glu Val Asp
145                 150                 155                 160

His Asp Val Glu Phe Pro Asp Pro Met Pro Val Val Gly Ile Ser Arg
                 165                 170                 175

Ser Ala Lys Gly Tyr Cys Leu Ile Ser Val Leu Glu Thr Met Lys Thr
             180                 185                 190

Tyr Ser Ala Glu Glu Gly Leu Thr Glu Glu Ala Val Val Thr Lys Leu
         195                 200                 205

Arg Ile Cys Arg Tyr His His Leu Tyr Leu His Ser Ser Leu Arg Asn
     210                 215                 220

Asn Ser Ser Gly Thr Ser Arg Trp Gly Glu Phe Gly Glu Gly Gly Leu
225                 230                 235                 240

Leu Trp Gly Glu Cys Ser Gly Lys Ser Phe Glu Trp Phe Asp Gly Asn
                 245                 250                 255

Pro Ile Glu Glu Leu Leu Cys Lys Val Arg Glu Ile Tyr Gly Leu Glu
             260                 265                 270

Glu Lys Thr Val Phe Arg Asn Val Ser Val Ser Leu Glu Gly Arg Pro
         275                 280                 285

Gln Pro Leu Tyr Leu Gly Thr Ala Thr Gln Ile Gly Val Ile Pro Thr
     290                 295                 300

Glu Gly Ile Pro Ser Leu Leu Lys Ile Val Leu Pro Pro Asn Phe Gly
305                 310                 315                 320

Gly Leu Pro Ser Leu Tyr Ile Arg Asp Leu Leu Leu Asn Pro Pro Ser
                 325                 330                 335

Phe Asp Val Ala Ser Ser Val Gln Glu Ala Cys Arg Leu Met Gly Ser
             340                 345                 350

Ile Thr Cys Ser Ile Pro Glu Phe Thr Cys Ile Pro Ala Ala Lys Leu
         355                 360                 365

Val Lys Leu Leu Glu Ser Lys Glu Val Asn His Ile Glu Phe Cys Arg
     370                 375                 380

Ile Lys Asn Val Leu Asp Glu Val Leu Phe Met Gly Ser Asn Ala Glu
385                 390                 395                 400
```

-continued

```
Leu Ser Ala Ile Leu Asn Lys Leu Leu Asp Pro Ala Ala Ile Val Thr
                405                 410                 415
Gly Phe Lys Val Glu Ala Asp Ile Leu Val Asn Glu Cys Ser Phe Ile
            420                 425                 430
Ser Gln Arg Ile Ala Glu Val Ile Ser Leu Gly Gly Glu Ser Asp Gln
        435                 440                 445
Ala Ile Thr Ser Ser Glu Tyr Ile Pro Lys Glu Phe Phe Asn Asp Met
    450                 455                 460
Glu Ser Ser Trp Lys Gly Arg Val Lys Arg Val His Ala Glu Glu Glu
465                 470                 475                 480
Phe Ser Asn Val Asp Ile Ala Ala Glu Ala Leu Ser Thr Ala Val Ile
                485                 490                 495
Glu Asp Phe Leu Pro Ile Ile Ser Arg Val Lys Ser Val Met Ser Ser
            500                 505                 510
Asn Gly Ser Ser Lys Gly Glu Ile Ser Tyr Ala Lys Glu His Glu Ser
        515                 520                 525
Val Trp Phe Lys Gly Arg Arg Phe Thr Pro Asn Val Trp Ala Asn Thr
    530                 535                 540
Pro Gly Glu Leu Gln Ile Lys Gln Leu Lys Pro Ala Ile Asp Ser Lys
545                 550                 555                 560
Gly Arg Lys Val Gly Glu Glu Trp Phe Thr Thr Ile Lys Val Glu Asn
                565                 570                 575
Ala Leu Thr Arg Tyr His Glu Ala Cys Asp Asn Ala Lys Arg Lys Val
            580                 585                 590
Leu Glu Leu Leu Arg Gly Leu Ser Ser Glu Leu Gln Asp Lys Ile Asn
        595                 600                 605
Val Leu Val Phe Cys Ser Thr Met Leu Ile Ile Thr Lys Ala Leu Phe
    610                 615                 620
Gly His Val Ser Glu Gly Arg Arg Gly Trp Val Leu Pro Thr Ile
625                 630                 635                 640
Ser Pro Leu Cys Lys Asp Asn Val Thr Glu Glu Ile Ser Ser Glu Met
                645                 650                 655
Glu Leu Ser Gly Thr Phe Pro Tyr Trp Leu Asp Thr Asn Gln Gly Asn
            660                 665                 670
Ala Ile Leu Asn Asp Val His Met His Ser Leu Phe Ile Leu Thr Gly
        675                 680                 685
Pro Asn Gly Gly Gly Lys Ser Ser Met Leu Arg Ser Val Cys Ala Ala
    690                 695                 700
Ala Leu Leu Gly Ile Cys Gly Leu Met Val Pro Ala Ala Ser Ala Val
705                 710                 715                 720
Ile Pro His Phe Asp Ser Ile Met Leu His Met Lys Ala Tyr Asp Ser
                725                 730                 735
Pro Ala Asp Gly Lys Ser Ser Phe Gln Ile Glu Met Ser Glu Ile Arg
            740                 745                 750
Ser Leu Val Cys Arg Ala Thr Ala Arg Ser Leu Val Leu Ile Asp Glu
        755                 760                 765
Ile Cys Arg Gly Thr Glu Thr Ala Lys Gly Thr Cys Ile Ala Gly Ser
    770                 775                 780
Ile Ile Glu Arg Leu Asp Asn Val Gly Cys Ile Gly Ile Ile Ser Thr
785                 790                 795                 800
His Leu His Gly Ile Phe Asp Leu Pro Leu Ser Leu His Asn Thr Asp
                805                 810                 815
Phe Lys Ala Met Gly Thr Glu Ile Ile Asp Arg Cys Ile Gln Pro Thr
```

```
                820             825             830
Trp Lys Leu Met Asp Gly Ile Cys Arg Glu Ser Leu Ala Phe Gln Thr
            835             840             845

Ala Arg Lys Glu Gly Met Pro Asp Leu Ile Ile Arg Arg Ala Glu Glu
    850             855             860

Leu Tyr Leu Ala Met Ser Thr Asn Ser Lys Gln Thr Ser Ser Ala Val
865             870             875             880

His His Glu Ile Ser Ile Ala Asn Ser Thr Val Asn Ser Leu Val Glu
                885             890             895

Lys Pro Asn Tyr Leu Arg Asn Gly Leu Glu Leu Gln Ser Gly Ser Phe
            900             905             910

Gly Leu Leu Arg Lys Glu Ile Glu Ser Val Val Thr Thr Ile Cys Lys
            915             920             925

Lys Lys Leu Leu Asp Leu Tyr Asn Lys Arg Ser Ile Ser Glu Leu Ile
            930             935             940

Glu Val Val Cys Val Ala Val Gly Ala Arg Glu Gln Pro Pro Pro Ser
945             950             955             960

Thr Val Gly Arg Ser Ser Ile Tyr Val Ile Arg Arg Asp Ser Lys
            965             970             975

Leu Tyr Ile Gly Gln Thr Asp Asp Leu Val Gly Arg Leu Ser Ala His
            980             985             990

Arg Ser Lys Glu Gly Met Gln Asp  Ala Thr Ile Leu Tyr  Ile Leu Val
            995             1000             1005

Pro Gly  Lys Ser Ile Ala Cys  Gln Leu Glu Thr Leu  Leu Ile Asn
    1010             1015             1020

Gln Leu  Pro Leu Lys Gly Phe  Lys Leu Ile Asn Lys  Ala Asp Gly
    1025             1030             1035

Lys His  Arg Asn Phe Gly Ile  Ser Leu Val Pro Gly  Glu Ala Ile
    1040             1045             1050

Ala Ala
    1055

<210> SEQ ID NO 10
<211> LENGTH: 581
<212> TYPE: DNA
<213> ORGANISM: Streptomyces hygroscopicus
<220> FEATURE:
<221> NAME/KEY: 5'UTR
<222> LOCATION: (1)..(20)
<220> FEATURE:
<221> NAME/KEY: CDS
<222> LOCATION: (21)..(575)
<223> OTHER INFORMATION: Streptomyces hygroscopicus BAR gene CDS
<220> FEATURE:
<221> NAME/KEY: 3'UTR
<222> LOCATION: (576)..(581)

<400> SEQUENCE: 10
ctcgagcccg gggatctacc atg agc cca gaa cga cgc ccg gcc gac atc cgc    53
                     Met Ser Pro Glu Arg Arg Pro Ala Asp Ile Arg
                         1               5                  10 cgt gcc acc gag gcg gac atg ccg gcg gtc tgc acc atc gtc aac cac    101
Arg Ala Thr Glu Ala Asp Met Pro Ala Val Cys Thr Ile Val Asn His
        15                  20                  25 tac atc gag aca agc acg gtc aac ttc cgt acc gag ccg cag gaa ccg    149
Tyr Ile Glu Thr Ser Thr Val Asn Phe Arg Thr Glu Pro Gln Glu Pro
            30                  35                  40 cag gag tgg acg gac gac ctc gtc cgt ctg cgg gag cgc tat ccc tgg    197
Gln Glu Trp Thr Asp Asp Leu Val Arg Leu Arg Glu Arg Tyr Pro Trp
```

```
                     45                  50                  55
ctc gtc gcc gag gtg gac ggc gag gtc gcc ggc atc gcc tac gcg ggc     245
Leu Val Ala Glu Val Asp Gly Glu Val Ala Gly Ile Ala Tyr Ala Gly
60                  65                  70                  75 ccc tgg aag gca cgc aac gcc tac gac tgg acg gcc gaa tcg acc gtg     293
Pro Trp Lys Ala Arg Asn Ala Tyr Asp Trp Thr Ala Glu Ser Thr Val
                80                  85                  90 tac gtc tcc ccc cgc cac cag cgg acg gga ctg ggc tcc acg ctc tac     341
Tyr Val Ser Pro Arg His Gln Arg Thr Gly Leu Gly Ser Thr Leu Tyr
                95                 100                 105 acc cac ctg ctg aag tcc ctg gag gca cag ggc ttc aag agc gtg gtc     389
Thr His Leu Leu Lys Ser Leu Glu Ala Gln Gly Phe Lys Ser Val Val
                110                 115                 120 gct gtc atc ggg ctg ccc aac gac ccg agc gtg cgc atg cac gag gcg     437
Ala Val Ile Gly Leu Pro Asn Asp Pro Ser Val Arg Met His Glu Ala
125                 130                 135 ctc gga tat gcc cca cgc ggc atg ctg cgg gcg gcc ggc ttc aag cac     485
Leu Gly Tyr Ala Pro Arg Gly Met Leu Arg Ala Ala Gly Phe Lys His
140                 145                 150                 155 ggg aac tgg cat gac gtg ggt ttc tgg cag ctg gac ttc agc ctg cca     533
Gly Asn Trp His Asp Val Gly Phe Trp Gln Leu Asp Phe Ser Leu Pro
                160                 165                 170 gta ccg ccc cgt ccg gtc ctg ccc gtc acc gaa atc tga tga ctcgag     581
Val Pro Pro Arg Pro Val Leu Pro Val Thr Glu Ile
                175                 180

<210> SEQ ID NO 11
<211> LENGTH: 183
<212> TYPE: PRT
<213> ORGANISM: Streptomyces hygroscopicus

<400> SEQUENCE: 11

Met Ser Pro Glu Arg Pro Ala Asp Ile Arg Arg Ala Thr Glu Ala
1               5                   10                  15

Asp Met Pro Ala Val Cys Thr Ile Val Asn His Tyr Ile Glu Thr Ser
                20                  25                  30

Thr Val Asn Phe Arg Thr Glu Pro Gln Glu Pro Gln Glu Trp Thr Asp
                35                  40                  45

Asp Leu Val Arg Leu Arg Glu Arg Tyr Pro Trp Leu Val Ala Glu Val
            50                  55                  60

Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
                100                 105                 110

Ser Leu Glu Ala Gln Gly Phe Lys Ser Val Val Ala Val Ile Gly Leu
            115                 120                 125

Pro Asn Asp Pro Ser Val Arg Met His Glu Ala Leu Gly Tyr Ala Pro
            130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                165                 170                 175

Val Leu Pro Val Thr Glu Ile
                180
```

-continued

```
<210> SEQ ID NO 12
<211> LENGTH: 315
<212> TYPE: DNA
<213> ORGANISM: Oryza sativa
<220> FEATURE:
<221> NAME/KEY: exon
<222> LOCATION: (1)..(315)
<223> OTHER INFORMATION: rice MSH1  Domain VI

<400> SEQUENCE: 12 agc atc tca gaa ctg att gag gtg gtc tgt gtt gct gtg ggt gct agg     48
Ser Ile Ser Glu Leu Ile Glu Val Val Cys Val Ala Val Gly Ala Arg
1               5                   10                  15 gag caa ccc cca cct tca act gtt ggc agg tcc agc att tat gta att     96
Glu Gln Pro Pro Pro Ser Thr Val Gly Arg Ser Ser Ile Tyr Val Ile
            20                  25                  30 atc aga cgt gac agc aag ctc tat att gga cag acg gat gat ctt gtg    144
Ile Arg Arg Asp Ser Lys Leu Tyr Ile Gly Gln Thr Asp Asp Leu Val
        35                  40                  45 ggt cga ctt agt gct cac aga tcg aag gaa ggt atg cag gat gcc acg    192
Gly Arg Leu Ser Ala His Arg Ser Lys Glu Gly Met Gln Asp Ala Thr
50                  55                  60 ata tta tat att ttg gta cct ggg aag agc att gca tgc caa ctg gaa    240
Ile Leu Tyr Ile Leu Val Pro Gly Lys Ser Ile Ala Cys Gln Leu Glu
65                  70                  75                  80 act ctt ctc ata aat cag cta cct ttg aaa ggt ttc aag ctc atc aac    288
Thr Leu Leu Ile Asn Gln Leu Pro Leu Lys Gly Phe Lys Leu Ile Asn
                85                  90                  95 aag gca gat ggc aag cat cga aat ttc                                315
Lys Ala Asp Gly Lys His Arg Asn Phe
            100                 105

<210> SEQ ID NO 13
<211> LENGTH: 3662
<212> TYPE: DNA
<213> ORGANISM: Artificial Sequence
<220> FEATURE:
<223> OTHER INFORMATION: Synthetic gene with rice MSH1 with a rice AOX1
      mitochondrial targeting sequence
<220> FEATURE:
<221> NAME/KEY: 5'UTR
<222> LOCATION: (1)..(9)
<220> FEATURE:
<221> NAME/KEY: CDS
<222> LOCATION: (10)..(156)
<223> OTHER INFORMATION: rice AOX1 mitochondrial targeting signal
<220> FEATURE:
<221> NAME/KEY: CDS
<222> LOCATION: (157)..(3324)
<223> OTHER INFORMATION: synthetic rice MSH1 lacking its native
      targeting signal peptide
<220> FEATURE:
<221> NAME/KEY: polyA_site
<222> LOCATION: (3325)..(3662)
<223> OTHER INFORMATION: NOS 3' polyadenylation site

<400> SEQUENCE: 13 gtcgacacc atg agc tcc cga atg gcc gga gcg acg ctg ctg cgc cac ctg    51
           Met Ser Ser Arg Met Ala Gly Ala Thr Leu Leu Arg His Leu
           1               5                   10 ggc ccc cgc ctg ttc gcc gcc gag cct gtg tac tcc ggg ctc gcc gcg      99
Gly Pro Arg Leu Phe Ala Ala Glu Pro Val Tyr Ser Gly Leu Ala Ala
15                  20                  25                  30 agc gcc agg ggc gtc atg ccc gcc gcc gcg agg att ttc ccc gcg cgg     147
Ser Ala Arg Gly Val Met Pro Ala Ala Ala Arg Ile Phe Pro Ala Arg
            35                  40                  45 atg gtg gac ccg cat atc ctc tgg tgg aag gag aag atg gag cgc tgc     195
```

```
                Met Val Asp Pro His Ile Leu Trp Trp Lys Glu Lys Met Glu Arg Cys
                             50                  55                  60 agg aag ccc agc tcg atg cag ctg acc cag cgc ctg gtc tac agc aac       243
Arg Lys Pro Ser Ser Met Gln Leu Thr Gln Arg Leu Val Tyr Ser Asn
            65                  70                  75 atc ctg ggc ctg gac ccg acc ctg cgc aac ggc agc ctg aag gac ggc       291
Ile Leu Gly Leu Asp Pro Thr Leu Arg Asn Gly Ser Leu Lys Asp Gly
        80                  85                  90 tcg ctg aac acg gag atg ctg cag ttc aag agc aag ttc ccg cgc gag       339
Ser Leu Asn Thr Glu Met Leu Gln Phe Lys Ser Lys Phe Pro Arg Glu
95                 100                 105                 110 gtc ctg ctc tgc cgc gtc ggc gac ttc tac gag gcc gtc ggc ttc gac       387
Val Leu Leu Cys Arg Val Gly Asp Phe Tyr Glu Ala Val Gly Phe Asp
                115                 120                 125 gcg tgc atc ctg gtg gag cac gcc ggc ctg aac ccc ttc gga ggc ctg       435
Ala Cys Ile Leu Val Glu His Ala Gly Leu Asn Pro Phe Gly Gly Leu
            130                 135                 140 cgc agc gac agc att cca aag gcg ggc tgc cca gtg atg aac ttg cgc       483
Arg Ser Asp Ser Ile Pro Lys Ala Gly Cys Pro Val Met Asn Leu Arg
        145                 150                 155 cag acc ctg gac gac ctg acc cga tgt ggt tac agc gtc tgc atc gtc       531
Gln Thr Leu Asp Asp Leu Thr Arg Cys Gly Tyr Ser Val Cys Ile Val
    160                 165                 170 gag gaa atc cag ggg cca acc cag gcc agg gct cgc aag ggc cga ttc       579
Glu Glu Ile Gln Gly Pro Thr Gln Ala Arg Ala Arg Lys Gly Arg Phe
175                 180                 185                 190 atc agc ggc cac gcg cac cct ggc agc cct tac gtc ttc ggt ctg gct       627
Ile Ser Gly His Ala His Pro Gly Ser Pro Tyr Val Phe Gly Leu Ala
                195                 200                 205 gag gtc gac cac gac gtc gag ttc ccc gac cca atg ccc gtc gtc ggg       675
Glu Val Asp His Asp Val Glu Phe Pro Asp Pro Met Pro Val Val Gly
            210                 215                 220 att agc cgc agc gcc aag ggc tac tgc ctg atc agc gtg ctg gag acc       723
Ile Ser Arg Ser Ala Lys Gly Tyr Cys Leu Ile Ser Val Leu Glu Thr
        225                 230                 235 atg aag acc tac agc gcc gag gag ggc ctg acc gag gag gcc gtc gtc       771
Met Lys Thr Tyr Ser Ala Glu Glu Gly Leu Thr Glu Glu Ala Val Val
    240                 245                 250 act aag ctg cgc atc tgc cgc tac cac cat ctg tac ctg cac agc agc       819
Thr Lys Leu Arg Ile Cys Arg Tyr His His Leu Tyr Leu His Ser Ser
255                 260                 265                 270 ctg cgc aac aac agc tca ggg acc agc cgc tgg ggc gag ttc ggc gag       867
Leu Arg Asn Asn Ser Ser Gly Thr Ser Arg Trp Gly Glu Phe Gly Glu
                275                 280                 285 ggc ggg ctg ctg tgg ggc gag tgc agc ggc aag agc ttc gag tgg ttc       915
Gly Gly Leu Leu Trp Gly Glu Cys Ser Gly Lys Ser Phe Glu Trp Phe
            290                 295                 300 gac ggg aac ccc atc gag gaa ctc ctg tgc aag gtg cgc gaa atc tac       963
Asp Gly Asn Pro Ile Glu Glu Leu Leu Cys Lys Val Arg Glu Ile Tyr
        305                 310                 315 ggc ctc gag gag aag acc gtg ttc cgc aac gtg agc gtc agc ctg gag      1011
Gly Leu Glu Glu Lys Thr Val Phe Arg Asn Val Ser Val Ser Leu Glu
    320                 325                 330 ggg cgc cca cag ccc ctg tac ctg gga acc gcg acc cag att ggc gtg      1059
Gly Arg Pro Gln Pro Leu Tyr Leu Gly Thr Ala Thr Gln Ile Gly Val
335                 340                 345                 350 atc ccg acc gag gga atc ccc agc ctg ctg aag atc gtc ctg cct ccg      1107
Ile Pro Thr Glu Gly Ile Pro Ser Leu Leu Lys Ile Val Leu Pro Pro
                355                 360                 365
```

| | | |
|---|---|---|
| aac ttc ggt ggc ctg ccc agc ctg tac atc cgc gac ctg ctc ctg aac<br>Asn Phe Gly Gly Leu Pro Ser Leu Tyr Ile Arg Asp Leu Leu Leu Asn<br>370                      375                    380 | | 1155 |
| cct ccg agc ttc gac gtg gcg agc tcg gtg cag gag gcg tgc cgc ctg<br>Pro Pro Ser Phe Asp Val Ala Ser Ser Val Gln Glu Ala Cys Arg Leu<br>385                      390                    395 | | 1203 |
| atg ggc agc atc acc tgc agc atc cct gag ttc acc tgc atc ccg gct<br>Met Gly Ser Ile Thr Cys Ser Ile Pro Glu Phe Thr Cys Ile Pro Ala<br>400                      405                    410 | | 1251 |
| gcc aag ctg gtg aag ctg ctc gag agc aag gag gtg aac cac atc gag<br>Ala Lys Leu Val Lys Leu Leu Glu Ser Lys Glu Val Asn His Ile Glu<br>415                      420                    425                    430 | | 1299 |
| ttc tgc cgc atc aag aac gtc ctg gac gag gtc ctg ttc atg ggc agc<br>Phe Cys Arg Ile Lys Asn Val Leu Asp Glu Val Leu Phe Met Gly Ser<br>435                      440                    445 | | 1347 |
| aac gcg gag ctc agc gcc atc ctg aac aag ctc ctc gac cct gcg gcc<br>Asn Ala Glu Leu Ser Ala Ile Leu Asn Lys Leu Leu Asp Pro Ala Ala<br>450                      455                    460 | | 1395 |
| ata gtg acc ggg ttc aag gtc gag gcc gac atc ctg gtg aac gag tgc<br>Ile Val Thr Gly Phe Lys Val Glu Ala Asp Ile Leu Val Asn Glu Cys<br>465                      470                    475 | | 1443 |
| agc ttc atc agc cag cgc atc gcg gag gtc atc agc ctg ggt ggc gag<br>Ser Phe Ile Ser Gln Arg Ile Ala Glu Val Ile Ser Leu Gly Gly Glu<br>480                      485                    490 | | 1491 |
| agc gac cag gcg atc acc agc tcc gag tac atc ccg aag gag ttc ttc<br>Ser Asp Gln Ala Ile Thr Ser Ser Glu Tyr Ile Pro Lys Glu Phe Phe<br>495                      500                    505                    510 | | 1539 |
| aac gac atg gag agc tcg tgg aag gga cgc gtg aag cgc gtg cac gcc<br>Asn Asp Met Glu Ser Ser Trp Lys Gly Arg Val Lys Arg Val His Ala<br>515                      520                    525 | | 1587 |
| gag gaa gag ttc agc aac gtc gac ata gcg gct gag gcc ctg agc acc<br>Glu Glu Glu Phe Ser Asn Val Asp Ile Ala Ala Glu Ala Leu Ser Thr<br>530                      535                    540 | | 1635 |
| gcg gtc att gag gac ttc ctg cca atc atc agc cgc gtg aag agc gtg<br>Ala Val Ile Glu Asp Phe Leu Pro Ile Ile Ser Arg Val Lys Ser Val<br>545                      550                    555 | | 1683 |
| atg agc tcc aac gga agc tcc aag gga gag atc agc tac gcg aag gag<br>Met Ser Ser Asn Gly Ser Ser Lys Gly Glu Ile Ser Tyr Ala Lys Glu<br>560                      565                    570 | | 1731 |
| cac gag agc gtg tgg ttc aag ggc agg cgc ttc acc cca aac gtg tgg<br>His Glu Ser Val Trp Phe Lys Gly Arg Arg Phe Thr Pro Asn Val Trp<br>575                      580                    585                    590 | | 1779 |
| gcg aac acc cct ggg gag ctg cag atc aag cag ctg aag cct gcg atc<br>Ala Asn Thr Pro Gly Glu Leu Gln Ile Lys Gln Leu Lys Pro Ala Ile<br>595                      600                    605 | | 1827 |
| gac agc aag ggt cgc aag gtg gga gag gaa tgg ttc acg acc atc aag<br>Asp Ser Lys Gly Arg Lys Val Gly Glu Glu Trp Phe Thr Thr Ile Lys<br>610                      615                    620 | | 1875 |
| gtg gag aac gcc ctg acc cgc tac cac gag gcg tgc gac aac gcg aag<br>Val Glu Asn Ala Leu Thr Arg Tyr His Glu Ala Cys Asp Asn Ala Lys<br>625                      630                    635 | | 1923 |
| cgc aag gtc ctg gag ctg ctg cgc gga ctg agc agc gag ctg cag gac<br>Arg Lys Val Leu Glu Leu Leu Arg Gly Leu Ser Ser Glu Leu Gln Asp<br>640                      645                    650 | | 1971 |
| aag atc aac gtg ctg gtc ttc tgc agc acc atg ctg atc atc acc aag<br>Lys Ile Asn Val Leu Val Phe Cys Ser Thr Met Leu Ile Ile Thr Lys<br>655                      660                    665                    670 | | 2019 |
| gca ctg ttc ggt cac gtg agc gag gga cgc agg cgc ggt tgg gtc ctg<br>Ala Leu Phe Gly His Val Ser Glu Gly Arg Arg Arg Gly Trp Val Leu<br>675                      680                    685 | | 2067 |

```
cct acc atc tcg ccc ctg tgc aag gac aac gtc acc gag gag atc agc    2115
Pro Thr Ile Ser Pro Leu Cys Lys Asp Asn Val Thr Glu Glu Ile Ser
            690                 695                 700 agt gag atg gag ctg agc gga acc ttc cct tac tgg ctg gac acc aac    2163
Ser Glu Met Glu Leu Ser Gly Thr Phe Pro Tyr Trp Leu Asp Thr Asn
        705                 710                 715 cag ggg aac gca atc ctg aac gac gtc cac atg cac agc ctg ttc atc    2211
Gln Gly Asn Ala Ile Leu Asn Asp Val His Met His Ser Leu Phe Ile
    720                 725                 730 ctg act ggt ccc aac ggt ggc ggt aag agc agc atg ctg cgc agc gtc    2259
Leu Thr Gly Pro Asn Gly Gly Gly Lys Ser Ser Met Leu Arg Ser Val
735                 740                 745                 750 tgc gct gcc gcg ctg ctt ggg atc tgc ggc ctg atg gtc cca gcg gct    2307
Cys Ala Ala Ala Leu Leu Gly Ile Cys Gly Leu Met Val Pro Ala Ala
                755                 760                 765 agc gct gtg atc cca cac ttc gac agc atc atg ctg cac atg aag gca    2355
Ser Ala Val Ile Pro His Phe Asp Ser Ile Met Leu His Met Lys Ala
            770                 775                 780 tac gac agc cca gcg gac ggt aag agc tcg ttc cag atc gag atg agc    2403
Tyr Asp Ser Pro Ala Asp Gly Lys Ser Ser Phe Gln Ile Glu Met Ser
        785                 790                 795 gag atc cgc agc ctg gtc tgc cgc gct acc gct agg agc ctg gtg ctg    2451
Glu Ile Arg Ser Leu Val Cys Arg Ala Thr Ala Arg Ser Leu Val Leu
    800                 805                 810 atc gac gaa atc tgc agg ggg acc gag acc gcg aag gga acc tgc atc    2499
Ile Asp Glu Ile Cys Arg Gly Thr Glu Thr Ala Lys Gly Thr Cys Ile
815                 820                 825                 830 gct ggc agc atc atc gag cgc ctc gac aac gtg ggc tgc atc ggc atc    2547
Ala Gly Ser Ile Ile Glu Arg Leu Asp Asn Val Gly Cys Ile Gly Ile
                835                 840                 845 atc agc acc cac ctg cac ggc atc ttc gac ctg cca ctg agc ctg cac    2595
Ile Ser Thr His Leu His Gly Ile Phe Asp Leu Pro Leu Ser Leu His
            850                 855                 860 aac acc gac ttc aag gct atg ggc acc gag atc atc gac cgc tgc atc    2643
Asn Thr Asp Phe Lys Ala Met Gly Thr Glu Ile Ile Asp Arg Cys Ile
        865                 870                 875 cag cca acc tgg aag ctg atg gac ggc atc tgc aga gag agc ctg gcg    2691
Gln Pro Thr Trp Lys Leu Met Asp Gly Ile Cys Arg Glu Ser Leu Ala
    880                 885                 890 ttc cag acc gcc agg aag gag ggt atg ccg gac ctg atc atc aga cgc    2739
Phe Gln Thr Ala Arg Lys Glu Gly Met Pro Asp Leu Ile Ile Arg Arg
895                 900                 905                 910 gct gag gag ctg tac ctc gct atg agc acc aac agc aag cag acc agc    2787
Ala Glu Glu Leu Tyr Leu Ala Met Ser Thr Asn Ser Lys Gln Thr Ser
                915                 920                 925 tcg gct gtg cac cat gag atc agc atc gcc aac agc acc gtg aac agc    2835
Ser Ala Val His His Glu Ile Ser Ile Ala Asn Ser Thr Val Asn Ser
            930                 935                 940 ctg gtg gag aag cct aac tac ctg cgc aac ggg ctg gag ctg cag agc    2883
Leu Val Glu Lys Pro Asn Tyr Leu Arg Asn Gly Leu Glu Leu Gln Ser
        945                 950                 955 ggt agc ttc gga ctg ctg aga aag gag atc gag agc gtg gtc acc aca    2931
Gly Ser Phe Gly Leu Leu Arg Lys Glu Ile Glu Ser Val Val Thr Thr
    960                 965                 970 atc tgc aag aag aaa ctg ctg gac ctg tac aac aag cgc agc atc tcg    2979
Ile Cys Lys Lys Lys Leu Leu Asp Leu Tyr Asn Lys Arg Ser Ile Ser
975                 980                 985                 990 gag ctg atc gag gtc gtg tgc gtg gct gtg  ggt gcg cgc gag cag  ccg  3027
Glu Leu Ile Glu Val Val Cys Val Ala Val  Gly Ala Arg Glu Gln  Pro
```

|  |  |  |  |  |  |  |  |  |  |  |  | |
|---|---|---|---|---|---|---|---|---|---|---|---|---|
|  |  |  |  | 995 |  |  | 1000 |  |  | 1005 |  | |
| cca | cct | agc | acc | gtg | ggc | agg | agc | tcg | atc | tac | gtg att atc cgc | 3072 |
| Pro | Pro | Ser | Thr | Val | Gly | Arg | Ser | Ser | Ile | Tyr | Val Ile Ile Arg | |
|  |  |  |  | 1010 |  |  | 1015 |  |  |  | 1020 | |
| cgc | gac | agc | aag | ctg | tac | atc | gga | cag | acg | gac | gac ctg gtg ggt | 3117 |
| Arg | Asp | Ser | Lys | Leu | Tyr | Ile | Gly | Gln | Thr | Asp | Asp Leu Val Gly | |
|  |  | 1025 |  |  |  |  | 1030 |  |  |  | 1035 | |
| cgc | ctg | agc | gct | cac | agg | agc | aag | gag | ggt | atg | cag gac gcg acg | 3162 |
| Arg | Leu | Ser | Ala | His | Arg | Ser | Lys | Glu | Gly | Met | Gln Asp Ala Thr | |
|  |  | 1040 |  |  |  |  | 1045 |  |  |  | 1050 | |
| atc | ctg | tac | atc | ctg | gta | cct | ggc | aag | agc | atc | gca tgc cag ctg | 3207 |
| Ile | Leu | Tyr | Ile | Leu | Val | Pro | Gly | Lys | Ser | Ile | Ala Cys Gln Leu | |
|  |  | 1055 |  |  |  |  | 1060 |  |  |  | 1065 | |
| gag | acc | ctg | ctc | atc | aac | cag | ctg | cct | ctg | aag | ggt ttc aag ctg | 3252 |
| Glu | Thr | Leu | Leu | Ile | Asn | Gln | Leu | Pro | Leu | Lys | Gly Phe Lys Leu | |
|  |  | 1070 |  |  |  |  | 1075 |  |  |  | 1080 | |
| atc | aac | aag | gcg | gac | ggc | aag | cac | cga | aac | ttc | ggt atc tct ctg | 3297 |
| Ile | Asn | Lys | Ala | Asp | Gly | Lys | His | Arg | Asn | Phe | Gly Ile Ser Leu | |
|  |  | 1085 |  |  |  |  | 1090 |  |  |  | 1095 | |
| gtc | cca | ggc | gag | gca | atc | gcg | gca | tag | aatgagctct | | gtccaacagt | 3344 |
| Val | Pro | Gly | Glu | Ala | Ile | Ala | Ala | | | | | |
|  |  |  | 1100 |  |  |  |  |  |  |  |  | |

| | |
|---|---|
| ctcagggtta atgtctatgt atcttaaata atgttgtcgg cgatcgttca aacatttggc | 3404 |
| aataaagttt cttaagattg aatcctgttg ccggtcttgc gatgattatc atataatttc | 3464 |
| tgttgaatta cgttaagcat gtaataatta acatgtaatg catgacgtta tttatgagat | 3524 |
| gggttttat gattagagtc ccgcaattat acatttaata cgcgatagaa acaaaatat | 3584 |
| agcgcgcaaa ctaggataaa ttatcgcgcg cggtgtcatc tatgttacta gatccctgca | 3644 |
| ggatatataa gcttaaaa | 3662 |

<210> SEQ ID NO 14
<211> LENGTH: 49
<212> TYPE: PRT
<213> ORGANISM: Artificial Sequence
<220> FEATURE:
<223> OTHER INFORMATION: Synthetic Construct

<400> SEQUENCE: 14

Met Ser Ser Arg Met Ala Gly Ala Thr Leu Leu Arg His Leu Gly Pro
1               5                   10                  15

Arg Leu Phe Ala Ala Glu Pro Val Tyr Ser Gly Leu Ala Ala Ser Ala
            20                  25                  30

Arg Gly Val Met Pro Ala Ala Ala Arg Ile Phe Pro Ala Arg Met Val
        35                  40                  45

Asp

<210> SEQ ID NO 15
<211> LENGTH: 1055
<212> TYPE: PRT
<213> ORGANISM: Artificial Sequence
<220> FEATURE:
<223> OTHER INFORMATION: Synthetic Construct

<400> SEQUENCE: 15

Pro His Ile Leu Trp Trp Lys Glu Lys Met Glu Arg Cys Arg Lys Pro
1               5                   10                  15

Ser Ser Met Gln Leu Thr Gln Arg Leu Val Tyr Ser Asn Ile Leu Gly
            20                  25                  30

```
Leu Asp Pro Thr Leu Arg Asn Gly Ser Leu Lys Asp Gly Ser Leu Asn
            35                  40                  45

Thr Glu Met Leu Gln Phe Lys Ser Lys Phe Pro Arg Glu Val Leu Leu
 50                  55                  60

Cys Arg Val Gly Asp Phe Tyr Glu Ala Val Gly Phe Asp Ala Cys Ile
 65                  70                  75                  80

Leu Val Glu His Ala Gly Leu Asn Pro Phe Gly Gly Leu Arg Ser Asp
                85                  90                  95

Ser Ile Pro Lys Ala Gly Cys Pro Val Met Asn Leu Arg Gln Thr Leu
                100                 105                 110

Asp Asp Leu Thr Arg Cys Gly Tyr Ser Val Cys Ile Val Glu Glu Ile
             115                 120                 125

Gln Gly Pro Thr Gln Ala Arg Ala Arg Lys Gly Arg Phe Ile Ser Gly
         130                 135                 140

His Ala His Pro Gly Ser Pro Tyr Val Phe Gly Leu Ala Glu Val Asp
145                 150                 155                 160

His Asp Val Glu Phe Pro Asp Pro Met Pro Val Val Gly Ile Ser Arg
                165                 170                 175

Ser Ala Lys Gly Tyr Cys Leu Ile Ser Val Leu Glu Thr Met Lys Thr
                180                 185                 190

Tyr Ser Ala Glu Glu Gly Leu Thr Glu Glu Ala Val Val Thr Lys Leu
            195                 200                 205

Arg Ile Cys Arg Tyr His His Leu Tyr Leu His Ser Ser Leu Arg Asn
210                 215                 220

Asn Ser Ser Gly Thr Ser Arg Trp Gly Glu Phe Gly Glu Gly Gly Leu
225                 230                 235                 240

Leu Trp Gly Glu Cys Ser Gly Lys Ser Phe Glu Trp Phe Asp Gly Asn
                245                 250                 255

Pro Ile Glu Glu Leu Leu Cys Lys Val Arg Glu Ile Tyr Gly Leu Glu
                260                 265                 270

Glu Lys Thr Val Phe Arg Asn Val Ser Val Ser Leu Glu Gly Arg Pro
            275                 280                 285

Gln Pro Leu Tyr Leu Gly Thr Ala Thr Gln Ile Gly Val Ile Pro Thr
         290                 295                 300

Glu Gly Ile Pro Ser Leu Leu Lys Ile Val Leu Pro Pro Asn Phe Gly
305                 310                 315                 320

Gly Leu Pro Ser Leu Tyr Ile Arg Asp Leu Leu Leu Asn Pro Pro Ser
                325                 330                 335

Phe Asp Val Ala Ser Ser Val Gln Glu Ala Cys Arg Leu Met Gly Ser
            340                 345                 350

Ile Thr Cys Ser Ile Pro Glu Phe Thr Cys Ile Pro Ala Ala Lys Leu
         355                 360                 365

Val Lys Leu Leu Glu Ser Lys Glu Val Asn His Ile Glu Phe Cys Arg
370                 375                 380

Ile Lys Asn Val Leu Asp Glu Val Leu Phe Met Gly Ser Asn Ala Glu
385                 390                 395                 400

Leu Ser Ala Ile Leu Asn Lys Leu Leu Asp Pro Ala Ala Ile Val Thr
                405                 410                 415

Gly Phe Lys Val Glu Ala Asp Ile Leu Val Asn Glu Cys Ser Phe Ile
            420                 425                 430

Ser Gln Arg Ile Ala Glu Val Ile Ser Leu Gly Gly Glu Ser Asp Gln
         435                 440                 445

Ala Ile Thr Ser Ser Glu Tyr Ile Pro Lys Glu Phe Phe Asn Asp Met
```

```
                450             455             460
Glu Ser Ser Trp Lys Gly Arg Val Lys Arg Val His Ala Glu Glu Glu
465                 470                 475                 480

Phe Ser Asn Val Asp Ile Ala Ala Glu Ala Leu Ser Thr Ala Val Ile
                485                 490                 495

Glu Asp Phe Leu Pro Ile Ile Ser Arg Val Lys Ser Val Met Ser Ser
                500                 505                 510

Asn Gly Ser Ser Lys Gly Glu Ile Ser Tyr Ala Lys Glu His Glu Ser
                515                 520                 525

Val Trp Phe Lys Gly Arg Arg Phe Thr Pro Asn Val Trp Ala Asn Thr
                530                 535                 540

Pro Gly Glu Leu Gln Ile Lys Gln Leu Lys Pro Ala Ile Asp Ser Lys
545                 550                 555                 560

Gly Arg Lys Val Gly Glu Glu Trp Phe Thr Thr Ile Lys Val Glu Asn
                565                 570                 575

Ala Leu Thr Arg Tyr His Glu Ala Cys Asp Asn Ala Lys Arg Lys Val
                580                 585                 590

Leu Glu Leu Leu Arg Gly Leu Ser Ser Glu Leu Gln Asp Lys Ile Asn
                595                 600                 605

Val Leu Val Phe Cys Ser Thr Met Leu Ile Ile Thr Lys Ala Leu Phe
                610                 615                 620

Gly His Val Ser Glu Gly Arg Arg Gly Trp Val Leu Pro Thr Ile
625                 630                 635                 640

Ser Pro Leu Cys Lys Asp Asn Val Thr Glu Glu Ile Ser Ser Glu Met
                645                 650                 655

Glu Leu Ser Gly Thr Phe Pro Tyr Trp Leu Asp Thr Asn Gln Gly Asn
                660                 665                 670

Ala Ile Leu Asn Asp Val His Met His Ser Leu Phe Ile Leu Thr Gly
                675                 680                 685

Pro Asn Gly Gly Gly Lys Ser Ser Met Leu Arg Ser Val Cys Ala Ala
                690                 695                 700

Ala Leu Leu Gly Ile Cys Gly Leu Met Val Pro Ala Ala Ser Ala Val
705                 710                 715                 720

Ile Pro His Phe Asp Ser Ile Met Leu His Met Lys Ala Tyr Asp Ser
                725                 730                 735

Pro Ala Asp Gly Lys Ser Ser Phe Gln Ile Glu Met Ser Glu Ile Arg
                740                 745                 750

Ser Leu Val Cys Arg Ala Thr Ala Arg Ser Leu Val Leu Ile Asp Glu
                755                 760                 765

Ile Cys Arg Gly Thr Glu Thr Ala Lys Gly Thr Cys Ile Ala Gly Ser
                770                 775                 780

Ile Ile Glu Arg Leu Asp Asn Val Gly Cys Ile Gly Ile Ile Ser Thr
785                 790                 795                 800

His Leu His Gly Ile Phe Asp Leu Pro Leu Ser Leu His Asn Thr Asp
                805                 810                 815

Phe Lys Ala Met Gly Thr Glu Ile Ile Asp Arg Cys Ile Gln Pro Thr
                820                 825                 830

Trp Lys Leu Met Asp Gly Ile Cys Arg Glu Ser Leu Ala Phe Gln Thr
                835                 840                 845

Ala Arg Lys Glu Gly Met Pro Asp Leu Ile Ile Arg Arg Ala Glu Glu
                850                 855                 860

Leu Tyr Leu Ala Met Ser Thr Asn Ser Lys Gln Thr Ser Ser Ala Val
865                 870                 875                 880
```

```
His His Glu Ile Ser Ile Ala Asn Ser Thr Val Asn Ser Leu Val Glu
                885                 890                 895
Lys Pro Asn Tyr Leu Arg Asn Gly Leu Glu Leu Gln Ser Gly Ser Phe
            900                 905                 910
Gly Leu Leu Arg Lys Glu Ile Glu Ser Val Val Thr Thr Ile Cys Lys
                915                 920                 925
Lys Lys Leu Leu Asp Leu Tyr Asn Lys Arg Ser Ile Ser Glu Leu Ile
        930                 935                 940
Glu Val Val Cys Val Ala Val Gly Ala Arg Glu Gln Pro Pro Pro Ser
945                 950                 955                 960
Thr Val Gly Arg Ser Ser Ile Tyr Val Ile Arg Arg Asp Ser Lys
                965                 970                 975
Leu Tyr Ile Gly Gln Thr Asp Asp Leu Val Gly Arg Leu Ser Ala His
                980                 985                 990
Arg Ser Lys Glu Gly Met Gln Asp Ala Thr Ile Leu Tyr Ile Leu Val
            995                 1000                1005
Pro Gly Lys Ser Ile Ala Cys Gln Leu Glu Thr Leu Leu Ile Asn
        1010                1015                1020
Gln Leu Pro Leu Lys Gly Phe Lys Leu Ile Asn Lys Ala Asp Gly
    1025                1030                1035
Lys His Arg Asn Phe Gly Ile Ser Leu Val Pro Gly Glu Ala Ile
    1040                1045                1050
Ala Ala
    1055

<210> SEQ ID NO 16
<211> LENGTH: 318
<212> TYPE: DNA
<213> ORGANISM: Zea mays
<220> FEATURE:
<221> NAME/KEY: exon
<222> LOCATION: (1)..(318)
<223> OTHER INFORMATION: Zea mays MSH1 domain VI

<400> SEQUENCE: 16 agc atc cca gaa ctg gtc gag gtg gtc tgc gtt gct gta ggt gct aga    48
Ser Ile Pro Glu Leu Val Glu Val Val Cys Val Ala Val Gly Ala Arg
1               5                   10                  15 gag caa cca ccg cct tcc act gtt ggc aga tct agc atc tac gtg att    96
Glu Gln Pro Pro Pro Ser Thr Val Gly Arg Ser Ser Ile Tyr Val Ile
                20                  25                  30 atc aga agc gac aac agg ctc tat gtt gga cag acg gac gat ctt ctg   144
Ile Arg Ser Asp Asn Arg Leu Tyr Val Gly Gln Thr Asp Asp Leu Leu
            35                  40                  45 ggg cgc ttg aac gcc cac aga tcg aag gaa ggc atg cgg gac gct acg   192
Gly Arg Leu Asn Ala His Arg Ser Lys Glu Gly Met Arg Asp Ala Thr
        50                  55                  60 gta tta tac gtc ttg gtc cct ggc aag agc gtt gcc tgc cag ctg gaa   240
Val Leu Tyr Val Leu Val Pro Gly Lys Ser Val Ala Cys Gln Leu Glu
65                  70                  75                  80 acc ctt ctc ata aac cag ctc cct tcg agg ggc ttc aag ctc atc aac   288
Thr Leu Leu Ile Asn Gln Leu Pro Ser Arg Gly Phe Lys Leu Ile Asn
                85                  90                  95 aag gca gac ggg aag cac agg aac ttc ggt                            318
Lys Ala Asp Gly Lys His Arg Asn Phe Gly
                100                 105

<210> SEQ ID NO 17
```

```
<211> LENGTH: 3692
<212> TYPE: DNA
<213> ORGANISM: Artificial Sequence
<220> FEATURE:
<223> OTHER INFORMATION: synthetic soybean MSH1 with an Arabidopsis AOX1
      mitochondrial targeting signal
<220> FEATURE:
<221> NAME/KEY: 5'UTR
<222> LOCATION: (1)..(6)
<220> FEATURE:
<221> NAME/KEY: CDS
<222> LOCATION: (7)..(198)
<223> OTHER INFORMATION: Arabidopsis AOX1 targeting signal peptide
<220> FEATURE:
<221> NAME/KEY: CDS
<222> LOCATION: (199)..(3354)
<223> OTHER INFORMATION: Soybean MSH1 protein
<220> FEATURE:
<221> NAME/KEY: polyA_site
<222> LOCATION: (3355)..(3668)
<223> OTHER INFORMATION: NOS 3' polyadenylation region
<220> FEATURE:
<221> NAME/KEY: misc_feature
<222> LOCATION: (3669)..(3692)
<223> OTHER INFORMATION: restriction sites flanking 3' of NOS 3' region

<400> SEQUENCE: 17
```

| | |
|---|---:|
| gtcgac atg atg ata act cgc ggt gga gcc aag gcg gcg aaa tcg ctg<br>       Met Met Ile Thr Arg Gly Gly Ala Lys Ala Ala Lys Ser Leu<br>       1             5                  10 | 48 |
| tta gtg gcg gct gga cca cgt ttg ttc tcg acg gtc cgt acg gtt tcg<br>Leu Val Ala Ala Gly Pro Arg Leu Phe Ser Thr Val Arg Thr Val Ser<br>15                 20               25              30 | 96 |
| tct cac gag gct tta tca gca agc cat att ttg aag cct ggt gtt aca<br>Ser His Glu Ala Leu Ser Ala Ser His Ile Leu Lys Pro Gly Val Thr<br>                35               40               45 | 144 |
| tct gct tgg ata tgg act aga gct ccg acg att gga ggt atg aga ttc<br>Ser Ala Trp Ile Trp Thr Arg Ala Pro Thr Ile Gly Gly Met Arg Phe<br>        50                  55               60 | 192 |
| gtg gac cca cac atc ctg tgg tgg aaa gag cgc ctg cag atg tgc cgc<br>Val Asp Pro His Ile Leu Trp Trp Lys Glu Arg Leu Gln Met Cys Arg<br>65                 70               75 | 240 |
| aag ttc agc acc gtg cag ctg atc gag cgc ctg gag ttc agc aac ctg<br>Lys Phe Ser Thr Val Gln Leu Ile Glu Arg Leu Glu Phe Ser Asn Leu<br>    80                  85               90 | 288 |
| ctc ggc ctg aac agc aac ctg aag aac ggc agc ctg aag gag ggc acc<br>Leu Gly Leu Asn Ser Asn Leu Lys Asn Gly Ser Leu Lys Glu Gly Thr<br>95                 100              105            110 | 336 |
| ctg aac tgg gag atg ctg cag ttc aag agc aag ttc cca cgc cag gtc<br>Leu Asn Trp Glu Met Leu Gln Phe Lys Ser Lys Phe Pro Arg Gln Val<br>                115               120              125 | 384 |
| ctg ctc tgc cgc gtc ggc gag ttc tac gag gcc tgg gga atc gac gcc<br>Leu Leu Cys Arg Val Gly Glu Phe Tyr Glu Ala Trp Gly Ile Asp Ala<br>            130               135              140 | 432 |
| tgc atc ctg gtc gag tac gtg ggc ctg aac ccc atc ggt ggc ctg cgc<br>Cys Ile Leu Val Glu Tyr Val Gly Leu Asn Pro Ile Gly Gly Leu Arg<br>145                150               155 | 480 |
| agc gac agc atc cca cgc gct agc tgc cct gtg gtc aac ctg cgc cag<br>Ser Asp Ser Ile Pro Arg Ala Ser Cys Pro Val Val Asn Leu Arg Gln<br>        160               165              170 | 528 |
| acc ctg gac gat ctg acc aca aac ggc tac agc gtc tgc atc gtc gag<br>Thr Leu Asp Asp Leu Thr Thr Asn Gly Tyr Ser Val Cys Ile Val Glu<br>175                180               185            190 | 576 |
| gag gcc cag ggg cca agc cag gcc cgc agc agg aag cgc cgc ttc atc<br>Glu Ala Gln Gly Pro Ser Gln Ala Arg Ser Arg Lys Arg Arg Phe Ile<br>                195               200              205 | 624 |

```
agc ggc cac gcc cac cct gga aac ccg tac gtc tac gga ctg gct acc      672
Ser Gly His Ala His Pro Gly Asn Pro Tyr Val Tyr Gly Leu Ala Thr
            210                 215                 220 gtg gac cac gac ctg aac ttc cca gag ccc atg cct gtc gtc gga atc      720
Val Asp His Asp Leu Asn Phe Pro Glu Pro Met Pro Val Val Gly Ile
                225                 230                 235 agc cac agc gcc cgc ggt tac tgc atc aac atg gta ctg gag acc atg      768
Ser His Ser Ala Arg Gly Tyr Cys Ile Asn Met Val Leu Glu Thr Met
            240                 245                 250 aag acc tac agc tct gag gac tgc ctg acc gag gag gca gtc gtg acc      816
Lys Thr Tyr Ser Ser Glu Asp Cys Leu Thr Glu Glu Ala Val Val Thr
255                 260                 265                 270 aag ctg cgc acc tgc cag tac cac tac ctg ttc ctg cac acc agc ctg      864
Lys Leu Arg Thr Cys Gln Tyr His Tyr Leu Phe Leu His Thr Ser Leu
                275                 280                 285 cgc cgg aac agc tgc ggc acc tgc aac tgg ggc gag ttc ggc gag gga      912
Arg Arg Asn Ser Cys Gly Thr Cys Asn Trp Gly Glu Phe Gly Glu Gly
            290                 295                 300 ggc ctg ctg tgg gga gag tgc agc agc cgc cac ttc gac tgg ttt gac      960
Gly Leu Leu Trp Gly Glu Cys Ser Ser Arg His Phe Asp Trp Phe Asp
                305                 310                 315 ggg aac cct gtg agc gat ctg ctg gcc aag gtg aag gag ctg tac agc     1008
Gly Asn Pro Val Ser Asp Leu Leu Ala Lys Val Lys Glu Leu Tyr Ser
            320                 325                 330 atc gat gat gag gtc acc ttt cgc aac acc act gtg agc tca ggc cac     1056
Ile Asp Asp Glu Val Thr Phe Arg Asn Thr Thr Val Ser Ser Gly His
335                 340                 345                 350 cgc gct cgc cca ctg acc ctg gga acc agc acc cag atc ggt gcg atc     1104
Arg Ala Arg Pro Leu Thr Leu Gly Thr Ser Thr Gln Ile Gly Ala Ile
                355                 360                 365 cca acc gag gga atc cct agc ctg ttg aag gtc ctg ctg cca agc aac     1152
Pro Thr Glu Gly Ile Pro Ser Leu Leu Lys Val Leu Leu Pro Ser Asn
            370                 375                 380 tgc aac ggc ctg cca gtc ctg tac atc cgc gag ctc ctg ttg aac cct     1200
Cys Asn Gly Leu Pro Val Leu Tyr Ile Arg Glu Leu Leu Leu Asn Pro
                385                 390                 395 ccg agc tac gag atc gca agc aag atc cag gcc acc tgc aag ctg atg     1248
Pro Ser Tyr Glu Ile Ala Ser Lys Ile Gln Ala Thr Cys Lys Leu Met
            400                 405                 410 agc agt gtc acc tgc agc atc cca gag ttc acc tgc gtg agc tca gca     1296
Ser Ser Val Thr Cys Ser Ile Pro Glu Phe Thr Cys Val Ser Ser Ala
415                 420                 425                 430 aag ctg gtc aag ctg ctg gag tgg cgc gag gtc aac cac atg gag ttc     1344
Lys Leu Val Lys Leu Leu Glu Trp Arg Glu Val Asn His Met Glu Phe
                435                 440                 445 tgc cgc atc aag aac gtg ctg gac gag atc ctg cag atg tac agc acc     1392
Cys Arg Ile Lys Asn Val Leu Asp Glu Ile Leu Gln Met Tyr Ser Thr
            450                 455                 460 agc gag ctg aac gag atc ctg aag cac ctg atc gag ccc acc tgg gtc     1440
Ser Glu Leu Asn Glu Ile Leu Lys His Leu Ile Glu Pro Thr Trp Val
                465                 470                 475 gca acc ggg ctg gag atc gac ttc gag acc ctg gtg gca gga tgc gag     1488
Ala Thr Gly Leu Glu Ile Asp Phe Glu Thr Leu Val Ala Gly Cys Glu
480                 485                 490 atc gca agc agt aag atc ggt gag atc gtc agc ctg gac gat gag aac     1536
Ile Ala Ser Ser Lys Ile Gly Glu Ile Val Ser Leu Asp Asp Glu Asn
495                 500                 505                 510 gac cag aag atc aac agc ttc agc ttc atc cct cac gag ttc ttc gag     1584
Asp Gln Lys Ile Asn Ser Phe Ser Phe Ile Pro His Glu Phe Phe Glu
```

-continued

| | | | | | | | | | | | | | | | | |
|---|---|---|---|---|---|---|---|---|---|---|---|---|---|---|---|---|
| | | | 515 | | | | | 520 | | | | | 525 | | | |
| gac | atg | gag | agc | aag | tgg | aag | ggt | cgc | atc | aag | cgc | atc | cac | atc | gac | 1632 |
| Asp | Met | Glu | Ser | Lys | Trp | Lys | Gly | Arg | Ile | Lys | Arg | Ile | His | Ile | Asp | |
| | | | 530 | | | | | 535 | | | | | 540 | | | |
| gac | gtc | ttc | acc | gcc | gtg | gag | aag | gca | gcc | gag | gcc | ctg | cac | atc | gca | 1680 |
| Asp | Val | Phe | Thr | Ala | Val | Glu | Lys | Ala | Ala | Glu | Ala | Leu | His | Ile | Ala | |
| | | 545 | | | | | 550 | | | | | 555 | | | | |
| gtc | acc | gag | gac | ttc | gtc | cct | gtc | gtg | agc | cgc | atc | aag | gcc | atc | gtc | 1728 |
| Val | Thr | Glu | Asp | Phe | Val | Pro | Val | Val | Ser | Arg | Ile | Lys | Ala | Ile | Val | |
| | 560 | | | | | 565 | | | | | 570 | | | | | |
| gcc | cct | ctg | gga | ggt | ccc | aag | gga | gag | atc | agc | tac | gca | cgc | gag | cag | 1776 |
| Ala | Pro | Leu | Gly | Gly | Pro | Lys | Gly | Glu | Ile | Ser | Tyr | Ala | Arg | Glu | Gln | |
| 575 | | | | 580 | | | | | 585 | | | | | 590 | | |
| gag | gca | gtg | tgg | ttc | aag | ggc | aag | cgc | ttc | acc | ccg | aac | ctg | tgg | gca | 1824 |
| Glu | Ala | Val | Trp | Phe | Lys | Gly | Lys | Arg | Phe | Thr | Pro | Asn | Leu | Trp | Ala | |
| | | | | 595 | | | | | 600 | | | | | 605 | | |
| ggt | agc | cca | gga | gag | gag | cag | atc | aag | cag | ctg | cgc | cac | gct | ctg | gac | 1872 |
| Gly | Ser | Pro | Gly | Glu | Glu | Gln | Ile | Lys | Gln | Leu | Arg | His | Ala | Leu | Asp | |
| | | | 610 | | | | | 615 | | | | | 620 | | | |
| agc | aag | ggc | cgc | aag | gtc | ggg | gag | gag | tgg | ttc | acc | act | cca | aag | gtg | 1920 |
| Ser | Lys | Gly | Arg | Lys | Val | Gly | Glu | Glu | Trp | Phe | Thr | Thr | Pro | Lys | Val | |
| | | 625 | | | | | 630 | | | | | 635 | | | | |
| gag | gcc | gca | ctg | acc | cgc | tac | cac | gag | gca | aac | gcc | aag | gcc | aag | gag | 1968 |
| Glu | Ala | Ala | Leu | Thr | Arg | Tyr | His | Glu | Ala | Asn | Ala | Lys | Ala | Lys | Glu | |
| | 640 | | | | | 645 | | | | | 650 | | | | | |
| cgc | gtc | ctg | gag | atc | ctg | cgc | gga | ctg | gct | gcc | gag | ctg | cag | tac | agc | 2016 |
| Arg | Val | Leu | Glu | Ile | Leu | Arg | Gly | Leu | Ala | Ala | Glu | Leu | Gln | Tyr | Ser | |
| 655 | | | | 660 | | | | | 665 | | | | | 670 | | |
| atc | aac | atc | ctg | gtc | ttc | agc | tcc | atg | ctg | ctg | gtc | atc | gcc | aag | gcc | 2064 |
| Ile | Asn | Ile | Leu | Val | Phe | Ser | Ser | Met | Leu | Leu | Val | Ile | Ala | Lys | Ala | |
| | | | | 675 | | | | | 680 | | | | | 685 | | |
| ctg | ttc | gct | cac | gcc | agc | gag | ggg | aga | cgc | agg | cgc | tgg | gtc | ttc | ccc | 2112 |
| Leu | Phe | Ala | His | Ala | Ser | Glu | Gly | Arg | Arg | Arg | Arg | Trp | Val | Phe | Pro | |
| | | | 690 | | | | | 695 | | | | | 700 | | | |
| acc | ctg | gtc | gag | agc | cac | ggg | ttc | gag | gac | gtc | aag | agc | ctg | gac | aag | 2160 |
| Thr | Leu | Val | Glu | Ser | His | Gly | Phe | Glu | Asp | Val | Lys | Ser | Leu | Asp | Lys | |
| | | 705 | | | | | 710 | | | | | 715 | | | | |
| acc | cac | ggg | atg | aag | atc | agc | ggt | ctg | ctg | cca | tac | tgg | ttc | cac | atc | 2208 |
| Thr | His | Gly | Met | Lys | Ile | Ser | Gly | Leu | Leu | Pro | Tyr | Trp | Phe | His | Ile | |
| | 720 | | | | | 725 | | | | | 730 | | | | | |
| gcc | gag | ggt | gtc | gtg | cgc | aac | gac | gtg | gac | atg | cag | agc | ctg | ttc | ctg | 2256 |
| Ala | Glu | Gly | Val | Val | Arg | Asn | Asp | Val | Asp | Met | Gln | Ser | Leu | Phe | Leu | |
| 735 | | | | 740 | | | | | 745 | | | | | 750 | | |
| ctg | acc | gga | ccg | aac | ggc | ggt | ggg | aag | agc | agc | ttt | ctg | agg | agc | atc | 2304 |
| Leu | Thr | Gly | Pro | Asn | Gly | Gly | Gly | Lys | Ser | Ser | Phe | Leu | Arg | Ser | Ile | |
| | | | | 755 | | | | | 760 | | | | | 765 | | |
| tgc | gct | gcc | gca | ctg | ctt | ggg | atc | tgc | gga | ctg | atg | gtc | cct | gcc | gag | 2352 |
| Cys | Ala | Ala | Ala | Leu | Leu | Gly | Ile | Cys | Gly | Leu | Met | Val | Pro | Ala | Glu | |
| | | | 770 | | | | | 775 | | | | | 780 | | | |
| agc | gcc | ctg | atc | cct | tac | ttc | gac | agc | atc | acc | ctg | cac | atg | aag | agc | 2400 |
| Ser | Ala | Leu | Ile | Pro | Tyr | Phe | Asp | Ser | Ile | Thr | Leu | His | Met | Lys | Ser | |
| | | 785 | | | | | 790 | | | | | 795 | | | | |
| tac | gac | agc | cca | gcc | gac | aag | aag | agc | tcc | ttc | cag | gtc | gag | atg | agc | 2448 |
| Tyr | Asp | Ser | Pro | Ala | Asp | Lys | Lys | Ser | Ser | Phe | Gln | Val | Glu | Met | Ser | |
| | 800 | | | | | 805 | | | | | 810 | | | | | |
| gag | ctg | cgc | agc | atc | atc | ggc | gga | act | acc | aac | cgc | agc | ctg | gta | ctg | 2496 |
| Glu | Leu | Arg | Ser | Ile | Ile | Gly | Gly | Thr | Thr | Asn | Arg | Ser | Leu | Val | Leu | |
| 815 | | | | 820 | | | | | 825 | | | | | 830 | | |
| gtg | gac | gag | atc | tgc | cgc | gga | acc | gag | acc | gca | aag | ggg | acc | tgc | atc | 2544 |

|  |  | |
|---|---|---|
| Val Asp Glu Ile Cys Arg Gly Thr Glu Thr Ala Lys Gly Thr Cys Ile<br>                835                  840                  845 | | |
| gct ggc agc atc att gag acc ctg gac gga atc ggg tgc ctg ggc atc<br>Ala Gly Ser Ile Ile Glu Thr Leu Asp Gly Ile Gly Cys Leu Gly Ile<br>           850                  855                 860 | 2592 |
| gtc agc act cac ctg cac gga atc ttc act ctg ccc ctg aac aag aag<br>Val Ser Thr His Leu His Gly Ile Phe Thr Leu Pro Leu Asn Lys Lys<br>              865                  870                875 | 2640 |
| aac acc gtg cac aag gcc atg ggc acc aca agc atc gac gga cag atc<br>Asn Thr Val His Lys Ala Met Gly Thr Thr Ser Ile Asp Gly Gln Ile<br>        880                  885                890 | 2688 |
| atg cct acc tgg aag ctg acc gac gga gtc tgc aag gag agc ctg gcc<br>Met Pro Thr Trp Lys Leu Thr Asp Gly Val Cys Lys Glu Ser Leu Ala<br>895                  900                905                910 | 2736 |
| ttc gag acg gcc aag cgc gag gga atc cct gag cac atc gtc cgc aga<br>Phe Glu Thr Ala Lys Arg Glu Gly Ile Pro Glu His Ile Val Arg Arg<br>              915                  920                925 | 2784 |
| gcc gag tac ctg tac cag ttg gtc tac gcc aag gag atg ctg ttc gca<br>Ala Glu Tyr Leu Tyr Gln Leu Val Tyr Ala Lys Glu Met Leu Phe Ala<br>        930                  935                940 | 2832 |
| gag aac ttc cca aac gag gag aag ttc agc acc tgc atc aac gtg aac<br>Glu Asn Phe Pro Asn Glu Glu Lys Phe Ser Thr Cys Ile Asn Val Asn<br>              945                  950                955 | 2880 |
| aac ctg aac gga acc cac ctg cac agc aag cgc ttc ctg agc gga gcc<br>Asn Leu Asn Gly Thr His Leu His Ser Lys Arg Phe Leu Ser Gly Ala<br>        960                  965                970 | 2928 |
| aac cag atg gag gtc ctg cgc gag gag gtt gag cgc gct gtg acc gtg<br>Asn Gln Met Glu Val Leu Arg Glu Glu Val Glu Arg Ala Val Thr Val<br>975                  980                985                990 | 2976 |
| atc tgc cag gac cac atc aag gac ctg aag tgc aag aag atc gca ctg<br>Ile Cys Gln Asp His Ile Lys Asp Leu Lys Cys Lys Lys Ile Ala Leu<br>              995                 1000             1005 | 3024 |
| gag ctg acc gag atc aag tgc ctc atc att ggc acc agg gag ctg<br>Glu Leu Thr Glu Ile Lys Cys Leu Ile Ile Gly Thr Arg Glu Leu<br>              1010                 1015             1020 | 3069 |
| cca cct ccc agc gtc gtg ggt agc tca agc gtc tac gtg atg ttc<br>Pro Pro Pro Ser Val Val Gly Ser Ser Ser Val Tyr Val Met Phe<br>              1025                1030               1035 | 3114 |
| cgc cca gac aag aaa ctg tac gtc gga gag acc gac gat ctg gag<br>Arg Pro Asp Lys Lys Leu Tyr Val Gly Glu Thr Asp Asp Leu Glu<br>             1040                1045              1050 | 3159 |
| gga cgc gtg cga aga cac cga ctg aag gag gga atg cac gac gct<br>Gly Arg Val Arg Arg His Arg Leu Lys Glu Gly Met His Asp Ala<br>             1055                1060              1065 | 3204 |
| agc ttc ctg tac ttc ctg gtc cca ggc aag agc ctg gca tgc cag<br>Ser Phe Leu Tyr Phe Leu Val Pro Gly Lys Ser Leu Ala Cys Gln<br>             1070                1075              1080 | 3249 |
| ttc gag agc ctg ctg atc aac cag ctg agc ggt cag ggc ttc cag<br>Phe Glu Ser Leu Leu Ile Asn Gln Leu Ser Gly Gln Gly Phe Gln<br>             1085                1090              1095 | 3294 |
| ctg agc aac atc gct gac ggt aag cac cgc aac ttc ggc acc agc<br>Leu Ser Asn Ile Ala Asp Gly Lys His Arg Asn Phe Gly Thr Ser<br>             1100                1105              1110 | 3339 |
| aac ctg tac aca taa aatgagctct gtccaacagt ctcagggtta atgtctatgt<br>Asn Leu Tyr Thr<br>             1115 | 3394 |
| atcttaaata atgttgtcgg cgatcgttca acatttggc aataaagttt cttaagattg | 3454 |
| aatcctgttg ccggtcttgc gatgattatc atataatttc tgttgaatta cgttaagcat | 3514 |

```
gtaataatta acatgtaatg catgacgtta tttatgagat gggttttttat gattagagtc    3574 ccgcaattat acatttaata cgcgatagaa aacaaaatat agcgcgcaaa ctaggataaa    3634
ttatcgcgcg cggtgtcatc tatgttacta gatccctgca ggatatataa gcttaaaa     3692
```

<210> SEQ ID NO 18
<211> LENGTH: 64
<212> TYPE: PRT
<213> ORGANISM: Artificial Sequence
<220> FEATURE:
<223> OTHER INFORMATION: Synthetic Construct

<400> SEQUENCE: 18

```
Met Met Ile Thr Arg Gly Gly Ala Lys Ala Ala Lys Ser Leu Leu Val
1               5                   10                  15

Ala Ala Gly Pro Arg Leu Phe Ser Thr Val Arg Thr Val Ser Ser His
            20                  25                  30

Glu Ala Leu Ser Ala Ser His Ile Leu Lys Pro Gly Val Thr Ser Ala
        35                  40                  45

Trp Ile Trp Thr Arg Ala Pro Thr Ile Gly Gly Met Arg Phe Val Asp
    50                  55                  60
```

<210> SEQ ID NO 19
<211> LENGTH: 1051
<212> TYPE: PRT
<213> ORGANISM: Artificial Sequence
<220> FEATURE:
<223> OTHER INFORMATION: Synthetic Construct

<400> SEQUENCE: 19

```
Pro His Ile Leu Trp Trp Lys Glu Arg Leu Gln Met Cys Arg Lys Phe
1               5                   10                  15

Ser Thr Val Gln Leu Ile Glu Arg Leu Glu Phe Ser Asn Leu Leu Gly
            20                  25                  30

Leu Asn Ser Asn Leu Lys Asn Gly Ser Leu Lys Glu Gly Thr Leu Asn
        35                  40                  45

Trp Glu Met Leu Gln Phe Lys Ser Lys Phe Pro Arg Gln Val Leu Leu
    50                  55                  60

Cys Arg Val Gly Glu Phe Tyr Glu Ala Trp Gly Ile Asp Ala Cys Ile
65                  70                  75                  80

Leu Val Glu Tyr Val Gly Leu Asn Pro Ile Gly Gly Leu Arg Ser Asp
                85                  90                  95

Ser Ile Pro Arg Ala Ser Cys Pro Val Val Asn Leu Arg Gln Thr Leu
            100                 105                 110

Asp Asp Leu Thr Thr Asn Gly Tyr Ser Val Cys Ile Val Glu Glu Ala
        115                 120                 125

Gln Gly Pro Ser Gln Ala Arg Ser Arg Lys Arg Phe Ile Ser Gly
    130                 135                 140

His Ala His Pro Gly Asn Pro Tyr Val Tyr Gly Leu Ala Thr Val Asp
145                 150                 155                 160

His Asp Leu Asn Phe Pro Glu Pro Met Pro Val Val Gly Ile Ser His
                165                 170                 175

Ser Ala Arg Gly Tyr Cys Ile Asn Met Val Leu Glu Thr Met Lys Thr
            180                 185                 190

Tyr Ser Ser Glu Asp Cys Leu Thr Glu Glu Ala Val Val Thr Lys Leu
        195                 200                 205

Arg Thr Cys Gln Tyr His Tyr Leu Phe Leu His Thr Ser Leu Arg Arg
    210                 215                 220
```

```
Asn Ser Cys Gly Thr Cys Asn Trp Gly Glu Phe Gly Glu Gly Gly Leu
225                 230                 235                 240

Leu Trp Gly Glu Cys Ser Ser Arg His Phe Asp Trp Phe Asp Gly Asn
            245                 250                 255

Pro Val Ser Asp Leu Leu Ala Lys Val Lys Glu Leu Tyr Ser Ile Asp
        260                 265                 270

Asp Glu Val Thr Phe Arg Asn Thr Thr Val Ser Ser Gly His Arg Ala
    275                 280                 285

Arg Pro Leu Thr Leu Gly Thr Ser Thr Gln Ile Gly Ala Ile Pro Thr
290                 295                 300

Glu Gly Ile Pro Ser Leu Leu Lys Val Leu Leu Pro Ser Asn Cys Asn
305                 310                 315                 320

Gly Leu Pro Val Leu Tyr Ile Arg Glu Leu Leu Leu Asn Pro Pro Ser
                325                 330                 335

Tyr Glu Ile Ala Ser Lys Ile Gln Ala Thr Cys Lys Leu Met Ser Ser
            340                 345                 350

Val Thr Cys Ser Ile Pro Glu Phe Thr Cys Val Ser Ser Ala Lys Leu
        355                 360                 365

Val Lys Leu Leu Glu Trp Arg Glu Val Asn His Met Glu Phe Cys Arg
370                 375                 380

Ile Lys Asn Val Leu Asp Glu Ile Leu Gln Met Tyr Ser Thr Ser Glu
385                 390                 395                 400

Leu Asn Glu Ile Leu Lys His Leu Ile Glu Pro Thr Trp Val Ala Thr
                405                 410                 415

Gly Leu Glu Ile Asp Phe Glu Thr Leu Val Ala Gly Cys Glu Ile Ala
            420                 425                 430

Ser Ser Lys Ile Gly Glu Ile Val Ser Leu Asp Asp Glu Asn Asp Gln
        435                 440                 445

Lys Ile Asn Ser Phe Ser Phe Ile Pro His Glu Phe Phe Glu Asp Met
450                 455                 460

Glu Ser Lys Trp Lys Gly Arg Ile Lys Arg Ile His Ile Asp Asp Val
465                 470                 475                 480

Phe Thr Ala Val Glu Lys Ala Ala Glu Ala Leu His Ile Ala Val Thr
                485                 490                 495

Glu Asp Phe Val Pro Val Val Ser Arg Ile Lys Ala Ile Val Ala Pro
            500                 505                 510

Leu Gly Gly Pro Lys Gly Glu Ile Ser Tyr Ala Arg Glu Gln Glu Ala
        515                 520                 525

Val Trp Phe Lys Gly Lys Arg Phe Thr Pro Asn Leu Trp Ala Gly Ser
530                 535                 540

Pro Gly Glu Glu Gln Ile Lys Gln Leu Arg His Ala Leu Asp Ser Lys
545                 550                 555                 560

Gly Arg Lys Val Gly Glu Glu Trp Phe Thr Thr Pro Lys Val Glu Ala
                565                 570                 575

Ala Leu Thr Arg Tyr His Glu Ala Asn Ala Lys Ala Lys Glu Arg Val
            580                 585                 590

Leu Glu Ile Leu Arg Gly Leu Ala Ala Glu Leu Gln Tyr Ser Ile Asn
        595                 600                 605

Ile Leu Val Phe Ser Ser Met Leu Leu Val Ile Ala Lys Ala Leu Phe
610                 615                 620

Ala His Ala Ser Glu Gly Arg Arg Arg Trp Val Phe Pro Thr Leu
625                 630                 635                 640
```

```
Val Glu Ser His Gly Phe Glu Asp Val Lys Ser Leu Asp Lys Thr His
            645                 650                 655

Gly Met Lys Ile Ser Gly Leu Leu Pro Tyr Trp Phe His Ile Ala Glu
        660                 665                 670

Gly Val Val Arg Asn Asp Val Asp Met Gln Ser Leu Phe Leu Leu Thr
            675                 680                 685

Gly Pro Asn Gly Gly Lys Ser Ser Phe Leu Arg Ser Ile Cys Ala
    690                 695                 700

Ala Ala Leu Leu Gly Ile Cys Gly Leu Met Val Pro Ala Glu Ser Ala
705                 710                 715                 720

Leu Ile Pro Tyr Phe Asp Ser Ile Thr Leu His Met Lys Ser Tyr Asp
            725                 730                 735

Ser Pro Ala Asp Lys Lys Ser Ser Phe Gln Val Glu Met Ser Glu Leu
            740                 745                 750

Arg Ser Ile Ile Gly Thr Thr Asn Arg Ser Leu Val Leu Val Asp
            755                 760                 765

Glu Ile Cys Arg Gly Thr Glu Thr Ala Lys Gly Thr Cys Ile Ala Gly
    770                 775                 780

Ser Ile Glu Thr Leu Asp Gly Ile Gly Cys Leu Gly Ile Val Ser
785                 790                 795                 800

Thr His Leu His Gly Ile Phe Thr Leu Pro Leu Asn Lys Lys Asn Thr
            805                 810                 815

Val His Lys Ala Met Gly Thr Thr Ser Ile Asp Gly Gln Ile Met Pro
            820                 825                 830

Thr Trp Lys Leu Thr Asp Gly Val Cys Lys Glu Ser Leu Ala Phe Glu
    835                 840                 845

Thr Ala Lys Arg Glu Gly Ile Pro Glu His Ile Val Arg Arg Ala Glu
    850                 855                 860

Tyr Leu Tyr Gln Leu Val Tyr Ala Lys Glu Met Leu Phe Ala Glu Asn
865                 870                 875                 880

Phe Pro Asn Glu Glu Lys Phe Ser Thr Cys Ile Asn Val Asn Asn Leu
            885                 890                 895

Asn Gly Thr His Leu His Ser Lys Arg Phe Leu Ser Gly Ala Asn Gln
    900                 905                 910

Met Glu Val Leu Arg Glu Val Glu Arg Ala Val Thr Val Ile Cys
            915                 920                 925

Gln Asp His Ile Lys Asp Leu Lys Cys Lys Lys Ile Ala Leu Glu Leu
    930                 935                 940

Thr Glu Ile Lys Cys Leu Ile Ile Gly Thr Arg Glu Leu Pro Pro
945                 950                 955                 960

Ser Val Val Gly Ser Ser Val Tyr Val Met Phe Arg Pro Asp Lys
            965                 970                 975

Lys Leu Tyr Val Gly Glu Thr Asp Asp Leu Glu Gly Arg Val Arg Arg
            980                 985                 990

His Arg Leu Lys Glu Gly Met His Asp Ala Ser Phe Leu Tyr Phe Leu
    995                 1000                1005

Val Pro Gly Lys Ser Leu Ala Cys Gln Phe Glu Ser Leu Leu Ile
    1010                1015                1020

Asn Gln Leu Ser Gly Gln Gly Phe Gln Leu Ser Asn Ile Ala Asp
    1025                1030                1035

Gly Lys His Arg Asn Phe Gly Thr Ser Asn Leu Tyr Thr
    1040                1045                1050
```

```
<210> SEQ ID NO 20
<211> LENGTH: 556
<212> TYPE: DNA
<213> ORGANISM: Glycine max
<220> FEATURE:
<221> NAME/KEY: exon
<222> LOCATION: (1)..(556)
<223> OTHER INFORMATION: Soybean MSH1 Domain VI

<400> SEQUENCE: 20 atc agt tgg ttt atg cta agg aaa tgc ttt ttg cag aaa att tcc caa    48
Ile Ser Trp Phe Met Leu Arg Lys Cys Phe Leu Gln Lys Ile Ser Gln
1               5                   10                  15 atg aag aaa agt ttt cta cct gca tca atg tta ata att tga atg gaa    96
Met Lys Lys Ser Phe Leu Pro Ala Ser Met Leu Ile Ile     Met Glu
            20                  25                  30 cac atc ttc att caa aaa ggt tcc tat cag gag cta atc aaa tgg aag   144
His Ile Phe Ile Gln Lys Gly Ser Tyr Gln Glu Leu Ile Lys Trp Lys
        35                  40                  45 ttt tac gcg agg aag ttg aga gag ctg tca ctg tga ttt gcc agg atc   192
Phe Tyr Ala Arg Lys Leu Arg Glu Leu Ser Leu     Phe Ala Arg Ile
    50                  55                      60 ata taa agg acc taa aat gca aaa aga ttg cat tgg agc tta ctg aga   240
Ile     Arg Thr     Asn Ala Lys Arg Leu His Trp Ser Leu Leu Arg
        65                  70                  75 taa aat gtc tca taa ttg gta caa ggg agc tac cac ctc cat cgg ttg   288
    Asn Val Ser     Leu Val Gln Gly Ser Tyr His Leu His Arg Leu
            80                  85                  90 tag gtt ctt caa gcg tct atg tga tgt tca gac cag ata aga aac tct   336
    Val Leu Gln Ala Ser Met     Cys Ser Asp Gln Ile Arg Asn Ser
            95                      100 atg tag gag aga ctg atg atc tcg agg gac ggg tcc gaa gac atc gat   384
Met     Glu Arg Leu Met Ile Ser Arg Asp Gly Ser Glu Asp Ile Asp
105             110                 115 taa agg aag gaa tgc atg atg cat cat tcc ttt att ttc ttg tcc cag   432
    Arg Lys Glu Cys Met Met His His Ser Phe Ile Phe Leu Ser Gln
        120                 125                 130 gta aag gct tgg cat gcc aat ttg aat ctc tgc tca tca acc aac ttt   480
Val Lys Ala Trp His Ala Asn Leu Asn Leu Cys Ser Ser Thr Asn Phe
135             140                 145                 150 ctg gtc aag gct tcc aac tga gca ata tag ctg atg gta aac ata gga   528
Leu Val Lys Ala Ser Asn     Ala Ile     Leu Met Val Asn Ile Gly
                155                         160 att ttg gca ctt cca acc tgt ata cat a                             556
Ile Leu Ala Leu Pro Thr Cys Ile His
165                 170

<210> SEQ ID NO 21
<211> LENGTH: 3734
<212> TYPE: DNA
<213> ORGANISM: Artificial Sequence
<220> FEATURE:
<223> OTHER INFORMATION: synthetic potato MSH1 with an Arabidopsis AOX1
      mitochondrial targeting signal and a NOS 3' polyadenylaton signal
<220> FEATURE:
<221> NAME/KEY: 5'UTR
<222> LOCATION: (1)..(6)
<220> FEATURE:
<221> NAME/KEY: CDS
<222> LOCATION: (7)..(198)
<223> OTHER INFORMATION: Arabidopsis AOX1 targeting signal
<220> FEATURE:
<221> NAME/KEY: CDS
<222> LOCATION: (199)..(3396)
<223> OTHER INFORMATION: Potato MSH1 protein without its native
      targeting signal
```

```
<220> FEATURE:
<221> NAME/KEY: polyA_site
<222> LOCATION: (3397)..(3710)
<220> FEATURE:
<221> NAME/KEY: misc_feature
<222> LOCATION: (3711)..(3734)
<223> OTHER INFORMATION: 3' FLANKING Restriction sites

<400> SEQUENCE: 21 gtcgac atg atg ata act cgc ggt gga gcc aag gcg gcg aaa tcg ctg       48
       Met Met Ile Thr Arg Gly Gly Ala Lys Ala Ala Lys Ser Leu
       1               5                   10 tta gtg gcg gct gga cca cgt ttg ttc tcg acg gtc cgt acg gtt tcg      96
Leu Val Ala Ala Gly Pro Arg Leu Phe Ser Thr Val Arg Thr Val Ser
15                  20                  25                  30 tct cac gag gct tta tca gca agc cat att ttg aag cct ggt gtt aca     144
Ser His Glu Ala Leu Ser Ala Ser His Ile Leu Lys Pro Gly Val Thr
                35                  40                  45 tct gct tgg ata tgg act aga gct ccg acg att gga ggt atg aga ttc     192
Ser Ala Trp Ile Trp Thr Arg Ala Pro Thr Ile Gly Gly Met Arg Phe
    50                  55                  60 gtg gac gtc aac atc atg tgg tgg aag gag cgc atg gag ttc ctg cgc     240
Val Asp Val Asn Ile Met Trp Trp Lys Glu Arg Met Glu Phe Leu Arg
65                  70                  75 aag cct agc tct gtc ctg ctg gcc aag cgc ctg acc tac tgc aac ctg     288
Lys Pro Ser Ser Val Leu Leu Ala Lys Arg Leu Thr Tyr Cys Asn Leu
80                  85                  90 ctg ggt gtg gac ccg agc ctg cgc aac ggc agc ctg aag gag gga acc     336
Leu Gly Val Asp Pro Ser Leu Arg Asn Gly Ser Leu Lys Glu Gly Thr
95                  100                 105                 110 ctg aac agc gag atg ctc cag ttc aag agc aag ttc cca cgc gag gtc     384
Leu Asn Ser Glu Met Leu Gln Phe Lys Ser Lys Phe Pro Arg Glu Val
                115                 120                 125 ctc ctc tgc cgc gtc gga gac ttc tac gag gcc atc gga ttc gac gcc     432
Leu Leu Cys Arg Val Gly Asp Phe Tyr Glu Ala Ile Gly Phe Asp Ala
            130                 135                 140 tgc atc ctg gtg gag tac gct ggt ctg aac cca ttc ggt ggc ctc cgc     480
Cys Ile Leu Val Glu Tyr Ala Gly Leu Asn Pro Phe Gly Gly Leu Arg
145                 150                 155 agc gac agc atc cca aag gcc ggt tgc cca gtc gtg aac ctg cgc cag     528
Ser Asp Ser Ile Pro Lys Ala Gly Cys Pro Val Val Asn Leu Arg Gln
160                 165                 170 acg ctg gac gac ctg acc cgt aac ggc ttc agc gtc tgc gtg gtc gag     576
Thr Leu Asp Asp Leu Thr Arg Asn Gly Phe Ser Val Cys Val Val Glu
175                 180                 185                 190 gag gtc cag ggt ccc acc cag gct cgc gct cgc aag agc cgc ttc atc     624
Glu Val Gln Gly Pro Thr Gln Ala Arg Ala Arg Lys Ser Arg Phe Ile
                195                 200                 205 agc ggc cac gcc cac ccg ggc agc ccc tac gtc ttc ggc ctg gtg gga     672
Ser Gly His Ala His Pro Gly Ser Pro Tyr Val Phe Gly Leu Val Gly
            210                 215                 220 gac gac cag gac ctg gac ttc cca gag ccg atg ccc gtc gtg ggc atc     720
Asp Asp Gln Asp Leu Asp Phe Pro Glu Pro Met Pro Val Val Gly Ile
225                 230                 235 agc cgc agc gcc aag ggg tac tgc atc atc agc gtg tac gag acc atg     768
Ser Arg Ser Ala Lys Gly Tyr Cys Ile Ile Ser Val Tyr Glu Thr Met
240                 245                 250 aag acc tac agc gtc gag gac ggc ctg acc gag gaa gcg gtc gtg acc     816
Lys Thr Tyr Ser Val Glu Asp Gly Leu Thr Glu Glu Ala Val Val Thr
255                 260                 265                 270 aag ctg cgc acc tgc cgc tgc cac cac ctg ttc ctg cac aac agc ctg     864
```

```
                Lys Leu Arg Thr Cys Arg Cys His His Leu Phe Leu His Asn Ser Leu
                                275                 280                 285 aag aac aac agc agc ggc acc agc cgc tgg gga gag ttc ggt gag ggt            912
Lys Asn Asn Ser Ser Gly Thr Ser Arg Trp Gly Glu Phe Gly Glu Gly
            290                 295                 300 ggc ctg ctg tgg ggc gag tgc aac gcg aga cag cag gag tgg ctg gac            960
Gly Leu Leu Trp Gly Glu Cys Asn Ala Arg Gln Gln Glu Trp Leu Asp
        305                 310                 315 ggc aac ccg atc gac gag ctg ctg ttc aag gtc aag gag ctg tac ggt           1008
Gly Asn Pro Ile Asp Glu Leu Leu Phe Lys Val Lys Glu Leu Tyr Gly
    320                 325                 330 ctg gac gac gac atc cca ttc cgc aac gtg acc gtg gtc agc gag aac           1056
Leu Asp Asp Asp Ile Pro Phe Arg Asn Val Thr Val Val Ser Glu Asn
335                 340                 345                 350 agg ccc cgc cct ctg cac ctg gga acc gcc acc cag atc ggt gcc atc           1104
Arg Pro Arg Pro Leu His Leu Gly Thr Ala Thr Gln Ile Gly Ala Ile
                355                 360                 365 cca acc gag ggc atc cca tgc ctg ctg aag gtc ctg ctg cct cca cac           1152
Pro Thr Glu Gly Ile Pro Cys Leu Leu Lys Val Leu Leu Pro Pro His
            370                 375                 380 tgc agc ggt ctg cca gcg ctg tac atc cgc gac ctg ctc ctg aac cca           1200
Cys Ser Gly Leu Pro Ala Leu Tyr Ile Arg Asp Leu Leu Leu Asn Pro
        385                 390                 395 cca gcg tac gag atc agc tca gac atc cag gag gcc tgc cgc ctg atg           1248
Pro Ala Tyr Glu Ile Ser Ser Asp Ile Gln Glu Ala Cys Arg Leu Met
    400                 405                 410 atg agc gtg acc tgc agc atc cct gac ttc acc tgc atc agc tct gcc           1296
Met Ser Val Thr Cys Ser Ile Pro Asp Phe Thr Cys Ile Ser Ser Ala
415                 420                 425                 430 aag ctg gtg aag ctg ctc gag ctg cgc gag gcc aac cac gtg gag ttc           1344
Lys Leu Val Lys Leu Leu Glu Leu Arg Glu Ala Asn His Val Glu Phe
                435                 440                 445 tgc aag atc aag agc atg gtg gag gag atc ctg cag ctg tac cgc aac           1392
Cys Lys Ile Lys Ser Met Val Glu Glu Ile Leu Gln Leu Tyr Arg Asn
            450                 455                 460 agc gag ctg cgc gcc atc gtc gag ctg ctg atg gac cct acc tgg gtc           1440
Ser Glu Leu Arg Ala Ile Val Glu Leu Leu Met Asp Pro Thr Trp Val
        465                 470                 475 gca acc ggg ctg aag gtg gac ttc gac acc ctg gtc aac gag tgc ggc           1488
Ala Thr Gly Leu Lys Val Asp Phe Asp Thr Leu Val Asn Glu Cys Gly
    480                 485                 490 aag atc agc tgc cgc atc agc gag atc atc agc gtg cac ggt gag cgc           1536
Lys Ile Ser Cys Arg Ile Ser Glu Ile Ile Ser Val His Gly Glu Arg
495                 500                 505                 510 gac cag aag gtc agc tcc tac ccc atc atc ccc aac gac ttc ttc gag           1584
Asp Gln Lys Val Ser Ser Tyr Pro Ile Ile Pro Asn Asp Phe Phe Glu
                515                 520                 525 gac atg gag ctg ctg tgg aag ggc cgc gtg aag cgc atc cac ctg gag           1632
Asp Met Glu Leu Leu Trp Lys Gly Arg Val Lys Arg Ile His Leu Glu
            530                 535                 540 gag gcc tac gcc gag gtc gag aag gcc gca gac gcc ctg agc ctg gcc           1680
Glu Ala Tyr Ala Glu Val Glu Lys Ala Ala Asp Ala Leu Ser Leu Ala
        545                 550                 555 atc acc gag gac ttc ctg ccc atc atc agc cgc atc agt gcg acc atg           1728
Ile Thr Glu Asp Phe Leu Pro Ile Ile Ser Arg Ile Ser Ala Thr Met
    560                 565                 570 gcg ccc ctg gga ggc acc aaa ggg gag atc ctg tac gcc cga gag cac           1776
Ala Pro Leu Gly Gly Thr Lys Gly Glu Ile Leu Tyr Ala Arg Glu His
575                 580                 585                 590
```

-continued

| | |
|---|---|
| ggc gct gtc tgg ttc aag ggc aag cgc ttc gtc cca acc gtg tgg gcc<br>Gly Ala Val Trp Phe Lys Gly Lys Arg Phe Val Pro Thr Val Trp Ala<br>595         600         605 | 1824 |
| gga acc gcc gga gag gag cag atc aag cac ctg aag ccc gct ctg gat<br>Gly Thr Ala Gly Glu Glu Gln Ile Lys His Leu Lys Pro Ala Leu Asp<br>610         615         620 | 1872 |
| agc aag ggg aag aag gtc ggc gag gag tgg ttc acc acc atg cgc gtg<br>Ser Lys Gly Lys Lys Val Gly Glu Glu Trp Phe Thr Thr Met Arg Val<br>625         630         635 | 1920 |
| gag gac gca atc gcc agg tac cac gag gcc agc gcc aag gcc aag agc<br>Glu Asp Ala Ile Ala Arg Tyr His Glu Ala Ser Ala Lys Ala Lys Ser<br>640         645         650 | 1968 |
| cgc gtc ctg gag ctg ctg agg ggc ctg agc tca gag ctg ctg agc aag<br>Arg Val Leu Glu Leu Leu Arg Gly Leu Ser Ser Glu Leu Leu Ser Lys<br>655         660         665         670 | 2016 |
| atc aac atc ctg atc ttc gcc agc gtg ctg aac gtg atc gcc aag agc<br>Ile Asn Ile Leu Ile Phe Ala Ser Val Leu Asn Val Ile Ala Lys Ser<br>675         680         685 | 2064 |
| ctg ttc agc cac gtg agc gag ggg aga cgc aga aac tgg atc ttc ccc<br>Leu Phe Ser His Val Ser Glu Gly Arg Arg Arg Asn Trp Ile Phe Pro<br>690         695         700 | 2112 |
| acc atc acc cag ttc aac aag tgc cag gac acc gag gcc ctg aac gga<br>Thr Ile Thr Gln Phe Asn Lys Cys Gln Asp Thr Glu Ala Leu Asn Gly<br>705         710         715 | 2160 |
| acc gag ggc atg aag atc atc ggt ctg agc cct tac tgg ttc gac gca<br>Thr Glu Gly Met Lys Ile Ile Gly Leu Ser Pro Tyr Trp Phe Asp Ala<br>720         725         730 | 2208 |
| gcc cgc ggg acc ggt gtc cag aac acc gtg gac atg cag agc atg ttc<br>Ala Arg Gly Thr Gly Val Gln Asn Thr Val Asp Met Gln Ser Met Phe<br>735         740         745         750 | 2256 |
| ctg ctg acc ggt ccc aac ggt ggg ggc aag agc agc ctg ctg cgc agc<br>Leu Leu Thr Gly Pro Asn Gly Gly Gly Lys Ser Ser Leu Leu Arg Ser<br>755         760         765 | 2304 |
| ctg tgc gca gcc gca ctg ctg ggc atg tgc ggg ttc atg gtg ccc gct<br>Leu Cys Ala Ala Ala Leu Leu Gly Met Cys Gly Phe Met Val Pro Ala<br>770         775         780 | 2352 |
| gag agc gcc gtc atc cct cac ttc gac agc atc atg ctg cac atg aag<br>Glu Ser Ala Val Ile Pro His Phe Asp Ser Ile Met Leu His Met Lys<br>785         790         795 | 2400 |
| agc tac gac agc cct gcc gac ggc aag agc agc ttc cag atc gag atg<br>Ser Tyr Asp Ser Pro Ala Asp Gly Lys Ser Ser Phe Gln Ile Glu Met<br>800         805         810 | 2448 |
| agc gag atc cgc agc ctg atc acc ggt gcc acc agc agt agc ctg gtc<br>Ser Glu Ile Arg Ser Leu Ile Thr Gly Ala Thr Ser Ser Ser Leu Val<br>815         820         825         830 | 2496 |
| ctg atc gac gag atc tgc cgc gga acc gag acc gcc aag ggg acc tgc<br>Leu Ile Asp Glu Ile Cys Arg Gly Thr Glu Thr Ala Lys Gly Thr Cys<br>835         840         845 | 2544 |
| atc gcc gga agc gtg atc gag acc ctc gac gcc atc ggg tgc ctg gga<br>Ile Ala Gly Ser Val Ile Glu Thr Leu Asp Ala Ile Gly Cys Leu Gly<br>850         855         860 | 2592 |
| atc gtc agc acc cac ctg cac ggc atc ttc gac ctg ccc ctg aag atc<br>Ile Val Ser Thr His Leu His Gly Ile Phe Asp Leu Pro Leu Lys Ile<br>865         870         875 | 2640 |
| aag aag acc gtc tac aag gcc atg gga gcc gag tac gtg gac ggc cag<br>Lys Lys Thr Val Tyr Lys Ala Met Gly Ala Glu Tyr Val Asp Gly Gln<br>880         885         890 | 2688 |
| ccc atc cca acc tgg aag ctg atc gac ggg gtg tgc aag gag agc ctg<br>Pro Ile Pro Thr Trp Lys Leu Ile Asp Gly Val Cys Lys Glu Ser Leu<br>895         900         905         910 | 2736 |

-continued

```
gca ttc gag acc gcc cag cgc gag gga atc cca gag atc ctg atc cag    2784
Ala Phe Glu Thr Ala Gln Arg Glu Gly Ile Pro Glu Ile Leu Ile Gln
            915                 920                 925 cgc gca gag gag ctg tac aac agc gcc tac ggg aac cag atc cca atg    2832
Arg Ala Glu Glu Leu Tyr Asn Ser Ala Tyr Gly Asn Gln Ile Pro Met
            930                 935                 940 aag aag gac cag atc cgc cct ctg tgc agc gac atc gac ctg aac agc    2880
Lys Lys Asp Gln Ile Arg Pro Leu Cys Ser Asp Ile Asp Leu Asn Ser
            945                 950                 955 acc gac aag agc agc gac cag ctg aac ggc acc cgc ctg atc gcc ctg    2928
Thr Asp Lys Ser Ser Asp Gln Leu Asn Gly Thr Arg Leu Ile Ala Leu
            960                 965                 970 gac agc agc acc aag ctg atg cac cgc atg ggc atc agc agc aag aag    2976
Asp Ser Ser Thr Lys Leu Met His Arg Met Gly Ile Ser Ser Lys Lys
975                 980                 985                 990 ctg gag gac gcc atc tgc ctg atc tgc gag  aag aag ctg atc gag  ctg  3024
Leu Glu Asp Ala Ile Cys Leu Ile Cys Glu  Lys Lys Leu Ile Glu  Leu
                    995                 1000                1005 tac aag atg aag  aac ccg agc gag atg  gcc atg gtc aac tgt  gtg       3069
Tyr Lys Met Lys  Asn Pro Ser Glu Met  Ala Met Val Asn Cys  Val
                 1010                1015                1020 ctg atc gct gcc  cgc gag cag ccg gct  ccc agc acc atc ggt  gcc       3114
Leu Ile Ala Ala  Arg Glu Gln Pro Ala  Pro Ser Thr Ile Gly  Ala
                 1025                1030                1035 agc agc gtg tac  acc atg ctg aga ccc  gac aag aag ctg tac  gtc       3159
Ser Ser Val Tyr  Thr Met Leu Arg Pro  Asp Lys Lys Leu Tyr  Val
                 1040                1045                1050 gga cag acc gac  gac ctg gag ggc aga  gtg cgc gct cac cgc  ctg       3204
Gly Gln Thr Asp  Asp Leu Glu Gly Arg  Val Arg Ala His Arg  Leu
                 1055                1060                1065 aag gag ggc atg  gag aac gcg agc ttc  ctg tac ttc ctg gtc  agc       3249
Lys Glu Gly Met  Glu Asn Ala Ser Phe  Leu Tyr Phe Leu Val  Ser
                 1070                1075                1080 ggg aag agc atc  gcg tgc cag ctg gag  acc ctg ctg atc aac  cag       3294
Gly Lys Ser Ile  Ala Cys Gln Leu Glu  Thr Leu Leu Ile Asn  Gln
                 1085                1090                1095 ctg cct aac tac  ggc ttc cag ctg acc  aac gtg gcc gac ggt  aag       3339
Leu Pro Asn Tyr  Gly Phe Gln Leu Thr  Asn Val Ala Asp Gly  Lys
                 1100                1105                1110 cac cgc aac ttc  ggc acc acc aac ctg  agc cca gag cct agc  acc       3384
His Arg Asn Phe  Gly Thr Thr Asn Leu  Ser Pro Glu Pro Ser  Thr
                 1115                1120                1125 gcc ctg cgc tga aatgagctct gtccaacagt ctcagggtta atgtctatgt         3436
Ala Leu Arg atcttaaata atgttgtcgg cgatcgttca acatttggc aataaagttt cttaagattg    3496
aatcctgttg ccggtcttgc gatgattatc atataatttc tgttgaatta cgttaagcat   3556
gtaataatta acatgtaatg catgacgtta tttatgagat gggtttttat gattagagtc   3616
ccgcaattat acatttaata cgcgatagaa aacaaaatat agcgcgcaaa ctaggataaa   3676
ttatcgcgcg cggtgtcatc tatgttacta gatccctgca ggatatataa gcttaaaa    3734
```

<210> SEQ ID NO 22
<211> LENGTH: 64
<212> TYPE: PRT
<213> ORGANISM: Artificial Sequence
<220> FEATURE:
<223> OTHER INFORMATION: Synthetic Construct

<400> SEQUENCE: 22

```
Met Met Ile Thr Arg Gly Gly Ala Lys Ala Lys Ser Leu Leu Val
1               5                   10                  15

Ala Ala Gly Pro Arg Leu Phe Ser Thr Val Arg Thr Val Ser Ser His
                20                  25                  30

Glu Ala Leu Ser Ala Ser His Ile Leu Lys Pro Gly Val Thr Ser Ala
                35                  40                  45

Trp Ile Trp Thr Arg Ala Pro Thr Ile Gly Gly Met Arg Phe Val Asp
    50                  55                  60
```

<210> SEQ ID NO 23
<211> LENGTH: 1065
<212> TYPE: PRT
<213> ORGANISM: Artificial Sequence
<220> FEATURE:
<223> OTHER INFORMATION: Synthetic Construct

<400> SEQUENCE: 23

```
Val Asn Ile Met Trp Trp Lys Glu Arg Met Glu Phe Leu Arg Lys Pro
1               5                   10                  15

Ser Ser Val Leu Leu Ala Lys Arg Leu Thr Tyr Cys Asn Leu Leu Gly
                20                  25                  30

Val Asp Pro Ser Leu Arg Asn Gly Ser Leu Lys Glu Gly Thr Leu Asn
                35                  40                  45

Ser Glu Met Leu Gln Phe Lys Ser Lys Phe Pro Arg Glu Val Leu Leu
                50                  55                  60

Cys Arg Val Gly Asp Phe Tyr Glu Ala Ile Gly Phe Asp Ala Cys Ile
65                  70                  75                  80

Leu Val Glu Tyr Ala Gly Leu Asn Pro Phe Gly Gly Leu Arg Ser Asp
                85                  90                  95

Ser Ile Pro Lys Ala Gly Cys Pro Val Val Asn Leu Arg Gln Thr Leu
                100                 105                 110

Asp Asp Leu Thr Arg Asn Gly Phe Ser Val Cys Val Val Glu Glu Val
                115                 120                 125

Gln Gly Pro Thr Gln Ala Arg Ala Arg Lys Ser Arg Phe Ile Ser Gly
                130                 135                 140

His Ala His Pro Gly Ser Pro Tyr Val Phe Gly Leu Val Gly Asp Asp
145                 150                 155                 160

Gln Asp Leu Asp Phe Pro Glu Pro Met Pro Val Val Gly Ile Ser Arg
                165                 170                 175

Ser Ala Lys Gly Tyr Cys Ile Ile Ser Val Tyr Glu Thr Met Lys Thr
                180                 185                 190

Tyr Ser Val Glu Asp Gly Leu Thr Glu Glu Ala Val Val Thr Lys Leu
                195                 200                 205

Arg Thr Cys Arg Cys His Leu Phe Leu His Asn Ser Leu Lys Asn
                210                 215                 220

Asn Ser Ser Gly Thr Ser Arg Trp Gly Glu Phe Gly Glu Gly Leu
225                 230                 235                 240

Leu Trp Gly Glu Cys Asn Ala Arg Gln Gln Glu Trp Leu Asp Gly Asn
                245                 250                 255

Pro Ile Asp Glu Leu Leu Phe Lys Val Lys Glu Leu Tyr Gly Leu Asp
                260                 265                 270

Asp Asp Ile Pro Phe Arg Asn Val Thr Val Val Ser Glu Asn Arg Pro
                275                 280                 285

Arg Pro Leu His Leu Gly Thr Ala Thr Gln Ile Gly Ala Ile Pro Thr
                290                 295                 300
```

```
Glu Gly Ile Pro Cys Leu Leu Lys Val Leu Leu Pro Pro His Cys Ser
305                 310                 315                 320

Gly Leu Pro Ala Leu Tyr Ile Arg Asp Leu Leu Leu Asn Pro Pro Ala
                325                 330                 335

Tyr Glu Ile Ser Ser Asp Ile Gln Glu Ala Cys Arg Leu Met Met Ser
                340                 345                 350

Val Thr Cys Ser Ile Pro Asp Phe Thr Cys Ile Ser Ser Ala Lys Leu
            355                 360                 365

Val Lys Leu Leu Glu Leu Arg Glu Ala Asn His Val Glu Phe Cys Lys
        370                 375                 380

Ile Lys Ser Met Val Glu Ile Leu Gln Leu Tyr Arg Asn Ser Glu
385                 390                 395                 400

Leu Arg Ala Ile Val Glu Leu Leu Met Asp Pro Thr Trp Val Ala Thr
                405                 410                 415

Gly Leu Lys Val Asp Phe Asp Thr Leu Val Asn Glu Cys Gly Lys Ile
            420                 425                 430

Ser Cys Arg Ile Ser Glu Ile Ile Ser Val His Gly Glu Arg Asp Gln
        435                 440                 445

Lys Val Ser Ser Tyr Pro Ile Ile Pro Asn Asp Phe Phe Glu Asp Met
450                 455                 460

Glu Leu Leu Trp Lys Gly Arg Val Lys Arg Ile His Leu Glu Glu Ala
465                 470                 475                 480

Tyr Ala Glu Val Glu Lys Ala Ala Asp Ala Leu Ser Leu Ala Ile Thr
                485                 490                 495

Glu Asp Phe Leu Pro Ile Ile Ser Arg Ile Ser Ala Thr Met Ala Pro
                500                 505                 510

Leu Gly Gly Thr Lys Gly Glu Ile Leu Tyr Ala Arg Glu His Gly Ala
            515                 520                 525

Val Trp Phe Lys Gly Lys Arg Phe Val Pro Thr Val Trp Ala Gly Thr
            530                 535                 540

Ala Gly Glu Glu Gln Ile Lys His Leu Lys Pro Ala Leu Asp Ser Lys
545                 550                 555                 560

Gly Lys Lys Val Gly Glu Glu Trp Phe Thr Thr Met Arg Val Glu Asp
                565                 570                 575

Ala Ile Ala Arg Tyr His Glu Ala Ser Ala Lys Ala Lys Ser Arg Val
            580                 585                 590

Leu Glu Leu Leu Arg Gly Leu Ser Ser Glu Leu Leu Ser Lys Ile Asn
        595                 600                 605

Ile Leu Ile Phe Ala Ser Val Leu Asn Val Ile Ala Lys Ser Leu Phe
            610                 615                 620

Ser His Val Ser Glu Gly Arg Arg Arg Asn Trp Ile Phe Pro Thr Ile
625                 630                 635                 640

Thr Gln Phe Asn Lys Cys Gln Asp Thr Glu Ala Leu Asn Gly Thr Glu
                645                 650                 655

Gly Met Lys Ile Ile Gly Leu Ser Pro Tyr Trp Phe Asp Ala Ala Arg
            660                 665                 670

Gly Thr Gly Val Gln Asn Thr Val Asp Met Gln Ser Met Phe Leu Leu
            675                 680                 685

Thr Gly Pro Asn Gly Gly Lys Ser Ser Leu Leu Arg Ser Leu Cys
        690                 695                 700

Ala Ala Ala Leu Leu Gly Met Cys Gly Phe Met Val Pro Ala Glu Ser
705                 710                 715                 720
```

Ala Val Ile Pro His Phe Asp Ser Ile Met Leu His Met Lys Ser Tyr
                725                 730                 735

Asp Ser Pro Ala Asp Gly Lys Ser Ser Phe Gln Ile Glu Met Ser Glu
            740                 745                 750

Ile Arg Ser Leu Ile Thr Gly Ala Thr Ser Ser Leu Val Leu Ile
        755                 760                 765

Asp Glu Ile Cys Arg Gly Thr Glu Thr Ala Lys Gly Thr Cys Ile Ala
    770                 775                 780

Gly Ser Val Ile Glu Thr Leu Asp Ala Ile Gly Cys Leu Gly Ile Val
785                 790                 795                 800

Ser Thr His Leu His Gly Ile Phe Asp Leu Pro Leu Lys Ile Lys Lys
                805                 810                 815

Thr Val Tyr Lys Ala Met Gly Ala Glu Tyr Val Asp Gly Gln Pro Ile
            820                 825                 830

Pro Thr Trp Lys Leu Ile Asp Gly Val Cys Lys Glu Ser Leu Ala Phe
        835                 840                 845

Glu Thr Ala Gln Arg Gly Ile Pro Glu Ile Leu Ile Gln Arg Ala
    850                 855                 860

Glu Glu Leu Tyr Asn Ser Ala Tyr Gly Asn Gln Ile Pro Met Lys Lys
865                 870                 875                 880

Asp Gln Ile Arg Pro Leu Cys Ser Asp Ile Asp Leu Asn Ser Thr Asp
                885                 890                 895

Lys Ser Ser Asp Gln Leu Asn Gly Thr Arg Leu Ile Ala Leu Asp Ser
            900                 905                 910

Ser Thr Lys Leu Met His Arg Met Gly Ile Ser Ser Lys Lys Leu Glu
        915                 920                 925

Asp Ala Ile Cys Leu Ile Cys Glu Lys Lys Leu Ile Glu Leu Tyr Lys
    930                 935                 940

Met Lys Asn Pro Ser Glu Met Ala Met Val Asn Cys Val Leu Ile Ala
945                 950                 955                 960

Ala Arg Glu Gln Pro Ala Pro Ser Thr Ile Gly Ala Ser Ser Val Tyr
                965                 970                 975

Thr Met Leu Arg Pro Asp Lys Lys Leu Tyr Val Gly Gln Thr Asp Asp
            980                 985                 990

Leu Glu Gly Arg Val Arg Ala His Arg Leu Lys Glu Gly Met Glu Asn
        995                 1000                1005

Ala Ser Phe Leu Tyr Phe Leu Val Ser Gly Lys Ser Ile Ala Cys
    1010                1015                1020

Gln Leu Glu Thr Leu Leu Ile Asn Gln Leu Pro Asn Tyr Gly Phe
    1025                1030                1035

Gln Leu Thr Asn Val Ala Asp Gly Lys His Arg Asn Phe Gly Thr
    1040                1045                1050

Thr Asn Leu Ser Pro Glu Pro Ser Thr Ala Leu Arg
    1055                1060                1065

<210> SEQ ID NO 24
<211> LENGTH: 656
<212> TYPE: DNA
<213> ORGANISM: Lycopersicon esculentum
<220> FEATURE:
<221> NAME/KEY: exon
<222> LOCATION: (1)..(656)
<223> OTHER INFORMATION: Tomato MSH1 Domain VI

<400> SEQUENCE: 24 agg tat cac gag gca agt gct aag gca aag tca agg gtc ttg gaa ttg      48

```
                Arg Tyr His Glu Ala Ser Ala Lys Ala Lys Ser Arg Val Leu Glu Leu
                1               5                   10                  15 cta agg gga ctt tct tct gaa tta cta tct aag atc aat atc ctt atc          96
Leu Arg Gly Leu Ser Ser Glu Leu Leu Ser Lys Ile Asn Ile Leu Ile
            20                  25                  30 ttt gca tct gtc ttg aat gtg ata gca aaa tca tta ttt tct cat gtg         144
Phe Ala Ser Val Leu Asn Val Ile Ala Lys Ser Leu Phe Ser His Val
        35                  40                  45 agt gaa gga aga aga aga aat tgg att ttc cca aca atc aca caa ttt         192
Ser Glu Gly Arg Arg Arg Asn Trp Ile Phe Pro Thr Ile Thr Gln Phe
    50                  55                  60 aac aaa tgt cag gac aca gag gca ctt aat gga act gat gga atg aag         240
Asn Lys Cys Gln Asp Thr Glu Ala Leu Asn Gly Thr Asp Gly Met Lys
65                  70                  75                  80 ata att ggt cta tct cct tat tgg ttt gat gca gca cga ggg act ggt         288
Ile Ile Gly Leu Ser Pro Tyr Trp Phe Asp Ala Ala Arg Gly Thr Gly
                85                  90                  95 gta cag aat aca gta gat atg cag tcc atg ttt ctt tta aca ggt cca         336
Val Gln Asn Thr Val Asp Met Gln Ser Met Phe Leu Leu Thr Gly Pro
            100                 105                 110 aat ggt ggg ggc aaa tca agc ctg ctg cgt tcg ttg tgt gca gct gca         384
Asn Gly Gly Gly Lys Ser Ser Leu Leu Arg Ser Leu Cys Ala Ala Ala
        115                 120                 125 ttg cta gga atg tgt ggg ttc atg gtt cca gct gaa tca gct gtc att         432
Leu Leu Gly Met Cys Gly Phe Met Val Pro Ala Glu Ser Ala Val Ile
    130                 135                 140 cct cat ttt gac tca att atg ctg cat atg aaa tca tat gat agt cct         480
Pro His Phe Asp Ser Ile Met Leu His Met Lys Ser Tyr Asp Ser Pro
145                 150                 155                 160 gtt gat gga aaa agt tca ttt cag att gaa atg tct gaa att cgg tct         528
Val Asp Gly Lys Ser Ser Phe Gln Ile Glu Met Ser Glu Ile Arg Ser
                165                 170                 175 ctg att act ggt gcc act tca aga agt ctt gta ctt ata gat gaa ata         576
Leu Ile Thr Gly Ala Thr Ser Arg Ser Leu Val Leu Ile Asp Glu Ile
            180                 185                 190 tgt cga gga aca gaa aca gca aaa ggg aca tgt att gct gga agt gtc         624
Cys Arg Gly Thr Glu Thr Ala Lys Gly Thr Cys Ile Ala Gly Ser Val
        195                 200                 205 ata gaa acc ctg gac gaa att ggc tgt ttg gg                              656
Ile Glu Thr Leu Asp Glu Ile Gly Cys Leu
    210                 215

<210> SEQ ID NO 25
<211> LENGTH: 21
<212> TYPE: DNA
<213> ORGANISM: Arabidopsis thaliana
<220> FEATURE:
<221> NAME/KEY: misc_feature
<222> LOCATION: (1)..(21)

<400> SEQUENCE: 25
acggaaaaag ttctttccag g                                                  21

<210> SEQ ID NO 26
<211> LENGTH: 21
<212> TYPE: DNA
<213> ORGANISM: Arabidopsis thaliana
<220> FEATURE:
<221> NAME/KEY: misc_feature
<222> LOCATION: (1)..(21)
<223> OTHER INFORMATION: Msh1 primer

<400> SEQUENCE: 26
```

```
gctttccatc ggctaggtta g                                              21

<210> SEQ ID NO 27
<211> LENGTH: 34
<212> TYPE: DNA
<213> ORGANISM: Agrobacterium tumefaciens
<220> FEATURE:
<221> NAME/KEY: misc_feature
<222> LOCATION: (1)..(34)
<223> OTHER INFORMATION: Sail primer LB3

<400> SEQUENCE: 27
tagcatctga atttcataac caatctcgat acac                                34

<210> SEQ ID NO 28
<211> LENGTH: 17
<212> TYPE: PRT
<213> ORGANISM: Arabidopsis thaliana
<220> FEATURE:
<221> NAME/KEY: DNA_BIND
<222> LOCATION: (1)..(17)
<223> OTHER INFORMATION: Msh1 putative DNA binding domain

<400> SEQUENCE: 28

Val Leu Leu Cys Arg Val Gly Glu Phe Tyr Glu Ala Ile Gly Ile Asp
1               5                   10                  15

Ala
```

METHODS AND COMPOSITIONS FOR OBTAINING USEFUL PLANT TRAITS

CROSS-REFERENCE TO RELATED APPLICATIONS

This application claims the benefit of U.S. Provisional Patent Application No. 61/980,096, filed Apr. 16, 2014, which is incorporated herein by reference in its entirety.

STATEMENT REGARDING FEDERALLY SPONSORED RESEARCH OR DEVELOPMENT

This invention was made with Government Support under a grant from the National Science Foundation (IOS 1126935). The government has certain rights to this invention.

INCORPORATION OF SEQUENCE LISTING

The sequence listing contained in the file named "HEMISequences-JAN182016.txt", which is 165,598 bytes in size (measured in operating system MS-Windows), contains 28 sequences, and which was created on Jan. 19, 2016, is contemporaneously filed with this specification by electronic submission (using the United States Patent Office EFS-Web filing system) and is incorporated herein by reference in its entirety.

BACKGROUND

Previous studies have shown that altered methylation patterns are highly heritable over multiple generations and can be incorporated into a quantitative analysis of variation (Vaughn et al. 2007 PLoS Biol. 2007 July; 5(7):e174. Epub 2007 Jun. 19.; Zhang Science. 2008 Apr. 25; 320(5875): 489-92. doi: 10.1126/science.1153996.; Cortijo et al., Science. 2014 Mar. 7; 343(6175):1145-8. doi: 10.1126/science.1248127. Epub 2014 Feb. 6.). Earlier studies of methylation changes in *Arabidopsis* suggest amenability of the epigenome to recurrent selection and also suggest that it is feasible to establish new and stable epigenetic states (F. Johannes et al. *PLoS Genet.* 5, e1000530 (2009); F. Roux et al. *Genetics* 188, 1015 (2011). Manipulation of the *Arabidopsis* met1 and ddmt mutants has allowed the creation of epi-RIL populations that show both heritability of novel methylation patterning and epiallelic segregation, underscoring the likely influence of epigenomic variation in plant adaptation (F. Roux et al. *Genetics* 188, 1015 (2011)). In natural populations, a large proportion of the epiallelic variation detected in *Arabidopsis* is found as CpG methylation within gene-rich regions of the genome (C. Becker et al. Nature 480, 245 (2011), R. J. Schmitz et al. *Science* 334, 369 (2011). Induction of traits that exhibit cytoplasmic inheritance (Redei Mutat. Res. 18, 149-162, 1973; Sandhu et al. Proc Natl Acad Sci USA. 104:1766-70, 2007) or that exhibit nuclear inheritance by suppression of the MSH1 gene has also been reported (WO 2012/151254; Xu et al. Plant Physiol. Vol. 159:711-720, 2012). Genetic hemicomplementation experiments, wherein plastidic MSH1 was suppressed in the presence of mitochondrial-targeted MSH1, show that suppression of MSH1 in the plastid triggers a variegation phenotype (Xu et al. Plant Physiol. Vol. 159: 711-720, 2012).

SUMMARY

In general, it is a non-limiting objective of the present disclosure to introduce heritable and epigenetic and/or genetic variation that result in plants that have useful traits exhibiting nuclear and/or maternal inheritance by suppression of plastidic MSH1 in the presence of mitochondrial-targeted MSH1. It is also a non-limiting objective of the present disclosure to introduce heritable and epigenetic and/or genetic variation that result in plants that are useful for plant breeding by suppression of plastidic MSH1 in the presence of mitochondrial-targeted MSH1. Suppression of plastidic MSH1 in the presence of mitochondrial-targeted MSH1 provides an improved method of producing useful heritable and epigenetic and/or genetic variation in plants, as one non-limiting improvement is prevention of mitochondrial recombination that can occur as a consequence of MSH1 suppression when MSH1 suppression occurs in both the plastids and mitochrondria. Methods for producing a plant plant having a useful trait or useful for plant breeding, methods for identifying one or more altered chromosomal loci in a plant having a useful trait or that are useful for plant breeding, methods for obtaining plants comprising modified chromosomal loci having a useful trait or that are useful for plant breeding, improved plants from said breeding, parts of those plants including cells, leafs, stems, flowers and seeds, methods of using the plants and plant parts, and products of those plants and plant parts, including processed products such as a feed or a meal are provided herein.

Methods for producing a plant having a useful trait comprising the steps of: (a) crossing a first plant to a second plant wherein said first plant is subjected to suppression of plastidic MSH1 in the presence of mitochondrial-targeted MSH1 or is derived from a progenitor plant subjected to suppression of plastidic MSH1 in the presence of mitochondrial-targeted MSH1; and, (b) selecting one or more progeny plants having a useful trait and having recovered MSH1 function, thereby producing a plant exhibiting a useful trait are provided herein. Methods for producing a plant having a useful trait comprising the steps of: (a) crossing a first plant to a second plant wherein said first plant is subjected to suppression of plastidic MSH1 in the presence of mitochondrial-targeted MSH1 or is derived by selfing from a progenitor plant subjected to suppression of plastidic MSH1 in the presence of mitochondrial-targeted MSH1; (b) selecting one or more progeny plants having a useful trait and having recovered MSH1 function, thereby producing a plant exhibiting a useful trait are also provided. Methods for producing a plant having a useful trait exhibiting nuclear inheritance comprising the steps of: (a) crossing a first plant to a second plant wherein said first plant is subjected to suppression of plastidic MSH1 in the presence of mitochondrial-targeted MSH1 or is derived from a progenitor plant subjected to suppression of plastidic MSH1 in the presence of mitochondrial-targeted MSH1; and, (b) selecting one or more progeny plants having a useful trait and having recovered MSH1 function, thereby producing a plant having a useful trait exhibiting nuclear inheritance are provided herein. Methods for producing a plant having a useful trait exhibiting nuclear inheritance comprising the steps of: (a) crossing a first plant to a second plant wherein said first plant is subjected to suppression of plastidic MSH1 in the presence of mitochondrial-targeted MSH1 or is derived by selfing from a progenitor plant subjected to suppression of plastidic MSH1 in the presence of mitochondrial-targeted MSH1; (b) selecting one or more progeny plants having a useful trait and having recovered MSH1 function, thereby producing a plant having a useful trait exhibiting nuclear inheritance are provided herein. In certain embodiments said first plant or its progenitor plant do not exhibit any MSH1-dr phenotypes.

Methods for producing a plant having a useful trait exhibiting maternal inheritance comprising the steps of: (a) crossing a first plant to a second plant wherein said first plant is subjected to suppression of plastidic MSH1 in the presence of mitochondrial-targeted MSH1 or is derived from a progenitor plant subjected to suppression of plastidic MSH1 in the presence of mitochondrial-targeted MSH1, wherein said first plant or its progenitor plant does not exhibit any MSH1-dr phenotypes; and, (b) selecting one or more progeny plants having a useful trait and having recovered MSH1 function, thereby producing a plant having a useful trait exhibiting maternal inheritance are provided herein. Methods for producing a plant having a useful trait exhibiting maternal inheritance comprising the steps of: (a) crossing a first plant to a second plant wherein said first plant is subjected to suppression of plastidic MSH1 in the presence of mitochondrial-targeted MSH1 or is derived by selfing from a progenitor plant subjected to suppression of plastidic MSH1 in the presence of mitochondrial-targeted MSH1, wherein said first plant or its progenitor plant does not exhibit any MSH1-dr phenotypes; and, (b) selecting one or more progeny plants having a useful trait and having recovered MSH1 function, thereby producing a plant having a useful trait exhibiting maternal inheritance are provided herein. In certain embodiments said second plant or its progenitor plant are not subjected to MSH1 suppression or suppression of plastidic MSH1 in the presence of mitochondrial-targeted MSH1. In certain embodiments said second plant or its progenitor plant are subjected to MSH1 suppression or suppression of plastidic MSH1 in the presence of mitochondrial-targeted MSH1. In certain embodiments of one or more of the aforementioned methods said first plant is derived from a plant cell subjected to MSH1 suppression or suppression of plastidic MSH1 in the presence of mitochondrial-targeted MSH1. In certain embodiments of one or more of the aforementioned methods the first plant(s) of step (a) exhibit an improvement in a useful trait in comparison to a control plant. In certain embodiments of one or more of the aforementioned methods said first plant or said second plant in step (a) is an inbred plant. In certain embodiments said second plant in step (a) is isogenic with said first plant in step (a). In certain embodiments said first plant in step (a) is genetically heterogeneous and derived from parents in a single heterotic group. In certain embodiments said first plant in step (a) is genetically heterogeneous and derived from parents in distinct heterotic groups. In certain embodiments about 1% to about 45% of the population of progeny plants are selected for the useful trait in step (b).

Methods for identifying one or more altered chromosomal loci in a plant that can confer a useful trait comprising the steps of: (a) comparing one or more chromosomal regions in a reference plant that does not exhibit said useful trait to one or more corresponding chromosomal regions in a test plant that does exhibit said useful trait, wherein said test plant expresses MSH1 and was obtained from a parental plant or plant cell wherein plastidic MSH1 was suppressed in the presence of mitochondrial-targeted MSH1; and, (b) selecting for one or more altered chromosomal loci present in said test plant that are absent in said reference plant and that are associated with said useful trait are provided herein. In certain embodiments said test plant of step (a) does not exhibit any MSH1-dr phenotype.

Methods for producing a plant exhibiting a useful trait comprising the steps of: (a) introducing a chromosomal modification associated with a useful trait into a plant, wherein said chromosomal modification is induced by suppression of plastidic MSH1 in the presence of mitochondrial-targeted MSH1; and, (b) selecting for a plant that comprises said chromosomal modification and exhibits said useful trait are provided herein. In certain embodiments said plant of step (a) does not exhibit any MSH1-dr phenotype.

Methods for producing a plant having a useful trait comprising the steps of: (a) selfing a plant wherein said plant is subjected to suppression of plastidic MSH1 in the presence of mitochondrial-targeted MSH1 or is derived from a progenitor plant subjected to suppression of plastidic MSH1 in the presence of mitochondrial-targeted MSH1; (b) selecting one or more progeny plants having a useful trait and having recovered MSH1 function, thereby producing a plant exhibiting a useful trait are provided herein. Methods for producing a plant having a useful trait comprising the steps of: (a) selfing a plant wherein said plant is subjected to suppression of plastidic MSH1 in the presence of mitochondrial-targeted MSH1 or is derived by selfing from a progenitor plant subjected to suppression of plastidic MSH1 in the presence of mitochondrial-targeted MSH1; (b) selecting one or more progeny plants having a useful trait and having recovered MSH1 function, thereby producing a plant exhibiting a useful trait are provided herein. Methods for producing a plant having a useful trait comprising the steps of: (a) selfing a plant wherein said plant is subjected to suppression of plastidic MSH1 in the presence of mitochondrial-targeted MSH1 or is derived by selfing from a progenitor plant subjected to suppression of plastidic MSH1 in the presence of mitochondrial-targeted MSH1, wherein said plant or its progenitor plant does not exhibit any MSH1-dr phenotypes; (b) selecting one or more progeny plants having a useful trait and having recovered MSH1 function, thereby producing a plant exhibiting a useful trait are provided herein. In certain embodiments said one or more progeny plants of step (b) have a useful trait exhibiting nuclear inheritance, wherein said plant or its progenitor plant of step (a) does not exhibit any MSH1-dr phenotypes. In certain embodiments said one or more progeny plants of step (b) have a useful trait exhibiting maternal inheritance. In certain embodiments said plant or its progenitor plant of step (a) is derived from a plant cell subjected to MSH1 suppression or suppression of plastidic MSH1 in the presence of mitochondrial-targeted MSH1. In certain embodiments said plant or its progenitor plant of step (a) is derived from a plant cell subjected to MSH1 suppression or suppression of plastidic MSH1 in the presence of mitochondrial-targeted MSH1, wherein said one or more progeny plants of step (b) have a useful trait exhibiting nuclear inheritance. In certain embodiments said plant or its progenitor plant of step (a) is derived from a plant cell subjected to MSH1 suppression or suppression of plastidic MSH1 in the presence of mitochondrial-targeted MSH1, wherein said one or more progeny plants of step (b) have a useful trait exhibiting maternal inheritance. In certain embodiments the selfed plant of step (a) exhibits an improvement in a useful trait in comparison to a control plant. In certain embodiments the selfed plant of step (a) exhibits an increased size or yield in comparison to a control plant. In certain embodiments said selfed plant in step (a) is an inbred plant. In certain embodiments said selfed plant in step (a) is genetically heterogeneous and derived from parents in a single heterotic group. In certain embodiments said selfed plant in step (a) is genetically heterogeneous and derived from parents in distinct heterotic groups. In certain embodiments about 1% to about 45% of the population of progeny plants in step (b) have a useful trait. In certain embodiments of any of the aforementioned said selfed plant in step (a) or said one or more progeny plants of step (b) can be clonally propagated.

Methods of identifying a plant harboring a useful trait comprising the steps of: (a) crossing a candidate plant to a second plant, wherein said candidate plant is subjected to suppression of plastidic MSH1 in the presence of mitochondrial-targeted MSH1 or is derived by selfing from a progenitor plant or plant cell subjected to suppression of plastidic MSH1 in the presence of mitochondrial-targeted MSH1, wherein said candidate plant or its progenitor plant does not exhibit any MSH1-dr phenotypes; and, (b) identifying one or more progeny plants from the cross in step (a) that exhibit a useful trait to a greater extent than the candidate plant, the second plant, or a control plant, thereby identifying the candidate plant as a plant that harbors a useful trait are provided herein. Methods of identifying a plant harboring a useful trait comprising the steps of: (a) crossing a candidate plant to a second plant, wherein the candidate plant is subjected to suppression of plastidic MSH1 in the presence of mitochondrial-targeted MSH1 or is derived from a progenitor plant or plant cell subjected to suppression of plastidic MSH1 in the presence of mitochondrial-targeted MSH1 and wherein said candidate plant or its progenitor plant does not exhibit any MSH1-dr phenotypes; and, (b) identifying one or more progeny plants from the cross in step (a) that exhibit a useful trait to a greater extent than the candidate plant, the second plant, or a control plant, thereby identifying the candidate plant as a plant that harbors a useful trait are provided herein. In certain embodiments a control plant is progeny of a cross between; (i) a plant that is not progeny of a selfed plant, a crossed plant, or parent thereof that is or had been subjected to suppression of plastidic MSH1 in the presence of mitochondrial-targeted MSH1; and (ii) a plant that is isogenic to the second plant.

Methods for producing a plant exhibiting new combinations of altered chromosomal loci useful for breeding comprising the steps of: (a) crossing a plant comprising altered chromosomal loci induced by suppression of plastidic MSH1 in the presence of mitochondrial-targeted MSH1 to produce progeny; and, (b) assaying the DNA methylation of said progeny to identify and select individuals with new combinations of altered chromosomal loci, thereby producing a plant exhibiting new combinations of altered chromosomal loci useful for breeding are provided herein. In certain embodiments one or more altered chromosomal loci are selected from the group consisting of MSH1, pericentromeric regions, CG enhanced genes, CG depleted genes, transposable elements, transposable elements containing genes, and transposable elements in pericentromeric regions. In certain embodiments the DNA methylation of one or more altered chromosomal loci occurs at CHG or CHH sites within a DNA region selected from the group consisting of MSH1, pericentromeric regions, transposable elements, transposable elements containing genes, and transposable elements in pericentromeric regions. In certain embodiments the DNA methylation of one or more altered chromosomal loci occurs at CG sequences near or within CG altered genes. Methods for producing a plant exhibiting new combinations of altered chromosomal loci useful for breeding comprising the steps of: (a) crossing a plant comprising altered chromosomal loci induced by suppression of plastidic MSH1 in the presence of mitochondrial-targeted MSH1 to produce progeny; and, (b) assaying one or more sRNAs of said progeny to identify and select individuals with new combinations of altered chromosomal loci, thereby producing a plant exhibiting new combinations of altered chromosomal loci useful for breeding are provided herein. In certain embodiments one or more sRNAs assayed have sequence homology to one or more regions selected from the group consisting of MSH1, pericentromeric regions, CG enhanced genes, CG depleted genes, transposable elements, transposable elements containing genes, and transposable elements in pericentromeric regions. Methods for identifying a plant with altered chromosomal loci useful for plant breeding comprising the steps of: (a) assaying DNA methylation of one or more plants comprising altered chromosomal loci induced by suppression of plastidic MSH1 in the presence of mitochondrial-targeted MSH1; and, (b) identifying one or more plants from step (a) comprising one or more altered chromosomal loci selected from the group consisting of MSH1, pericentromeric regions, CG enhanced genes, CG depleted genes, transposable elements, transposable elements containing genes, and transposable elements in pericentromeric regions, thereby identifying a plant with altered chromosomal loci useful for plant breeding are provided herein. In certain embodiments the DNA methylation of one or more altered chromosomal loci occurs at CHG or CHH at DNA sequences selected from the group consisting of MSH1, pericentromeric regions, transposable elements, transposable elements containing genes, and transposable elements in pericentromeric regions. In certain embodiments the DNA methylation of one or more altered chromosomal loci occurs at CG sequences near or within CG altered genes. Methods for identifying a plant with altered chromosomal loci useful for plant breeding comprising the steps of: (a) assaying one or more sRNAs of one or more plants comprising altered chromosomal loci induced by suppression of plastidic MSH1 in the presence of mitochondrial-targeted MSH1; and, (b) identifying one or more plants from step (a) comprising increases or decreases in one or more sRNAs with homology at DNA sequences to one or more regions selected from the group of altered chromosomal loci consisting of MSH1, pericentromeric regions, CG enhanced genes, CG depleted genes, transposable elements, transposable elements containing genes, and transposable elements in pericentromeric regions, thereby identifying a plant with altered chromosomal loci useful for plant breeding are provided herein. Methods for producing a plant exhibiting new combinations of altered chromosomal loci useful for breeding comprising the steps of: (a) selfing a plant comprising altered chromosomal loci induced by suppression of plastidic MSH1 in the presence of mitochondrial-targeted MSH1 to produce progeny; and, (b) assaying the DNA methylation at altered chromosomal loci of said progeny to identify and select individuals with new combinations of altered chromosomal loci are also provided. In certain embodiments one or more altered chromosomal loci are selected from the group consisting of MSH1, pericentromeric regions, CG enhanced genes, CG depleted genes, transposable elements, transposable elements containing genes, and transposable elements in pericentromeric regions. In certain embodiments the DNA methylation of one or more altered chromosomal loci occurs at one or more CHG or CHH sites within one or more DNA regions selected from the group consisting of MSH1, pericentromeric regions, transposable elements, transposable elements containing genes, and transposable elements in pericentromeric regions. In certain embodiments the DNA methylation of one or more altered chromosomal loci occurs at one or more CG sequences near or within one or more CG altered genes. Methods for producing a plant exhibiting new combinations of altered chromosomal loci useful for breeding comprising the steps of: (a) selfing a plant comprising altered chromosomal loci induced by suppression of plastidic MSH1 in the presence of mitochondrial-targeted MSH1 to produce progeny; and, (b) assaying one or more sRNAs of said progeny to identify and select individuals with new combinations of altered chromosomal loci. In certain embodiments one or more sRNAs assayed have sequence homology to one or more regions selected from the group of altered chromosomal loci consisting of MSH1, pericentromeric regions, CG enhanced genes, CG depleted genes, transposable elements, transposable elements containing genes, and transposable elements in pericentromeric regions. Methods for selecting a plant comprising one or more altered chromosomal loci useful for plant breeding comprising the steps of: (a) comparing the DNA methylation status of one or more nuclear chromosomal regions in a reference plant to one or more corresponding nuclear chromosomal regions in a candidate plant, wherein said candidate plant or its progenitor was obtained suppression of plastidic MSH1 in the presence of mitochondrial-targeted MSH1; and, (b) selecting a candidate plant comprising one or more nuclear chromosomal regions present in the candidate plant with a DNA methylation status that is distinct from the DNA methylation status in the reference plant, thereby selecting a plant comprising one or more altered chromosomal loci useful for plant breeding are provided herein. Methods for selecting a plant comprising one or more altered chromosomal loci useful for plant breeding comprising the steps of: (a) comparing one or more sRNAs with homology to one or more nuclear chromosomal regions in a reference plant to one or more sRNAs from corresponding nuclear chromosomal regions in a candidate plant, wherein said candidate plant or its progenitor was obtained by suppression of plastidic MSH1 in the presence of mitochondrial-targeted MSH1; and, (b) selecting a candidate plant comprising one or more sRNA with abundances or sequences that are distinct from the sRNAs in the reference plant, thereby selecting a plant comprising one or more altered chromosomal loci useful for plant breeding are also provided. A plant containing a mutation in the FYE region of the DNA binding domain of MSH1, wherein such mutation is not present in control plants of the same species, is provided herein. In certain embodiments said mutation in the FYE region of the DNA binding domain of MSH1 is FYA. In certain embodiments said mutation in the FYE region of the DNA binding domain of MSH1 is selected from the group consisting of FYZ or FXZ, where Z is any amino acid other than E, and X is any amino acid other than Y. In any of the aformention methods the plant is from the group consisting of corn, wheat, rice, sorghum, millet, tomatoes, potatoes, soybeans, tobacco, cotton, canola, alfalfa, rapeseed, sugar beets, and sugarcane. In any of the aformention methods a plant, plant part, seed, or plant or tissue from a plant cell can be clonally propagated. Progeny from a plant grafted as a scion to a rootstock from the plant of any one of the aformention methods are also provided. Progeny from a plant grafted as a rootstock to a scion from the plant of any one of the aformention methods are also provided.

Methods for producing a seed lot comprising: (i) growing a population of plants, wherein said population comprises two or more of the plants or progeny thereof of any one of the aforementioned methods; (ii) selecting a first sub-population of plants exhibiting a useful trait; and, (iii) obtaining a seed lot from the first selected sub-population of step (ii) or, optionally, repeating steps (i) and (ii) on a second population of plants grown from the seed obtained from the first selected sub-population of plants are provided herein. Also provided are plants or progeny thereof that exhibit a useful trait that are made by the aforementioned methods. Plant parts obtained from the plant or progeny thereof made by any one of the aforementioned methods are also provided. In certain embodiments, the part is selected from the group consisting of a seed, leaf, stem, fruit, and a root. Processed plant products obtained from the plant parts are also provided. Clonal propagates obtained from the plants, the progeny thereof, or from the plant parts are also provided. Plants comprising a scion grafted to rootstock that had been subjected to suppression of plastidic MSH1 in the presence of mitochondrial-targeted MSH1 are provided herewith. Such grafted plants can be used in methods for producing a plant exhibiting useful traits, methods for identifying one or more altered chromosomal loci in a plant that can confer a useful trait, and in methods for obtaining plants comprising modified chromosomal loci that can confer a useful trait. Such grafted plants that exhibit useful traits, progeny of the grafted plants exhibiting the useful traits, parts of the grafted or progeny plants including cells, leafs, stems, flowers and seeds, methods of using the grafted or progeny plants and plant parts, and products of those plants and plant parts, including processed products such as a feed or a meal are also provided herein. Plants comprising a scion to which a rootstock had been grafted, where the rootstock is obtained from a plant or a parent plant thereof that had been subjected to suppression of plastidic MSH1 in the presence of mitochondrial-targeted MSH1 are provided herein. In certain embodiments, the rootstock confers to the grafted plant or to the progeny thereof an improvement in a useful trait in comparison to a control plant which lacks a graft to the rootstock or in comparison to progeny of the control plant. In certain embodiments, the rootstock that is grafted to the scion is obtained from a plant that was selected for the useful trait and that was derived from a parent plant that had been subjected to suppression of plastidic MSH1 in the presence of mitochondrial-targeted MSH1. In certain embodiments, the plant comprising rootstock obtained from a plant that was selected for the useful trait and that was derived from a parent plant that had been subjected to suppression of plastidic MSH1 in the presence of mitochondrial-targeted MSH1 exhibits the useful trait. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant.

In certain embodiments, the plant or its progenitor subjected to suppression of plastidic MSH1 in the presence of mitochondrial-targeted MSH1 contain(s) one or more epigenetic changes in one or more nuclear chromosomes, wherein the epigenetic changes are absent from nuclear chromosomes of the control plant or are absent from nuclear chromosomes of a plant from which the scion was obtained. In certain embodiments, the epigenetic change(s) are also present in the rootstock that had been subjected to suppression of plastidic MSH1 in the presence of mitochondrial-targeted MSH1. In certain embodiments, the epigenetic changes are associated with the improvement in the useful trait. In certain embodiments, the rootstock contain(s) one or more epigenetic changes in one or more nuclear chromosomes that are absent from nuclear chromosomes of rootstock obtained from a plant or are absent from nuclear chromosomes of a parent plant thereof had not been subjected to suppression of plastidic MSH1 in the presence of mitochondrial-targeted MSH1. In certain embodiments, the scion and/or the rootstock, or plant or its progenitor subjected to suppression of plastidic MSH1 in the presence of mitochondrial-targeted MSH1 exhibit CG hypermethylation of a region encompassing a MSH1 locus in comparison to a control plant that had not been subjected to suppression of plastidic MSH1 in the presence of mitochondrial-targeted MSH1. In certain embodiments, the scion and/or the rootstock, or plant or its progenitor subjected to suppression of plastidic MSH1 in the presence of mitochondrial-targeted MSH1 exhibit pericentromeric CHG hyper-methylation in comparison to a control plant that had not been subjected to suppression of plastidic MSH1 in the presence of mitochondrial-targeted MSH1. In certain embodiments, the scion and/or the rootstock, or plant or its progenitor subjected to suppression of plastidic MSH1 in the presence of mitochondrial-targeted MSH1 exhibit CHH hyper-methylation in comparison to a control plant that had not been subjected to suppression of plastidic MSH1 in the presence of mitochondrial-targeted MSH1. In certain embodiments, the scion and/or the rootstock, or plant or its progenitor subjected to suppression of plastidic MSH1 in the presence of mitochondrial-targeted MSH1 exhibit CG and/or CHG and/or CHH hyper-methylation in comparison to a control plant that had not been subjected to suppression of plastidic MSH1 in the presence of mitochondrial-targeted MSH1. In certain embodiments, the plant is selected from the group consisting of a crop plant, a tree, a bush, and a vine. In certain embodiments, the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and sorghum. In certain embodiments, the tree is selected from the group consisting of an apple, apricot, grapefruit, orange, peach, pear, plum, lemon, coconut, poplar, *eucalyptus*, date palm, palm oil, pine, and an olive tree. In certain embodiments, the bush is selected from the group consisting of a blueberry, raspberry, and blackberry bush. Also provided are plants or progeny thereof obtained by any of the aforementioned methods. Also provided are plant parts obtained from the plant or progeny thereof that were made by any of the aforementioned methods. In certain embodiments, the plant part is selected from the group consisting of a seed, leaf, stem, fruit, and a root. Also provided are clonal propagates obtained from the plant or progeny thereof that were made by any of the aforementioned methods.

Also provided are methods for producing a plant exhibiting a useful trait comprising the steps of: (a) crossing a first plant to a second plant, wherein the first plant is any of the aforementioned plants comprising a scion to which a rootstock had been grafted; and, (b) selecting one or more progeny plants obtained from the cross for an improvement in the useful trait in comparison to a control plant, thereby producing a plant exhibiting a useful trait. In certain embodiments, the control plant is selected from the group consisting of progeny of a cross between a plant which lacks a graft to the rootstock and a plant that is isogenic to the second plant, progeny of a self of a plant that lacks a graft to the rootstock, and progeny of a self of the second plant. In certain embodiments, at least the scion of the first plant is from a different heterotic group than the second plant. In certain embodiments, the scion and the rootstock of the first plant are from a different heterotic group than the second plant. In certain embodiments, the scion and the rootstock of the first plant are both from the same heterotic group but are from a different heterotic group than the second plant. In certain embodiments, at least the scion of the first plant is from the same heterotic group as the second plant. In certain embodiments, the scion and the rootstock of the first plant are from the same heterotic group as the second plant. In certain embodiments the second plant and at least the scion of the first plant are isogenic. In certain embodiments, the second plant and the scion and the rootstock of the first plant are isogenic. In certain embodiments of any of the aforementioned methods, the second plant or a parent thereof had also been subjected to suppression of plastidic MSH1 in the presence of mitochondrial-targeted MSH1. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. Also provided are plants obtained by any of the aforementioned methods. Also provided are plant parts obtained from plants made by any of the aforementioned methods. In certain embodiments, the plant part is selected from the group consisting of a seed, leaf, stem, fruit, and a root. Also provided are processed plant products obtained from plants made by any of the aforementioned methods or plant parts obtained from those plants.

Also provided are methods for producing a seed lot comprising: (i) growing a population of plants, wherein said population comprises two or more of any of the aforementioned plants comprising a scion to which a rootstock had been grafted and/or plants made by any of the aforementioned methods; (ii) selecting a first sub-population of plants exhibiting a useful trait; and, (ii) obtaining a seed lot from the first selected sub-population of step (i) or, optionally, repeating steps (i) and (ii) on a second population of plants grown from the seed obtained from the first selected sub-population of plants. Also provided are seed lots produced by the aforementioned methods, as well as plants, plant parts, and processed plant products obtained from the seed lots. Also provided are methods for producing a seed lot comprising: (i) growing a population of plants, wherein said population comprises two or more of any of the aforementioned plants comprising a scion to which a rootstock had been grafted and/or plants made by any of the aforementioned methods; and (ii) obtaining a seed lot from the population. Also provided are seed lots produced by the aforementioned method as well as plants, plant parts, and processed plant products obtained from the seed lots. In certain embodiments, any of the aforementioned plants, parental plants or progeny thereof, plant parts, or processed products thereof produced by the methods provided herein exhibit a useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. In certain embodiments, organellar function has been recovered in the plant. In certain embodiments, the plants, parental plants, progeny thereof, plant parts, or processed products thereof contains one or more epigenetic changes in one or more nuclear chromosomes, wherein the epigenetic changes are absent from the nuclear chromosomes of a control plant, plant part, or processed product thereof. In certain embodiments, the epigenetic changes are associated with the improvement in the useful trait.

In certain embodiments, the plants, parental plants, progeny thereof, plant parts, or processed products thereof exhibit CG hypermethylation of a region encompassing a MSH1 locus in comparison to a control plant that had not been subjected to the suppression of plastidic MSH1 in the presence of mitochondrial-targeted MSH1. In certain embodiments, plants, parental plants, progeny thereof, plant parts, or processed products thereof exhibit pericentromeric CHG hyper-methylation in comparison to a control plant that had not been subjected to the suppression of plastidic MSH1 in the presence of mitochondrial-targeted MSH1. In certain embodiments, plants, parental plants, progeny thereof, plant parts, or processed products thereof exhibit CG hypermethylation and/or CHG hypermethylation at one or more nuclear chromosomal loci in comparison to corresponding nuclear chromosomal loci of a control plant that had not been subjected to the suppression of plastidic MSH1 in the presence of mitochondrial-targeted MSH1.

BRIEF DESCRIPTION OF THE DRAWINGS

The file of this patent contains at least one photograph executed in color. Copies of this patent with color photograph(s) will be provided by the Office upon request and payment of the necessary fee. The accompanying drawings, which are incorporated in and form a part of the specification, illustrate certain embodiments of the present disclosure. In the drawings:

FIGS. 5 and 6. Structures of constructs for concurrent RNAi and expression of mitochondrially targeted MSH1. The name of the DNA region is the top line of each section, followed by the linear order of DNA elements in various constructs. The SEQ ID for some of the DNA elements is also indicated. Abbreviations: L Br is the T-DNA left border; R Br is the T-DNA right border, and MCS is the multiple cloning sites comprising the following sites: EcoRI BamHI SbfI HindIII; // indicates the 5' or 3' ends of gene cassettes; NOS 3' indicates the Nopaline Synthase 3' polyadenylation region; OCS 3' indicates the Octapine Synthase 3' polyadenylation region; other names are described in the Examples.

DESCRIPTION

Figure 1:
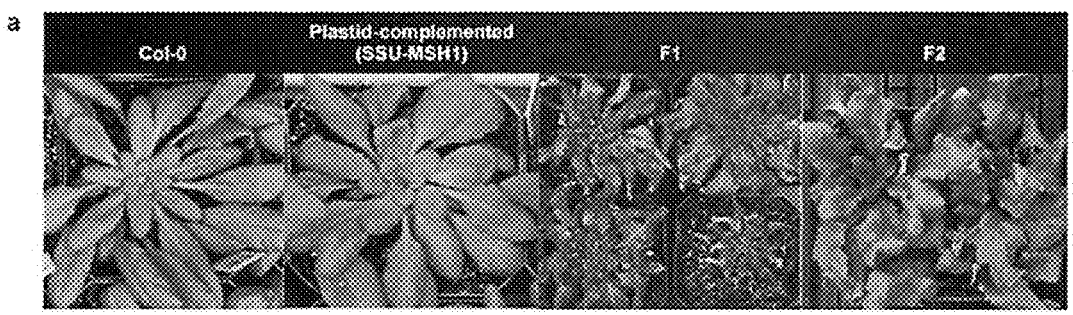
FIG. 1. a, Arabidopsis $F_1$ plants resulting from crosses of the msh1 chloroplast hemi-complementation line×Col-0 wild type. Transgene-mediated chloroplast hemi-complementation of msh1 restores the wild type phenotype[1]. However, crossing of these hemi-complemented lines to Col-0 results in a variable proportion of plants displaying leaf curl (at varying intensities) in the $F_1$. The cause of this phenotype is not yet known, but it is heritable in derived $F_2$ populations. b, Analysis of phenotype data from individual Arabidopsis $F_2$ families derived by crossing hemi-complementation lines×Col-0 wild type. SSU-MSH1 refers to lines transformed with the plastid-targeted form of MSH1; AOX-MSH1 refers to lines containing the mitochondrial-targeted form of the MSH1 transgene. In all genetic experiments using hemi-complementation, presence/absence of the transgene was confirmed with a PCR-based assay.

As used herein, the phrases "useful for plant breeding" or "useful for breeding" refer to plants derived from one or more progenitor plants suppressed for plastidic MSH1 in the presence of mitochondrial-targeted MSH1 that are useful in a plant breeding program for the objecting of developing improved plants and plant seeds.

As used herein, the terms "pericentromeric" or "pericentromere" refer to heterochromatic regions containing abundant repeated sequences, transposable elements, and retrotransposons that physically flank the centromeric regions. At the sequence level, a functional definition for pericentromeric sequences are highly repeated sequences that contain transposable elements and retrotransposons embedded in said repeated sequences, even if disperse throughout the genome. When known, centromeric repeats can be computationally removed from the repeated sequences, but their presence is not detrimental if not computationally removed. When available, chromosomal positioning information about the location of sequences that are located adjacent to the centromere can be used as an additional criterion for pericentromeric sequences.

As used herein, the phrases "CG altered gene" or "CG altered genes" refer to a gene or genes with increased or decreased levels of DNA methylation (5meC) at CG nucleotides within or near a gene or genes. The region near a gene is within 5,000 bp, preferably within 1,000 bp, of either the 5' or 3' end of the gene or genes.

As used herein, the phrase "CG enhanced genes" refers to genes identified as altered chromosomal loci with higher levels of DNA methylation or sRNA derived from a chromosomal region relative to the comparable chromosomal region of a reference plant.

As used herein, the terms "CG depleted genes" refers to genes identified as altered chromosomal loci with lower levels of DNA methylation or sRNA derived from a chromosomal region relative to the comparable chromosomal region of a reference plant.

As used herein, the phrases "altered chromosomal loci" (used as singular or plural herein) or "altered chromosomal locus (singular) refer to portions of a chromosome that have undergone a heritable and reversible epigenetic change relative to the corresponding parental chromosomal loci prior to suppression of MSH1 or of plastidic MSH1 in the presence of mitochondrial-targeted MSH1. The altered chromosomal loci can occur in any of the generations of progeny derived from a progenitor plant or plant cell subjected to suppression of MSH1 or of plastidic MSH1 in the presence of mitochondrial-targeted MSH1. Heritable and reversible epigenetic changes in altered chromosomal loci include, but are not limited to, methylation of chromosomal DNA, and in particular, methylation of cytosine residues to 5-methylcytosine residues. As used herein, "chromosomal loci" refer to loci in chromosomes located in the nucleus of a cell. Altered chromosomal loci can be assayed for DNA methylation or sRNA derived from these regions. Altered chromosomal loci have altered DNA methylation levels, and/or altered levels of sRNA derived from these regions, relative to the corresponding parental chromosomal loci prior to suppression of MSH1 or of plastidic MSH1 in the presence of mitochondrial-targeted MSH1 or to a parental chromosome in a lineage not subjected to MSH1 suppression.

As used herein, the phrase "new combinations of altered chromosomal loci" refers to nuclear chromosomal regions in a progeny plant with one or more differences in altered chromosomal loci when compared to altered chromosomal loci of a parental plant if derived by self-pollination, or if derived from a cross, when compared to either parental plant, each compared separately to said progeny plant.

As used herein, the phrase "reference plant" refers to a parental plant or progenitor of a parental plant prior to suppression of MSH1 or of plastidic MSH1 in the presence of mitochondrial-targeted MSH1, but otherwise isogenic to the candidate or test plant to which it is being compared. In a cross of two parental plants, a "reference plant" can also be from a parental plant wherein MSH1 suppression was not used in said parental plant or one of its progenitors.

As used herein, the phrase "comparing one or more chromosomal regions" refers to a comparison of amounts and sequences of the heritable and reversible epigenetic changes in altered chromosomal loci including, but are not limited to, methylation of chromosomal DNA, and in particular, methylation of cytosine residues to 5-methylcytosine residues and/or sRNA derived from these regions. As used herein, "chromosomal loci" refer to loci in chromosomes located in the nucleus of a cell. Altered chromosomal loci can be assayed for DNA methylation or sRNA derived from these regions. Altered chromosomal loci have altered DNA methylation levels, and/or altered levels of sRNA derived from these regions, relative to the corresponding parental chromosomal loci prior to suppression of MSH1 or of plastidic MSH1 in the presence of mitochondrial-targeted MSH1 or to a parental chromosome in a lineage not subjected to MSH1 suppression.

As used herein, the term "progeny" refers to any one of a first, second, third, or subsequent generation obtained from a parent plant if self pollinated or from parent plants if obtained from a cross. Any materials of the plant, including but not limited to seeds, tissues, pollen, and cells can be used as sources of RNA or DNA for determining the status of the RNA or DNA composition of said progeny.

As used herein, the phrases "suppression" or "suppressing expression" of a gene refer to any genetic, nucleic acid, nucleic acid analog, environmental manipulation, grafting, transient or stably transformed methods of any of the aforementioned methods, or chemical treatment that provides for decreased levels of functional gene activity in a plant or plant cell relative to the levels of functional gene activity that occur in an otherwise isogenic plant or plant cell that had not been subjected to this genetic or environmental manipulation.

As used herein, the terms "assaying" or "assayed" refer to methods for determining the amounts, or sequences, or both, of DNA methylation or sRNA, corresponding to one or more nuclear chromosomal regions for DNA or with homology to one or more nuclear chromosomal regions for sRNA. The nuclear chromosomal regions assayed for DNA methylation can be a single nucleotide position or a region greater than this. Preferably the DNA methylation is from a region comprising one or more CG, CHG, or CHH sites and is compared to the corresponding parental chromosomal loci prior to MSH1 suppression. sRNA can be measured for a single type of sRNA, one or more sRNAs, or a whole population of sRNAs by methods known to those skilled in the art.

As used herein, the phrases "epigenetic modifications" or "epigenetic modification" refer to heritable and reversible epigenetic changes that include, but are not limited to, methylation of chromosomal DNA, and in particular, methylation of cytosine residues to 5-methylcytosine residues. Changes in DNA methylation of a region are often associated with changes in sRNA levels with homology derived from the region.

As used herein, the phrases "increased DNA methylation" or "decreased DNA methylation" refer to nucleotides, regions, genes, chromosomes, and genomes located in the nucleus that have undergone a change in 5meC levels in a plant or progeny plant relative to the corresponding parental chromosomal loci prior to MSH1 suppression or suppression of plastidic MSH1 in the presence of mitochondrial-targeted MSH1 or to a parental plant not subjected to MSH1 suppression or plastidic MSH1 in the presence of mitochondrial-targeted MSH1.

As used herein, the term "comprising" means "including but not limited to".

As used herein, the phrase "crop plant" includes, but is not limited to, cereal, seed, grain, fruit, and vegetable crop plants.

As used herein, the phrases "commercially synthesized" or "commercially available" DNA refer to the availability of any sequence of 15 bp up to 1000 bp in length or longer from DNA synthesis companies that provide a DNA sample containing the sequence submitted to them.

As used herein, the phrase "loss of function" refers to a diminished, partial, or complete loss of function.

As used herein, the phrases "mutated gene" or "gene mutation" refer to portions of a gene that have undergone a heritable genetic change in a nucleotide sequence relative to the nucleotide sequence in the corresponding parental gene that results in a reduction in function of the gene's encoded protein function. Mutations include, but are not limited to, nucleotide sequence inversions, insertions, deletions, substitutions, or combinations thereof. In certain embodiments, the mutated gene can comprise mutations that are reversible. In this context, reversible mutations in the chromosome can include, but are not limited to, insertions of transposable elements, defective transposable elements, and certain inversions. In certain embodiments, the gene comprises mutations are irreversible. In this context, irreversible mutations in the chromosome can include, but are not limited to, deletions.

As used herein, the phrase "heterotic group" refers to genetically related germplasm that produce superior hybrids when crossed to genetically distinct germplasm of another heterotic group.

As used herein, the phrases "genetically homogeneous" or "genetically homozygous" refer to the two parental genomes provided to a progeny plant as being essentially identical at the DNA sequence level.

As used herein, the phrases "genetically heterogeneous" or "genetically heterozygous" refers to the two parental genomes provided to a progeny plant as being substantially different at the sequence level. That is, one or more genes from the male and female gametes occur in different allelic forms with DNA sequence differences between them.

As used herein, the term "isogenic" refers to the two plants that have essentially identical genomes at the DNA sequence levels level.

As used herein, the term "F1" refers to the first progeny of two genetically or epigenetically different plants. "F2" refers to progeny from the self pollination of the F1 plant. "F3" refers to progeny from the self pollination of the F2 plant. "F4" refers to progeny from the self pollination of the F3 plant. "F5" refers to progeny from the self pollination of the F4 plant. "Fn" refers to progeny from the self pollination of the F(n-1) plant, where "n" is the number of generations starting from the initial F1 cross. Crossing to an isogenic line (backcrossing) or unrelated line (outcrossing) at any generation will also use the "Fn" notation, where "n" is the number of generations starting from the initial F1 cross.

As used herein, the term "S1" refers to a first selfed plant. "S2" refers to progeny from the self pollination of the S1 plant. "S3" refers to progeny from the self pollination of the S2 plant. "S4" refers to progeny from the self pollination of the S3 plant. "S5" refers to progeny from the self pollination of the S4 plant. "Sn" refers to progeny from the self pollination of the S(n-1) plant, where "n" is the number of generations starting from the initial S1 cross.

As used herein, the terms "self", "selfing", or "selfed" refer to the process of self pollinating a plant.

As used herein, the term "RNAi" refers to any method such as hairpin RNAi, micro RNAs, VIGS, sense or antisense RNA, topical RNA, single or double stranded RNAs, methylation of chromosomal DNA, and other methods known to those skilled in the art that result in the production of small RNAs in the cell (siRNA) of 20 to 24 nucleotides in length with homology against one or more target genes or RNAs, including but not limited to MSH1 genes and mRNAs, that lead to methylation of DNA or to cleavage of mRNA or binding to target mRNAs to reduce mRNA and/or protein levels of a target of said RNAi method.

As used herein, the phrases "suppression of plastidic MSH1 in the presence of mitochondrial-targeted MSH1" or "plastidic MSH1 was suppressed in the presence of mitochondrial-targeted MSH1" refer to a reduction or loss in the amount and/or function of MSH1 in the plastid, and the retention of MSH1 amounts and/or function in the mitochondria. Multiple methods of achieving this are known to those skilled in the art, including, but not limited to: expression of a mitochondrial targeted MSH1 in a MSH1-deficient genotype, such as a mutation in the MSH1 gene; concurrent suppression of endogenous MSH1 by a method such as transient or stably transformed sources of RNAi or VIGS (virus induced gene silencing) and expression of a mitochondrial targeted MSH1 that is not suppressed by said RNAi; specific mutations in an endogenous MSH1 that attenuate plastid targeting or function and maintain or create mitochondrial targeting and function; and, mutation of the conserved DNA binding domain of MSH1 containing a FYE domain or FXE domain (where X is any amino acid) to FYA or FXA or FYX or FXX.

As used herein, the phrases "clonal propagate" or "vegetatively propagated" refer to a plant or progeny thereof obtained from a plant, plant cell, or tissue, or seed that is propagated as a plant cutting or tuber cutting or tuber. Clonal propagates can be obtained by methods including but not limited to regenerating whole plants from plant cells, plant embryos, cuttings, tubers, and the like. Various techniques used for such clonal propagation include, but are not limited to, meristem culture, somatic embryogenesis, thin cell layer cultures, adventitious shoot culture, and callus culture.

As used herein, the phrase "MSH1-dr phenotypes" refers to phenotypes that include leaf variegation, cytoplasmic male sterility (CMS), a reduced growth-rate phenotype, delayed or non-flowering phenotype, leaf wrinkling, increased plant tillering, decreased height, decreased internode elongation, plant tillering, and/or stomatal density changes that are observed in plants subjected to suppression of MSH1 or of plastidic MSH1 in the presence of mitochondrial-targeted MSH1.

As used herein, the phrase "developmental reprogramming or term "dr" refers to MSH1-dr phenotypes.

As used herein the terms "microRNA" or "miRNA" refers to both a miRNA that is substantially similar to a native miRNA that occurs in a plant as well as to an artificial miRNA. In certain embodiments, a transgene can be used to produce either a miRNA that is substantially similar to a native miRNA that occurs in a plant or an artificial miRNA.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter is linked such that the resulting translation product is in frame with the translational open reading frame that encodes the protein desired. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions (i.e., site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences, homologous recombination sequences), and sequences that provide replication functions (i.e., bacterial origins of replication, autonomous replication sequences, centromeric sequences).

As used herein, the term "transgene" or "transgenic", in the context of a chromosomal modification, refers to any recombinant DNA that has been transiently introduced into a cell or stably integrated into a chromosome that is stably maintained in a host cell. In this context, sources for the recombinant DNA include, but are not limited to, DNAs from an organism the same or distinct from the host cell organism, species distinct from the host cell species, varieties of the same species that are either distinct varieties or identical varieties, DNA that has been subjected to any in vitro modification, in vitro synthesis, recombinant DNA, and any combination thereof.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Methods for introducing heritable and epigenetic and/or genetic variation that result in plants that have useful traits exhibiting nuclear and/or maternal inheritance are provided herewith along with plants, plant seeds, plant parts, plant cells, vegetatively propagated cuttings or tubers or other clonal propagates, and processed plant products obtainable by these methods. In certain embodiments, methods provided herewith can be used to introduce epigenetic and/or genetic variation into varietal or non-hybrid plants that result in useful traits as well as useful plants, plant parts including, but not limited to, seeds, plant cells, and processed plant products that exhibit, carry, or otherwise reflect benefits conferred by the useful traits. In other embodiments, methods provided herewith can be used to introduce epigenetic and/or genetic variation into plants that are also amenable to hybridization.

In general, it is a non-limiting objective of the present disclosure to introduce heritable and epigenetic and/or genetic variation that result in plants that have useful traits exhibiting nuclear and/or maternal inheritance by suppression of plastidic MSH1 in the presence of mitochondrial-targeted MSH1. It is also a non-limiting objective of the present disclosure to introduce heritable and epigenetic and/or genetic variation that result in plants that are useful for plant breeding by suppression of plastidic MSH1 in the presence of mitochondrial-targeted MSH1. Methods for suppression of MSH1 and subsequent restoration of its function are disclosed in US Patent Application Publication No. 20120284814, U.S. Provisional Patent Application No. 61/863,267, U.S. Provisional Patent Application No. 61/882,140, U.S. Provisional Patent Application No. 61/901,349, which are each specifically incorporated herein by reference in their entireties. Said methods for suppression of MSH1 and subsequent restoration of its function are modified for suppression of plastidic MSH1 in the presence of mitochondrial-targeted MSH1 as described herein to produce plants with heritable and epigenetic and/or genetic variation with useful traits or that are useful for plant breeding.

Also provided herein are grafted plants comprising a scion to which a rootstock had been grafted, wherein the rootstock is obtained from a plant or a parent plant or plant cell thereof subjected to suppression of plastidic MSH1 in the presence of mitochondrial-targeted MSH1, as well as progeny plants and clonal propagates obtained from the grafted plant. Such rootstocks can be also used to introduce epigenetic and/or genetic variation into varietal or non-hybrid plants that result in useful traits as well as useful plants, plant parts including, but not limited to, seeds, plant cells, and processed plant products that exhibit, carry, or otherwise reflect benefits conferred by the useful traits. In other embodiments, such rootstocks can also be used to introduce epigenetic into plants that are also amenable to hybridization.

Rootstocks useful for introducing epigenetic and/or genetic variation into plants can be obtained from a variety of rootstock source plants that had been subjected to suppression plastidic MSH1 in the presence of mitochondrial-targeted MSH1. In certain embodiments, the rootstock source plant is a plant that had itself been subjected to suppression of plastidic MSH1 in the presence of mitochondrial-targeted MSH1. In other embodiments, the rootstock source plant is the progeny of a parental plant that had itself been subjected to suppression of plastidic MSH1 in the presence of mitochondrial-targeted MSH1. Various methods of making rootstock source plants by suppression of plastidic MSH1 in the presence of mitochondrial-targeted MSH1 are provided herein.

In certain embodiments where the plant, a rootstock source plant, or a parental plant thereof, had been subjected to suppression of plastidic MSH1 in the presence of mitochondrial-targeted MSH1, a population of progeny plants obtained from the plant or grafted plant are screened and progeny plants are selected for one or more useful traits. Such populations of selected progeny plants can be obtained by methods including, but not limited to, selfing or outcrossing the plant or the grafted plant comprising the rootstock to obtain seed that give rise to the population. Such populations of progeny plants can also be obtained by methods including, but not limited to, growing a population of plants that are derived from independent clonal propagates obtained from the plants or the grafted plant comprising the rootstock. Such selected individual progeny plants that exhibit the useful trait can then be sexually or asexually propagated to yield populations of plants that exhibit the useful trait or seed lots that exhibit or harbor the useful trait. Such sexual propagation can be accomplished by selfing or outcrossing the selected individual progeny plants that exhibit the useful trait.

In certain embodiments where the plant or the rootstock source plant is the progeny of a parental plant that had been subjected to suppression of plastidic MSH1 in the presence of mitochondrial-targeted MSH1, the plant or the rootstock source plant itself can be a plant that was selected for one or more useful traits. Grafting rootstock from a plant that had been selected for a useful trait to a scion that does not exhibit the trait can impart the trait to the resultant grafted plant or to progeny thereof. Resultant plants, grafted plants or progeny thereof that exhibit the useful trait can then be sexually or asexually propagated to yield populations of plants that exhibit the useful trait or seed lots that exhibit or harbor the useful trait.

In plants, grafted plants or progeny thereof, suppression of plastidic MSH1 in the presence of mitochondrial-targeted MSH1 in the plants or rootstock can be continuous and ongoing or can be transient. Non-limiting and exemplary methods for effecting continuous and ongoing suppression of plastidic MSH1 in the presence of mitochondrial-targeted MSH1 in the plants or rootstock include suppressing expression of plastidic MSH1 in the presence of mitochondrial-targeted MSH1 with mutations in the endogenous gene or with a transgene that yields a product that suppresses expression of the endogenous gene. Alternatively, the suppression of plastidic MSH1 in the presence of mitochondrial-targeted MSH1 in the plants or rootstock can be transient or have occurred in a parental plant from which the plant or rootstock was obtained but not in the rootstock that was used in the graft. Non-limiting and exemplary methods for effecting transient suppression of plastidic MSH1 in the presence of mitochondrial-targeted MSH1 in the plants or rootstock include suppressing expression of plastidic MSH1 in the presence of mitochondrial-targeted MSH1 with a transgene that provides for inducible or repressible expression of a product that suppresses expression of the endogenous gene, with a transgene(s) that can be excised, with a heterozygous transgene(s) insert that is removed from the rootstock by segregation, or by use of a Viral Induced Gene Silencing (VIGS) vector that suppresses expression of plastidic MSH1 in the presence of mitochondrial-targeted MSH1 target gene. Any of the methods described herein for restoring MSH1 function after suppression of plastidic MSH1 in the presence of mitochondrial-targeted MSH1 can be used to generate the plants or rootstock used in certain embodiments.

Grafting can be effected by any method that provides for establishment of a vascular connection between the rootstock and the scion. Methods of grafting that can be used to effect the connection between the scion and the rootstock include, but are not limited to, apical graftage, side graftage, bark graftage, and root graftage. Such methods for effecting grafts of scions to rootstock are disclosed in "Plant Propagation: Principles and Practices; Chapter 12: Techniques of Grafting" Ed. Hartman, Kester, Davies, and Geneve, $7^{th}$ Edition. Methods for effecting grafts of monocot plant scions to rootstocks that can be used with the scions and rootstocks provided herein are disclosed in Muzik and La Rue, The Grafting of Large Monocotyledonous Plants, Science 116, No. 3022: 589-591, 1952.

Plants, progeny thereof, or rootstocks thereof subjected to suppression of plastidic MSH1 in the presence of mitochondrial-targeted MSH1 or obtained from a parental plant that had been subjected to suppression of plastidic MSH1 in the presence of mitochondrial-targeted MSH1 can exhibit modifications of one or more nuclear chromosomes. In certain embodiments, such plants, progeny thereof, or rootstocks thereof subjected to suppression of plastidic MSH1 in the presence of mitochondrial-targeted MSH1 can exhibit characteristic DNA methylation and/or gene transcription patterns that occur in plants subjected to suppression of an MSH1 target gene. Such characteristic DNA methylation and/or gene transcription patterns that occur in plants or seeds subjected suppression of an MSH1 target gene include, but are not limited to, those patterns disclosed in Example 2 of U.S. Provisional Patent Application No. 61/863,267, the data and disclosure of which is specifically incorporated herein by reference in its entirety. In certain embodiments, plants, progeny thereof, or rootstocks thereof subjected to suppression of plastidic MSH1 in the presence of mitochondrial-targeted MSH1 will exhibit CG differentially methylated regions (DMR) of various discrete chromosomal regions that include, but are not limited to, regions that encompass the MSH1 locus. In certain embodiments, a CG hypermethylated region that encompasses the MSH1 locus will be about 0.1 to about 8 MBp (mega base pairs) in length. In certain embodiments, plants, progeny thereof, or rootstocks thereof subjected to suppression of plastidic MSH1 in the presence of mitochondrial-targeted MSH1 will also exhibit changes in plant defense and stress response gene expression. In certain embodiments, a plant, progeny thereof, a rootstock, a scion grafted thereto, and/or a plant cell, a seed, a progeny plant, plant populations, seed populations, and/or processed products obtained therefrom that has been subject to suppression of plastidic MSH1 in the presence of mitochondrial-targeted MSH1 target gene will exhibit pericentromeric CHG hypermethylation, and/or CHH hypermethylation, and/or CG hypermethlation of various discrete or localized chromosomal regions. Such discrete or localized hypermethylation is distinct from generalized hypermethylation across chromosomes that have been previously observed (U.S. Pat. No. 6,444,469). Such CHG hypermethylation or CHH hypermethylation is understood to be methylation at the sequence "CHG" or "CHH" where H=A, T, or C. Such CG, CHG, and CHH hypermethylation can be assessed by comparing the methylation status of a sample from rootstocks, scions of plants grafted to root stocks, plants, or their progeny, that had been subjected to suppression of plastidic MSH1 in the presence of mitochondrial-targeted MSH1, or a sample from progeny plants or seed derived therefrom, to a sample from control plants or seed that had not been subjected to suppression of plastidic MSH1 in the presence of mitochondrial-targeted MSH1 target gene. In this and certain other contexts, such control plants include, but are not limited to, plants, grafted plants, scions thereof and rootstocks thereof that had not been subjected to suppression of plastidic MSH1 in the presence of mitochondrial-targeted MSH1. In certain embodiments, such aforementioned changes in the methylation patterns exhibited by plants, progeny thereof, scions that are grafted to the rootstocks, or exhibited by a plant cell, a seed, a progeny plant, plant populations, seed populations, and/or processed products obtained from the grafted plant, be used to monitor the effectiveness of the graft in transmitting desirable epigenetic changes or to identify a plant cell, a seed, a progeny plant, plant populations, seed populations, and/or processed products obtained from the plant or grafted plant.

Also provided herein are various methods for producing a plant exhibiting a useful trait that comprise crossing plants that had been subjected to suppression of plastidic MSH1 in the presence of mitochondrial-targeted MSH1 or grafted plants comprising a scion grafted to rootstock that had been subjected to suppression of plastidic MSH1 in the presence of mitochondrial-targeted MSH1, or their progeny, with a second plant, and selecting one or more progeny plants obtained from the cross for an improvement in the useful trait in comparison to a control plant. In certain embodiments, the second plant or its progenitor or rootstock if a grafted plant, can be subjected to or derived from a progenitor subjected to suppression of MSH1 or of plastidic MSH1 in the presence of mitochondrial-targeted MSH1. Such second plants can be plants that were selected for a useful trait and that were progeny of any plant or grafted plant that had subjected to suppression of MSH1 or of plastidic MSH1 in the presence of mitochondrial-targeted MSH1. Control plants used as comparators to identify progeny of the cross that exhibit an improvement in the useful trait include, but are not limited to: progeny of a cross between a plant which lacks a graft to the rootstock and a plant that is isogenic to the second plant, progeny of a self of a plant that lacks a graft to the rootstock, progeny of a self of the second plant; progeny of a cross between a plant that is isogenic to the plant source of the scion of the grafted plant and a plant that is isogenic to the second plant; and, progeny of a cross between a plant that is isogenic to the plant source of the scion of the grafted plant and that is isogenic to the plant source of a scion of the second plant when the second plant is a grafted plant. Also provided are methods where at least the first plant or the scion of the first plant is from a different heterotic group than the second plant or where at least the first plant or scion of the first plant is from the same heterotic group than the second plant.

Also provided herein are various methods for producing a plant exhibiting a useful trait that comprise selfing plants that had been subjected to suppression of plastidic MSH1 in the presence of mitochondrial-targeted MSH1 or grafted plants comprising a scion grafted to rootstock that had been subjected to suppression of plastidic MSH1 in the presence of mitochondrial-targeted MSH1 with another plant, or selfing progeny plants obtained from the plant or grafted plant, and selecting one or more progeny plants obtained from the self for an improvement in the useful trait or that is useful for plant breeding in comparison to a control plant to produce a plant exhibiting a useful trait or that is useful for plant breeding. In certain embodiments, the selfed plant is the progeny of a parental plant that had been subjected to suppression of plastidic MSH1 in the presence of mitochondrial-targeted MSH1. In certain embodiments, the selfed plant is the progeny of a parental plant that had been subjected to suppression of plastidic MSH1 in the presence of mitochondrial-targeted MSH1 that was selected for and exhibits one or more useful traits. In certain embodiments, the selfed plant is a grafted plant where the rootstock source plant is the progeny of a parental plant that had been subjected to suppression of plastidic MSH1 in the presence of mitochondrial-targeted MSH1 and the rootstock source plant itself was selected for and exhibits one or more useful traits. Control plants used as comparators to identify progeny of the self that exhibit an improvement in the useful trait or that are useful for plant breeding include, but are not limited to: progeny of a self of a plant that was not subjected to suppression of MSH1 or of plastidic MSH1 in the presence of mitochondrial-targeted MSH1, progeny of a self of a plant which lacks a graft to the rootstock, progeny of a self of a plant that has a graft to rootstock that had not been subjected to suppression of MSH1 or of plastidic MSH1 in the presence of mitochondrial-targeted MSH1, and progeny of a self of a plant that is isogenic to the plant source of the scion of the grafted plant.

In certain embodiments, useful traits provided herein can be exhibited to a greater extent in subsequent generations of plants that are obtained from any of the plants, grafted plants, parental plants, or parental plant cells that had been subjected to suppression of plastidic MSH1 in the presence of mitochondrial-targeted MSH1 that are provided herein. As such, a given initial plant obtained from a parent plant that was subjected to suppression of plastidic MSH1 in the presence of mitochondrial-targeted MSH1 can be selfed to obtain first, second, third, or later generations of progeny that exhibit a given useful trait or that are useful for plant breeding to a greater extent in comparison to either the initial plant or in comparison to a control plant. An initial plant subjected to suppression of plastidic MSH1 in the presence of mitochondrial-targeted MSH1, or an initial grafted plant comprising a scion grafted to rootstock subjected to suppression of plastidic MSH1 in the presence of mitochondrial-targeted MSH1 or to rootstock obtained from a parent plant that had been subjected to suppression of plastidic MSH1 in the presence of mitochondrial-targeted MSH1, can be selfed to obtain first, second, third, or later generations of progeny that exhibit a given useful trait or that are useful for plant breeding to a greater extent in comparison to either the initial plant, the initial grafted plant or in comparison to a control plant. In other embodiments, a given initial plant or an initial grafted plant obtained from a parent plant that was subjected to suppression of plastidic MSH1 in the presence of mitochondrial-targeted MSH1 can be outcrossed to obtain F1, F2, F3, or later generations of progeny that exhibit a given useful trait or that are useful for plant breeding to a greater extent in comparison to either the initial plant or in comparison to a control plant. In certain embodiments, a useful trait harbored by an initial plant or an initial grafted plant is not exhibited, or is exhibited to a lesser degree extent, in the initial plant or an initial grafted plant. However, the useful trait harbored by such an initial plant or an initial grafted plant is exhibited or is exhibited to a greater extent in progeny obtained by outcrossing the initial plant or the initial grafted plant to another plant. A useful trait harbored by such an initial plant or an initial grafted plant can also be exhibited or is exhibited to a greater extent in progeny obtained by selfing the initial plant or the initial grafted plant. In certain embodiments, plants or grafted plants that are selfed or outcrossed can be inbred lines. In certain embodiments, a useful trait harbored by an inbred line is not exhibited, or is exhibited to a lesser degree extent, in the inbred line. However, the useful trait harbored by such inbred lines is exhibited or is exhibited to a greater extent in progeny obtained by outcrossing the inbred line to another plant. An initial plant or an initial grafted plant comprising a scion grafted to rootstock subjected to suppression of plastidic MSH1 in the presence of mitochondrial-targeted MSH1 or to rootstock obtained from a parent plant that had been subjected to suppression of plastidic MSH1 in the presence of mitochondrial-targeted MSH1 can be outcrossed to obtain F1, F2, F3, or later generations of progeny that exhibit a given useful trait to a greater extent in comparison to either the initial plant or the initial grafted plant or in comparison to a control plant. Outcrosses of such initial plants or grafted plants can be to isogenic plants or to genetically distinct plants. In the methods provided herein, initial or subsequent generations of progeny obtained from such selfs or crosses can thus be selected for useful traits. The methods provided herein also permit the identification of plants that harbor, but do not necessarily exhibit to a full extent, various useful traits. In certain embodiments, methods provided herewith involve suppression of plastidic MSH1 in the presence of mitochondrial-targeted MSH1, restoring expression of a fully functional plant MSH1 target gene, and selecting progeny plants that exhibit one or more useful traits or that are useful for plant breeding. In certain embodiments, these useful traits are associated with either one or more altered chromosomal loci that have undergone a heritable and reversible epigenetic change.

Mitochondria have up to 2000 proteins imported from nuclear genes. Most of these have a peptide presequence that targets these proteins for import into the mitochondria. Methods of identifying nuclear localized genes with mitochondrial targeting sequences (Liu et al., 2009 Mol Biol Evol. 2009 April; 26(4):875-91) and software programs that predict mitochondrial targeting sequences and their cleavage sites MITOPROT (Claros et al., Eur J Biochem 2006; 241:779-786) and TARGETP v.1.1 (Emanuelsson et al., J Mol Biol 2000; 300:1005-1016.) are available. Additionally, proteome analyses have identified many mitochondrial localized proteins in wheat (Jacoby et al., J Proteome Res. 2010 Dec. 3; 9(12):6595-604; Jacoby et al., J Proteome Res. 2013 Nov. 1; 12(11):4807-29); and the precise cleavage sites of the presequence peptide was determined for 52 proteins for rice and 62 for *Arabidopsis* (Huang et al., Plant Physiol. 2009 July; 150(3):1272-85; and Huang et al., Front Plant Sci. 2013; 4: 16). 385 mitochondrial proteins of *Arabidopsis* have been identified (Berglund et al., Mol Plant. 2009 November; 2(6):1298-309). Plant experimental systems for determing the specificity of mitochondrial vs plastid targeting and uptake of proteins are available (Xu et al., Plant Physiol. 2012 June; 159(2):710-20).

Sequences of MSH1 target genes from other plants including, but not limited to, cotton, canola, wheat, barley, flax, oat, rye, turf grass, sugarcane, alfalfa, banana, broccoli, cabbage, carrot, cassava, cauliflower, celery, citrus, a cucurbit, *eucalyptus*, garlic, grape, onion, lettuce, pea, peanut, pepper, potato, poplar, pine, sunflower, safflower, soybean, blackberry, blueberry, sugar beet, sweet potato, tobacco, strawberry, sugar beet, sweet potato, *Jatropha, Camelina,* and *Agave* can be obtained by a variety of techniques and used for suppression of plastidic MSH1 in the presence of mitochondrial-targeted MSH1 target gene in those plants. Methods for obtaining sequences for suppression of plastidic MSH1 in the presence of mitochondrial-targeted MSH1 target genes for various plants include, but are not limited to, techniques such as: i) searching amino acid (e.g., Table 1) and/or nucleotide sequence databases comprising sequences from the plant species to identify the MSH1 target genes by sequence identity comparisons; ii) cloning the MSH1 target gene by either PCR from genomic sequences or RT-PCR from expressed RNA; iii) cloning the MSH1 target gene from a genomic or cDNA library using PCR and/or hybridization based techniques; iv) cloning the MSH1 target gene from an expression library where an antibody directed to the MSH1 target gene protein is used to identify the MSH1 target gene containing clone; v) cloning the MSH1 target gene by complementation of an MSH1 target gene mutant; or vi) any combination of (i), (ii), (iii), (iv), and/or (v). Non-limiting examples of MSH1 protein sequences, from which the DNA or cDNA sequences can be identified in databases or experimentally are in Table 1 of Example 2. The DNA sequences of the target genes can be obtained from the promoter regions or transcribed regions of the target genes by PCR isolation from genomic DNA, or PCR of the cDNA for the transcribed regions, or by commercial synthesis of the DNA sequence. RNA sequences can be chemically synthesized or, more preferably, by transcription of suitable DNA templates. Recovery of the MSH1 target gene from the plant can be readily determined or confirmed by constructing a plant transformation vector that provides for suppression of the gene, transforming the plants with the vector, and determining if plants transformed with the vector exhibit the characteristic responses that are typically observed in various plant species when MSH1 expression is suppressed that include leaf variegation, cytoplasmic male sterility (CMS), a reduced growth-rate phenotype, and/or delayed or non-flowering phenotype. The characteristic responses of MSH1 suppression have been described previously as developmental reprogramming or "MSH1-dr" (Xu et al. Plant Physiol. Vol. 159:711-720, 2012).

It is anticipated that suppression the MSH1 target gene nucleic acid fragments with of 18 to 20 nucleotides, but more preferably 21 nucleotides or more, can be used to effect suppression of the endogenous MSH1 target gene. In certain embodiments, suppression of MSH1 in the presence of mitochondrial-targeted MSH1 target gene nucleic acid fragments of at least 18, 19, 20, or 21 nucleotides to about 50, 100, 200, 500, or more nucleotides can be used to effect suppression of the MSH1 target gene. Regions of 15, 20, 50, 100, 500, or more nucleotides are suitable for this purpose, with lengths of 100 to 300 bases of the target gene sequences preferable, and lengths of 300 to 500 bp or more being most preferable. In certain embodiments, regions of 15, 20, 50, or 100 to 200, 300, 500, 750, or a 1000 or more nucleotides are used to effect suppression of the MSH1 target gene. For use in a hairpin or inverted repeat knockdown design, either directly targeting MSH1 sequences or indirectly through the use of an adjacent hairpin sequence as described in U.S. Pat. No. 7,109,393, a spacer region with a sequence not related to the sequence of the genome of the target plant can be used. A hairpin construct containing 15 to 200, 200 to 300, or 300 to 500 bp or more of a target gene sequence in the antisense orientation, followed by a spacer region whose sequence is not critical but can be an intron or non-intron. If the spacer is an intron, the caster bean catalase intron which is effectively spliced in both monocots and dicots (Tanaka, Mita et al. Nucleic Acids Res 18(23): 6767-6770, 1990), is known to those skilled in the art and is useful for the present embodiment. After the spacer the same target gene sequence in the sense orientation is present, such that the antisense and sense strands can form a double stranded RNA after transcription of the transcribed region. The target gene sequences are followed by a polyadenylation region. 3' polyadenylation regions known to those skilled in the art to function in monocots and dicot plants include but are not limited to the Nopaline Synthase (NOS) 3' region, the Octapine Synthase (OCS) 3' region, the Cauliflower Mosaic Virus 35S 3' region, and the Mannopine Synthase (MAS) 3' region. Additional 3' polyadenylation regions from monocotyledonous genes such as those from rice, sorghum, wheat, and maize are available to those skilled in the art to provide similar polyadenylation region and function in DNA constructs in the present embodiments. In certain embodiments, a transgene designed to suppress a target gene in dicots is designed to have the following order of operably linked DNA elements: promoter/antisense to target gene/ catalase intron/sense target gene/polyadenylation region. In embodiments where a transgene is designed to suppress a target gene in monocots it can have the following order of operably linked DNA elements: promoter/intron for monocots/antisense to target gene/catalase intron/sense to target gene/polyadenylation region.

Sequences that provide for suppression of a MSH1 target gene can include sequences that exhibit complementarity to either strand of the promoter, 5' or 3' untranslated regions, introns, coding regions, and/or any combination thereof. A target gene promoter region for gene suppression can include the transcription start site, the TATA box, and upstream regions. The promoter region for gene silencing can be about 20, 50, 80, or 100 nucleotides in length, and more preferably is about 100 to 500 nucleotides in length. The promoter region used for such suppression can be from different regions in the upstream promoter, preferably containing at least about 500 nucleotides upstream from the start of transcription, and most preferably containing at least about 500 nucleotides upstream from the start of translation of the native coding region of the native gene. This can include the UTR which may or may not be part of the promoter. A description of various recombinant DNA constructs that target promoter and/or adjoining regions of target genes are described in U.S. Pat. No. 8,293,975. For gene targets with closely related family members, sense, antisense or double hairpin suppression designs can include sequences from more than one family member, following the designs described above In one exemplary and non-limiting embodiment, progeny plants can be obtained by selfing a plant that is heterozygous for the transgene that provides for suppression of plastidic MSH1 in the presence of mitochondrial-targeted MSH1 target gene segregation. Selfing of such heterozygous plants (or selfing of heterozygous plants regenerated from plant cells) provides for the transgene to segregate out of a subset of the progeny plant population. Where a plant wherein MSH1, in the presence of mitochondrial-targeted MSH1, is suppressed by use of a recessive mutation in an endogenous MSH1 target gene, in yet another exemplary and non-limiting embodiment, said plant can be crossed to wild-type plants that had not been subjected to suppression of MSH1 and then selfed to obtain progeny plants that are homozygous for a functional, wild-type MSH1 target gene allele. In other embodiments, suppression of MSH1 in a target plant or plant that express mitochondrial-targeted MSH1 target gene are recovered by molecular genetic techniques and produce progeny or vegetatively propagated plants derived from progenitor cells suppressed for MSH1 in the presence of mitochondrial targeted MSH1. Non limiting and exemplary embodiments of such molecular genetic techniques include: i) downregulation of MSH1 in the presence of mitochondrial-targeted MSH1 under the control of a regulated promoter(s) by withdrawal of an inducer required for activity of that promoter(s) or introduction of a repressor of that promoter(s); or, ii) exposure of the an MSH1 target gene suppressing transgene flanked by transposase or recombinase recognition sites to the cognate transposase or recombinase that provides for removal of that transgene.

Plants or rootstocks subjected to suppression of plastidic MSH1 in the presence of mitochondrial-targeted MSH1, and scions grafted to such rootstocks, as well as the progeny thereof, can exhibit a variety of nuclear chromosomal DNA methylation patterns that are absent from control plants, rootstocks, or scions that were not subjected to suppression of plastidic MSH1 in the presence of mitochondrial-targeted MSH1. Such methylation patterns can include, but are not limited to, CG hypermethylation, pericentromeric CHG or CHH hypermethylation, and/or additional characteristic methylation patterns observed in plants or progeny thereof that had been subjected to suppression of MSH1 gene expression. Such methylation patterns can also include, but are not limited to, changes in 5-hydroxymethylation and in particular, the occurrence of 5-hydroxymethylcytosine (5-hmC). Changes in 5-hmC can be monitored by immunoassays (Quest 5-hmC™ DNA ELISA Kit, Zymo Research Corp., Irvine, Calif., USA; or EpiSeeker™ hydroxymethylated DNA Quantification Kit, Abcam, Inc., Cambridge, Mass.). It is anticipated that plants, plant parts, processed plant products, rootstocks, and scions provided herein or produced by the methods provided herein can be identified by comparing methylation patterns in the genomic DNA of such materials to the methylation patterns of control plants, plant parts, processed plant products, rootstocks, and scions.

In certain embodiments of the methods provided herein, progeny plants derived from plants where suppression of plastidic MSH1 in the presence of mitochondrial-targeted MSH1 that do not exhibit any MSH1-dr phenotypes are obtained and maintained as independent breeding lines or as populations of plants that exhibit, contain, or harbor useful traits with nuclear and/or maternal inheritance or are useful for plant breeding. Useful traits that exhibit nuclear and/or maternal inheritance can thus occur in progeny plants derived from either selfs or crosses of plants that had been subjected to suppression of plastidic MSH1 in the presence of mitochondrial-targeted MSH1 but that did not exhibit any of the MSH1-dr phenotypes. More specifically, a plant that is subjected to suppression of plastidic MSH1 in the presence of mitochondrial-targeted MSH1 that exhibits a wild type phenotype, a more robust growth habit, or even an improvement in a useful trait or that is useful for plant breeding in comparison to a control plant that had not been subjected to suppression of plastidic MSH1 in the presence of mitochondrial-targeted MSH1 can exhibit, contain, or harbor useful traits with nuclear and/or maternal inheritance. In certain embodiments, the useful traits that are exhibited, contained, or harbored in such plants that do not exhibit any MSH1-dr phenotypes can be transmitted to progeny plants by selfing or outcrossing. In certain embodiments, the useful traits that are exhibited, contained, or harbored in such plants that do not exhibit any MSH1-dr phenotypes can be transmitted to a scion and its progeny by a rootstock graft of a plant or its progenitor that are subjected to suppression of plastidic MSH1 in the presence of mitochondrial-targeted MSH1. It is further contemplated that such individual lines that have the useful traits can be obtained by any of the aforementioned genetic techniques, molecular genetic techniques, or combinations thereof. Individual lines or populations of plants obtained from plants subjected to suppression of plastidic MSH1 in the presence of mitochondrial-targeted MSH1 that have useful traits but that do not exhibit any MSH1-dr phenotypes can be crossed to other plants to obtain progeny plants that exhibit the useful trait. In certain embodiments, the plants subjected to suppression of plastidic MSH1 in the presence of mitochondrial-targeted MSH1 that have useful traits but that do not exhibit any MSH1-dr phenotypes exhibit a wild type phenotype, a more robust growth habit, or even an improvement in a useful trait or that are useful for plant breeding, in comparison to a control plant that had not been subjected to suppression of plastidic MSH1 in the presence of mitochondrial-targeted MSH1, can exhibit, contain, or harbor useful traits with nuclear and/or maternal inheritance. In certain embodiments, progeny of such outcrosses can be selfed to obtain individual progeny lines that exhibit significant phenotypic variation. Certain individual progeny plant lines obtained from the outcrosses of plants subjected to suppression of plastidic MSH1 in the presence of mitochondrial-targeted MSH1 to other plants can exhibit useful phenotypic variation where one or more traits are improved relative to either parental line and can be selected. Such selected individual lines with the useful trait or that are useful for plant breeding can either be bred (i.e. crossed or selfed) individually or as a population. Useful phenotypic variation that can be selected in such individual progeny lines includes, but is not limited to, increases in fresh and dry weight biomass relative to either parental line and/or increases in seed yield. Such selected individual lines with the useful trait or that are useful for plant breeding can either be bred (i.e. crossed or selfed) individually or as a population. In certain embodiments, the selected individual plants are crossed or selfed as a collected group of two or more selected plants to obtain populations of progeny plants that are enriched for the trait. In certain embodiments, about 1% to about 45% of the population of progeny plants are selected for the useful trait or that are useful for plant breeding and subsequently crossed or selfed to obtain progeny plant populations that are enriched for useful trait(s). Individual lines or populations of plants obtained from plants, where suppression of plastidic MSH1 in the presence of mitochondrial-targeted MSH1 occurred, that have useful traits can also be selfed to obtain progeny plants that exhibit, contain, or harbor useful traits or are useful for plant breeding. In certain embodiments, the plants subjected to suppression of plastidic MSH1 in the presence of mitochondrial-targeted MSH1 that have useful traits but that do not exhibit any MSH1-dr phenotypes exhibit a wild type phenotype, a more robust growth habit, or even an improvement in a useful trait or that are useful for plant breeding in comparison to a control plant that had not been subjected to suppression of plastidic MSH1 in the presence of mitochondrial-targeted MSH1, can exhibit, contain, or harbor useful traits with nuclear and/or maternal inheritance. Recovery of such progeny plants that lack the undesirable phenotypes can in certain embodiments be facilitated by removal of the transgene(s) or endogenous mutant or altered locus/loci that provides for suppression of plastidic MSH1 in the presence of mitochondrial-targeted MSH1. In certain embodiments, progeny of such selfs can be used to obtain individual progeny lines or populations that exhibit significant phenotypic variation. Certain individual progeny plant lines or populations obtained from selfing plants where suppression of plastidic MSH1 in the presence of mitochondrial-targeted MSH1 can exhibit useful phenotypic variation where one or more traits are improved relative to the parental line that was not subjected to suppression of plastidic MSH1 in the presence of mitochondrial-targeted MSH1 can be selected. Such selected individual lines with the useful trait or that are useful for plant breeding can either be bred (i.e. crossed or selfed) individually or as a population. Useful phenotypic variation that can be selected in such individual progeny lines includes, but is not limited to, increases in fresh and dry weight biomass relative to the parental line. Such selected individual lines with the useful trait or that are useful for plant breeding can either be bred (i.e. crossed or selfed) individually or as a population. In certain embodiments, the selected individual plants are crossed or selfed as a collected group of two or more selected plants to obtain populations of progeny plants that are enriched for the trait. In certain embodiments, about 1% to about 45% of the population of progeny plants are selected for the useful trait or that are useful for plant breeding and subsequently crossed or selfed to obtain progeny plant populations that are enriched for useful trait(s). In certain embodiments, an outcross of an individual line or lines exhibiting, containing, or harboring the useful traits can be to a plant or plants that have not been subjected to suppression of MSH1 or of plastidic MSH1 in the presence of mitochondrial-targeted MSH1 but are otherwise isogenic to the individual line or lines. In certain exemplary embodiments, a line or lines exhibiting, containing, or harboring the useful traits is obtained by suppression of plastidic MSH1 in the presence of mitochondrial-targeted MSH1 in a given germplasm and can be outcrossed to a plant having that same germplasm that was not subjected to suppression of MSH1 or of plastidic MSH1 in the presence of mitochondrial-targeted MSH1. In other embodiments, an outcross of an individual line or lines exhibiting, containing, or harboring the useful traits can be to a plant or plants that have not been subjected to suppression of MSH1 or of plastidic MSH1 in the presence of mitochondrial-targeted MSH1 but are not isogenic to the individual line(s). Thus, in certain embodiments, an outcross of an individual line or lines exhibiting, containing, or harboring the useful traits can also be to a plant or plants that comprise one or more chromosomal polymorphisms that do not occur in the individual line(s), to a plant or plants derived from partially or wholly different germplasm, or to a plant or plant of a different heterotic group (in instances where such distinct heterotic groups exist). It is also recognized that such an outcross can be made in either direction. Thus, an individual line exhibiting useful traits or that is useful for plant breeding can be used as either a pollen donor or a pollen recipient to a plant that has not been subjected to suppression of MSH1 or of plastidic MSH1 in the presence of mitochondrial-targeted MSH1 in such outcrosses. In certain embodiments, the progeny of the outcross are then selfed to establish individual lines that can be separately screened to identify lines with improved traits relative to parental lines. Such individual lines that exhibit the improved traits are then selected and can be propagated by further selfing. In certain embodiments, the methods provided herein can comprise selecting one or more progeny plants having the useful trait or that are useful for plant breeding that exhibit nuclear and/or maternal inheritance. Nuclear inheritance can be established by demonstrating that the trait is pollen transmissible. Nuclear inheritance can also be established by demonstrating that the trait is associated with one or more chromosomal alterations that are present in the plants, grafted plants, or progeny thereof subjected to suppression of plastidic MSH1 in the presence of mitochondrial-targeted MSH1 but that are absent from control plants that had not been subjected to such suppression of MSH1 or of plastidic MSH1 in the presence of mitochondrial-targeted MSH1. In certain embodiments, sub-populations of plants comprising the useful traits and epigenetic changes induced by suppression of plastidic MSH1 in the presence of mitochondrial-targeted MSH1 can be selected and bred as a population. Such populations can then be subjected to one or more additional rounds of selection for the useful traits and/or epigenetic changes to obtain subsequent sub-populations of plants exhibiting the useful trait. Any of these sub-populations can also be used to generate a seed lot. In an exemplary embodiment suppression of plastidic MSH1 in the presence of mitochondrial-targeted MSH1 in plants that do not exhibit an MSH1-dr phenotype can be selfed (S1) or outcrossed (F1) to obtain a S1 or F1 generation. A bulk selection at the F1/S1, F2/S2, and/or F3/S3 generation can thus provide a population of plants exhibiting the useful trait or that are useful for plant breeding and/or epigenetic changes or for producing a seed lot. In certain embodiments, it is also anticipated that populations of progeny plants or progeny seed lots comprising a mixture of inbred and hybrid germplasms can be derived from populations comprising hybrid germplasm (i.e. plants arising from cross of one inbred line to a distinct inbred line). In certain embodiments, such sub-populations can comprise plants that had been subjected to suppression of plastidic MSH1 in the presence of mitochondrial-targeted MSH1 or grafted plants comprising a scion grafted to rootstock that had been subjected to suppression of plastidic MSH1 in the presence of mitochondrial-targeted MSH1. Sub-populations of plants or grafted plants where the plant or the rootstock source plant is the progeny of a parental plant that had been subjected to suppression of plastidic MSH1 in the presence of mitochondrial-targeted MSH1 and that was selected for one or more useful traits can also be selected and bred as a population. Any of the aforementioned subpopulations can comprise 2 or more, 10 or more, 50 or more, 100 or more, 1000 or more, or 10,000 or more plants. Seed lots thus obtained from these exemplary method or other methods provided herein can comprise seed wherein at least 25%, 50%, 60%, 70%, 80%, 90%, or 95% of progeny plants grown from the seed exhibit a useful trait. The selection would provide the most robust and vigorous of the population for seed lot production. Seed lots produced in this manner could be used for either breeding or sale. In certain embodiments, a seed lot comprising seed wherein at least 25%, 50%, 60%, 70%, 80%, 90%, or 95% of progeny plants grown from the seed exhibit a useful trait or that are useful for plant breeding associated with one or more epigenetic changes, wherein the epigenetic changes are associated with CG hyper-methylation and/or CHG and/or CHH hyper-methylation at, or sRNA derived from, one or more nuclear chromosomal loci in comparison to a control plant that does not exhibit the useful trait, and wherein the seed or progeny plants grown from said seed that is epigenetically heterogenous are obtained. A seed lot obtainable by these methods can include at least 100, 500, 1000, 5000, or 10,000 seeds. In certain embodiments, methods for producing a seed lot comprising: (i) growing a population of plants, wherein said population comprises two or more plants that had been subjected to suppression of plastidic MSH1 in the presence of mitochondrial-targeted MSH1, two or more grafted plants comprising a scion and rootstock obtained from a plant that had been subjected to suppression of plastidic MSH1 in the presence of mitochondrial-targeted MSH1, or two or more plants from a parental plant that had been subjected to suppression of plastidic MSH1 in the presence of mitochondrial-targeted MSH1; and (ii) obtaining a seed lot from the population are provided. Populations of grafted plants where the rootstock source plant is the progeny of a parental plant that had been subjected to suppression of plastidic MSH1 in the presence of mitochondrial-targeted MSH1 and that was selected for one or more useful traits can also be selected and bred as a population. Any of the aforementioned populations can comprise 2 or more, 10 or more, 50 or more, 100 or more, 1000 or more, or 10,000 or more plants. Seed lots thus obtained from these exemplary methods or other methods provided herein can comprise seed wherein at least 25%, 50%, 60%, 70%, 80%, 90%, or 95% of progeny plants grown from the seed exhibit a useful trait. The selection would provide the most robust and vigorous of the population for seed lot production. Seed lots produced in this manner could be used for either breeding or sale. In certain embodiments, a seed lot comprising seed wherein at least 25%, 50%, 60%, 70%, 80%, 90%, or 95% of progeny plants grown from the seed exhibit a useful trait or that is useful for plant breeding associated with one or more epigenetic changes, wherein the epigenetic changes are associated with CG hyper-methylation and/or CHG and/or CHH hyper-methylation at, or sRNA derived from, one or more nuclear chromosomal loci in comparison to corresponding nuclear chromosomal loci of a control plant that does not exhibit the useful trait, and wherein the seed or progeny plants grown from said seed that is epigenetically heterogenous are obtained. A seed lot obtainable by these methods can include at least 100, 500, 1000, 5000, or 10,000 seeds.

Altered chromosomal loci that can confer useful traits can also be identified and selected by performing appropriate comparative analyses of control plants that do not exhibit the useful traits and test plants obtained from a parental plant or plant cell that had been subjected to suppression of plastidic MSH1 in the presence of mitochondrial-targeted MSH1 and obtaining either the altered loci or plants comprising the altered loci. It is anticipated that a variety of control plants and test plants can be used in such comparisons and selections. In certain embodiments, the control plants that do not exhibit the useful trait include, but are not limited to, any of: a) a wild-type plant; b) a distinct subpopulation of plants within a given F2 population of plants of a given plant line (where the F2 population is any applicable plant type or variety); c) an F1 population exhibiting a wild type phenotype (where the F1 population is any applicable plant type or variety); and/or, d) a plant that is isogenic to the parent plants or parental cells of the test plants prior to suppression of plastidic MSH1 in the presence of mitochondrial-targeted MSH1 in those parental plants or plant cells (i.e. the control plant is isogenic to the plants or plant cells that were later subjected to suppression of plastidic MSH1 in the presence of mitochondrial-targeted MSH1 to obtain the test plants). In certain embodiments, the test plants that exhibit the useful trait or that are useful for plant breeding include, but are not limited to, any of: a) any non-transgenic segregants that exhibit the useful trait or that are useful for plant breeding and that were derived from parental plants or plant cells that had been subjected to suppression of plastidic MSH1 in the presence of mitochondrial-targeted MSH1, b) a distinct subpopulation of plants within a given F2 population of plants of a given plant line that exhibit the useful trait or that are useful for plant breeding (where the F2 population is any applicable plant type or variety); (c) any progeny plants obtained from the plants of (a) or (b) that exhibit the useful trait; or d) a plant or plant cell that had been subjected to suppression of plastidic MSH1 in the presence of mitochondrial-targeted MSH1 that exhibit the useful trait.

In general, an objective of these comparisons is to identify differences in the small RNA profiles and/or methylation of certain chromosomal DNA loci between test plants that exhibit the useful traits and control plants that do not exhibit the useful traits. Altered loci thus identified can then be isolated or selected in plants to obtain plants exhibiting the useful traits or that are useful for plant breeding. In certain embodiments, altered chromosomal loci can be identified by identifying small RNAs that are up or down regulated in the test plants (in comparison to control plants). This method is based in part on identification of altered chromosomal loci where small interfering RNAs direct the methylation of specific gene targets by RNA-directed DNA methylation (RdDM). The RNA-directed DNA methylation (RdDM) process has been described (Chinnusamy V et al. Sci China Ser C-Life Sci. (2009) 52(4): 331-343; Bond et. al., Trends Cell Biol. 2014 Feb. 24(2): 100-7). Any applicable technology platform can be used to compare small RNAs in the test and reference plants, including, but not limited to: microarray-based methods (Franco-Zorilla et al. Plant J. 200959(5): 840-50); deep sequencing based methods (Wang et al. The Plant Cell 21:1053-1069(2009); Wei et al., Proc Natl Acad Sci USA. 2014 Feb. 19, 111(10): 3877-3882; Zhai et al., Methods. 2013 Jun. 28. pii: S1046-2023(13)00237-5. doi: 10.1016/j.ymeth.2013.06.025 or J. Zhai et al., Methods (2013), http internet site dx.doi.org/10.1016/j.ymeth.2013.06.025; U.S. Pat. Nos. 7,550,583; 8,399,221; 8,399,222; 8,404,439; 8,637,276; Rosas-Cárdenas et al., (2011) *Plant Methods* 2011, 7:4; Moyano et al., BMC Genomics. 2013 Oct. 11; 14:701; Eldem et al., PLoS One. 2012; 7(12):e50298; Barber et al., Proc Natl Acad Sci USA. 2012 Jun. 26; 109(26):10444-9; Gommans et al., Methods Mol Biol. 2012; 786:167-78; and the like. DNA methylation and sRNAs corresponding to these regions can change in progeny plants when two parent plants are crossed. Tomato progeny plants from a cross displayed transgressive sRNAs that were more abundant in the progeny than in either parent (Shivaprasad et al., EMBO J. 2012 Jan. 18; 31(2):257-66). A cross between two maize lines, B73 and Mo17, yielded paramutation type switches of the DNA methylation pattern of one parent chromosome being switched to that of the other parental chromosome at the corresponding loci (Regulski et al., Genome Res. 2013 October; 23(10):1651-62). A cross between *Arabidopsis* plants produced progeny wherein the DNA methylation patterns of one parental chromosome were imposed onto the other parental chromosome, either gaining or losing DNA methylation levels (Greaves et al., Proc Natl Acad Sci USA. 2014 Feb. 4; 111(5):2017-22). These non-limiting examples indicate DNA methylation patterns can be more complex than additive patterns from the parents. Accordingly, an objective is to identify new combinations of altered chromosomal loci in progeny plants that have new patterns of DNA methylation and of sRNA profiles. New combinations of altered chromosomal loci can result both from segregation of altered chromosomal loci in the progeny as well as due to changes in DNA methylation and sRNA profiles due to transgressive, paramutation type switching, and other biological processes. In certain embodiments, altered chromosomal loci are derived from a parental plant subjected to suppression of plastidic MSH1 in the presence of mitochondrial-targeted MSH1. In certain embodiments, altered chromosomal loci are derived from the formation of new patterns of DNA methylation and sRNA levels from the interaction of altered chromosomal loci derived from a parental plant subjected to suppression of plastidic MSH1 in the presence of mitochondrial-targeted MSH1 with chromosomal loci from a second plant. Said second plant can be from a parental plant subjected to suppression of MSH1 or of plastidic MSH1 in the presence of mitochondrial-targeted MSH1 or from a parental plant not subjected to suppression of MSH1 or suppression of plastidic MSH1 in the presence of mitochondrial-targeted MSH1. Crossing parental lines both previously subjected to suppression MSH1 and/or of plastidic MSH1 in the presence of mitochondrial-targeted MSH1 and containing different groupings of altered chromosomal loci provides a method of creating new combinations of altered chromosomal loci.

In certain embodiments, altered chromosomal loci can be identified by identifying chromosomal regions (genomic DNA) that have an altered methylation status in the test plants (in comparison to a reference plant). An altered methylation status can comprise either the presence or absence of methylation in one or more chromosomal loci of a test plant in comparison to a reference plant. Any applicable technology can be used to compare the methylation status of chromosomal loci in the test and reference plants. Applicable technologies for identifying chromosomal loci with changes in their methylation status include, but not limited to, methods based on immunoprecipitation of DNA with antibodies that recognize 5-methyl-cytidine, methods based on use of methylation dependent restriction endonucleases and PCR such as McrBC-PCR methods (Rabinowicz, et al. Genome Res. 13: 2658-2664 2003; Li et al., Plant Cell 20:259-276, 2008), sequencing of bisulfite-converted DNA (Frommer et al. Proc. Natl. Acad. Sci. U.S.A. 89 (5): 1827-31; Tost et al. BioTechniques 35 (1): 152-156, 2003), methylation-pericentromeric regions specific PCR analysis of bisulfite treated DNA (Herman et al. Proc. Natl. Acad. Sci. U.S.A. 93 (18): 9821-6, 1996), deep sequencing based methods (Wang et al. The Plant Cell 21:1053-1069 (2009)), methylation sensitive single nucleotide primer extension (MsSnuPE; Gonzalgo and Jones Nucleic Acids Res. 25 (12): 2529-2531, 1997), fluorescence correlation spectroscopy (Umezu et al. Anal Biochem. 415(2): 145-50, 2011), single molecule real time sequencing methods (Flusberg et al. Nature Methods 7, 461-465), high resolution melting analysis (Wojdacz and Dobrovic (2007) Nucleic Acids Res. 35 (6): e41), and the like. Additional applicable technologies for identifying chromosomal loci with changes in their DNA methylation status include, but not limited to, the preparation, amplification and analysis of Methylome libraries as described in U.S. Pat. No. 8,440,404; using Methylation-specific binding proteins as described in U.S. Pat. No. 8,394,585; determining the average DNA methylation density of a locus of interest within a population of DNA fragments as described in U.S. Pat. No. 8,361,719; by methylation-sensitive single nucleotide primer extension (Ms-SNuPE), for determination of strand-specific methylation status at cytosine residues as described in U.S. Pat. No. 7,037,650; a method for detecting a methylated CpG-containing nucleic acid present in a specimen by contacting the specimen with an agent that modifies unmethylated cytosine and amplifying the CpG-containing nucleic acid using CpG-specific oligonucleotide primers as described in U.S. Pat. No. 6,265,171; an improved method for the bisulfite conversion of DNA for subsequent analysis of DNA methylation as described in U.S. Pat. No. 8,586,302; for treating genomic DNA samples with sodium bisulfite to create methylation-dependent sequence differences, followed by detection with fluorescence-based quantitative PCR techniques as described in U.S. Pat. No. 8,323,890; a method for retaining methylation pattern in globally amplified DNA as described in U.S. Pat. No. 7,820,385; a method for detecting cytosine methylations DNA as described in U.S. Pat. No. 8,241,855; a method for quantification of methylated DNA as described in U.S. Pat. No. 7,972,784; a highly sensitive method for the detection of cytosine methylation patterns as described in U.S. Pat. No. 7,229,759; additional methods for detecting DNA methylation changes are described in U.S. Pat. Nos. 7,943,308 and 8,273,528.

Chromosomal mutations can be introduced into specific loci of a plant such as MSH1 by any applicable method. In certain embodiments, suppression of a plant's plastid function or MSH1 gene initiates epigenetic modifications to produce useful traits (see U.S. patent application Ser. No. 13/462,216, U.S. Provisional 61/863,267, U.S. Provisional 61/882,140, and U.S. Provisional 61/901,349, each of which is incorporated by reference in its entirety except that the claims and definitions sections are excluded from incorporation). MSH1 suppression can be accomplished by many methods known to those skilled in the art, including topical RNA (U.S. Patent Application Publication No# US 2014/0018241 A1), promoter silencing (Deng et al., Plant Cell Physiol. 2014 Feb. 2), or site directed methods such as CRISPR/CAS9 methods (Jiang et al., Nucleic Acids Res. 2013 Nov. 1; 41(20):e188. doi: 10.1093/nar/gkt780. Epub 2013 Sep. 2), or additional methods of homologous recombination or site directed changes (genome editing) that suppress MSH1 function. Applicable methods for introducing chromosomal mutations in endogenous plant chromosomal loci include, but are not limited to, mixed duplex oligonucleotides (U.S. Pat. Nos. 5,565,350; 5,731,181; 8,106,259, 8,268,622), homologous double stranded break repair (Wright et al., Plant J. 44, 693, 2005; D'Halluin, et al., Plant Biotech. J. 6:93, 2008), non-homologous end joining or a combination of non-homologous end joining and homologous recombination (reviewed in Puchta, J. Exp. Bot. 56, 1, 2005; Wright et al., Plant J. 44, 693, 2005), meganuclease-induced, site specific double stranded break repair (WO/06097853A1, WO/06097784A1, WO/04067736A2, U.S. 20070117128A1), TALENS and CRISPR/CAS9 systems (Straup3 and Lahaye, Mol Plant. 2013 September; 6(5):1384-7. doi: 10.1093/mp/sst075. Epub 2013 May 29.), and zinc finger nuclease mediated homologous recombination (WO 03/080809, WO 05/014791, WO 07014275, WO 08/021207). In still other embodiments, desired mutations in endogenous plant chromosomal loci can be identified through use of the TILLING technology (Targeting Induced Local Lesions in Genomes) as described (Henikoff et al., Plant Physiol. 2004, 135:630-636). In still other embodiments, desired mutations in endogenous plant chromosomal loci can be created through the use of mixed duplex oligonucleotides (U.S. Pat. Nos. 8,268,622, 8,106,259, 5,565,350, and 5,731,181). In still other embodiments, desired mutations in endogenous plant chromosomal loci can be identified through screening of collections of plants subjected to transposable element insertions for insertions into MSH1.

In certain embodiments, removal of the dual targeting sequence of one or more endogenous MSH1 genes and substituting a mitochondrial targeting sequence, such as the *Arabidopsis* AOX1 or Rice AOX1 signals, can be accomplished by homologous recombination methods known to those skilled in the art (Chen and Gao Plant Cell Rep. 2014 April; 33(4):575-83; Voytas Annu Rev Plant Biol. 2013; 64:327-50; Tzfira et al., Plant Biotechnol J. 2012 May; 10(4):373-89). A resulting plant containing one or more such substitutions would be subjected to suppression of plastidic MSH1 in the presence of mitochondrial-targeted MSH1.

The MSH1 DNA binding domain 1 is highly conserved (VLLCRVGEFYEAIGIDA), particularly in the FYE amino acid motif (Abdelnoor et al., Proc Natl Acad Sci USA. 2003 May 13; 100(10):5968-73. Epub 2003 May 1). An objective of the present disclosure is to change the FYE motif, wherein the original parent plant contains an FYE motif in the MSH1 DNA binding domain to produce, as an embodiment of the present disclosure, a plant containing a mutation in the FYE motif in the MSH1 DNA binding domain. Most preferable is a mutation changing FYE to FYA in said mutant plant. Most preferably said mutant plant is homozygous for a mutation in the FYE motif in the MSH1 DNA binding domain. A non-limiting embodiment of the present disclosure are one or more plants containing a mutation in a MSH1 gene causing a change in the FYE amino acid sequence in the DNA binding domain of MSH1. In some embodiments MSH1 genes encoding this region (FYE of the DNA binding domain) can have sequences of the type FXZ, where F is the F of the FYE motif, X is any amino acid other than tyrosine (Y), and Z is any amino acid other than E. Preferably a mutation of the type FYZ, where F is the F of the FYE motif, Y is the Y of the FYE motif, and Z is any amino acid other than E of the FYE motif. Most preferable is a mutation changing FYE to FYA.

In other embodiments, chromosomal modifications that provide for the desired genetic effect can comprise a transgene. Transgenes that can result in decreased expression of an gene by a variety of mechanisms that include, but are not limited to, dominant-negative mutants, a small inhibitory RNA (siRNA), a microRNA (miRNA), a co-suppressing sense RNA, and/or an anti-sense RNA and the like. U.S. patents incorporated herein by reference in their entireties that describe suppression of endogenous plant genes by transgenes include U.S. Pat. Nos. 7,109,393, 5,231,020 and 5,283,184 (co-suppression methods); and U.S. Pat. Nos. 5,107,065 and 5,759,829 (antisense methods). In certain embodiments, transgenes specifically designed to produce double-stranded RNA (dsRNA) molecules with homology to the endogenous gene of a chromosomal locus can be used to decrease expression of that endogenous gene. In such embodiments, the sense strand sequences of the dsRNA can be separated from the antisense sequences by a spacer sequence, preferably one that promotes the formation of a dsRNA (double-stranded RNA) molecule. Examples of such spacer sequences include, but are not limited to, those set forth in Wesley et al., Plant J., 27(6):581-90 (2001), and Hamilton et al., Plant J., 15:737-746 (1998). Vectors for inhibiting endogenous plant genes with transgene-mediated expression of hairpin RNAs are disclosed in U.S. Patent Application Nos. 20050164394, 20050160490, and 20040231016, each of which is incorporated herein by reference in their entirety. Transgenes that result in increased expression of a gene of a chromosomal locus include, but are not limited to, a recombinant gene fused to heterologous promoters that are stronger than the native promoter, a recombinant gene comprising elements such as heterologous introns, 5' untranslated regions, 3' untranslated regions that provide for increased expression, and combinations thereof. Such promoter, intron, 5' untranslated, 3' untranslated regions, and any necessary polyadenylation regions can be operably linked to the DNA of interest in recombinant DNA molecules that comprise parts of transgenes useful for making chromosomal modifications as provided herein. Exemplary promoters useful for expression of transgenes include, but are not limited to, enhanced or duplicate versions of the viral CaMV35S and FMV35S promoters (U.S. Pat. No. 5,378,619, incorporated herein by reference in its entirety), the cauliflower mosaic virus (CaMV) 19S promoters, the rice Act1 promoter and the Figwort Mosaic Virus (FMV) 35S promoter (U.S. Pat. No. 5,463,175). Exemplary introns useful for transgene expression include, but are not limited to, the maize hsp70 intron (U.S. Pat. No. 5,424,412), the rice Act1 intron (McElroy et al., 1990, The Plant Cell, Vol. 2, 163-171), the CAT-1 intron (Cazzonnelli and Velten, Plant Molecular Biology Reporter 21: 271-280, September 2003), the pKANNIBAL intron (Wesley et al., Plant J. 2001 27(6):581-90; Collier et al., 2005, Plant J 43: 449-457), the PIV2 intron (Mankin et al. (1997) Plant Mol. Biol. Rep. 15(2): 186-196) and the "Super Ubiquitin" intron (U.S. Pat. No. 6,596,925; Collier et al., 2005, Plant J 43: 449-457). Exemplary polyadenylation sequences include, but are not limited to, and *Agrobacterium* tumor-inducing (Ti) plasmid nopaline synthase (NOS) gene and the pea ssRUBISCO E9 gene polyadenylation sequences.

Plant lines and plant populations obtained by the methods provided herein can be screened and selected for a variety of useful traits by using a wide variety of techniques. In particular embodiments provided herein, individual progeny plant lines or populations of plants obtained from the selfs or outcrosses of plants where suppression of plastidic MSH1 in the presence of mitochondrial-targeted MSH1 target gene expression was suppressed to other plants are screened and selected for the desired useful traits. In certain embodiments, the screened and selected trait is improved plant yield. In certain embodiments, such yield improvements are improvements in the yield of a plant line relative to one or more parental line(s) under non-stress conditions. Non-stress conditions comprise conditions where water, temperature, nutrients, minerals, and light fall within typical ranges for cultivation of the plant species. Such typical ranges for cultivation comprise amounts or values of water, temperature, nutrients, minerals, and/or light that are neither insufficient nor excessive. In certain embodiments, such yield improvements are improvements in the yield of a plant line relative to parental line(s) under abiotic stress conditions.

Such abiotic stress conditions include, but are not limited to, conditions where water, temperature, nutrients, minerals, and/or light that are either insufficient or excessive. Abiotic stress conditions would thus include, but are not limited to, drought stress, osmotic stress, nitrogen stress, phosphorous stress, mineral stress, heat stress, cold stress, and/or light stress. In this context, mineral stress includes, but is not limited to, stress due to insufficient or excessive potassium, calcium, magnesium, iron, manganese, copper, zinc, boron, aluminum, or silicon. In this context, mineral stress includes, but is not limited to, stress due to excessive amounts of heavy metals including, but not limited to, cadmium, copper, nickel, zinc, lead, and chromium.

Improvements in yield in plant lines obtained by the methods provided herein can be identified by direct measurements of wet or dry biomass including, but not limited to, grain, lint, leaves, stems, or seed. Improvements in yield can also be assessed by measuring yield related traits that include, but are not limited to, 100 seed weight, a harvest index, and seed weight. In certain embodiments, such yield improvements are improvements in the yield of a plant line relative to one or more parental line(s) and can be readily determined by growing plant lines obtained by the methods provided herein in parallel with the parental plants. In certain embodiments, field trials to determine differences in yield whereby plots of test and control plants are replicated, randomized, and controlled for variation can be employed (Giesbrecht F G and Gumpertz M L. 2004. Planning, Construction, and Statistical Analysis of Comparative Experiments. Wiley. New York; Mead, R. 1997. Design of plant breeding trials. In Statistical Methods for Plant Variety Evaluation. eds. Kempton and Fox. Chapman and Hall. London.). Methods for spacing of the test plants (i.e. plants obtained with the methods of this disclosure) with check plants (parental or other controls) to obtain yield data suitable for comparisons are provided in references that include, but are not limited to, any of Cullis, B. et al. J. Agric. Biol. Env. Stat. 11:381-393; and Besag, J. and Kempton, R A. 1986. Biometrics 42: 231-251.). Other useful traits that can be obtained by the methods provided herein include various seed quality traits including, but not limited to, improvements in either the compositions or amounts of oil, protein, or starch in the seed. Still other useful traits that can be obtained by methods provided herein include, but are not limited to, increased biomass, non-flowering, male sterility, digestibility, seed filling period, maturity (either earlier or later as desired), reduced lodging, and plant height (either increased or decreased as desired). Still other useful traits that can be obtained by methods provided herein include, but are not limited to, delayed leaf senescence, increased flower number, improved architecture for high density planting, improved photosynthesis, increased root mass, increased cell number, improved seedling vigor, improved seedling size, increased rate of cell division, improved metabolic efficiency, and increased meristem size.

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Figure 2:
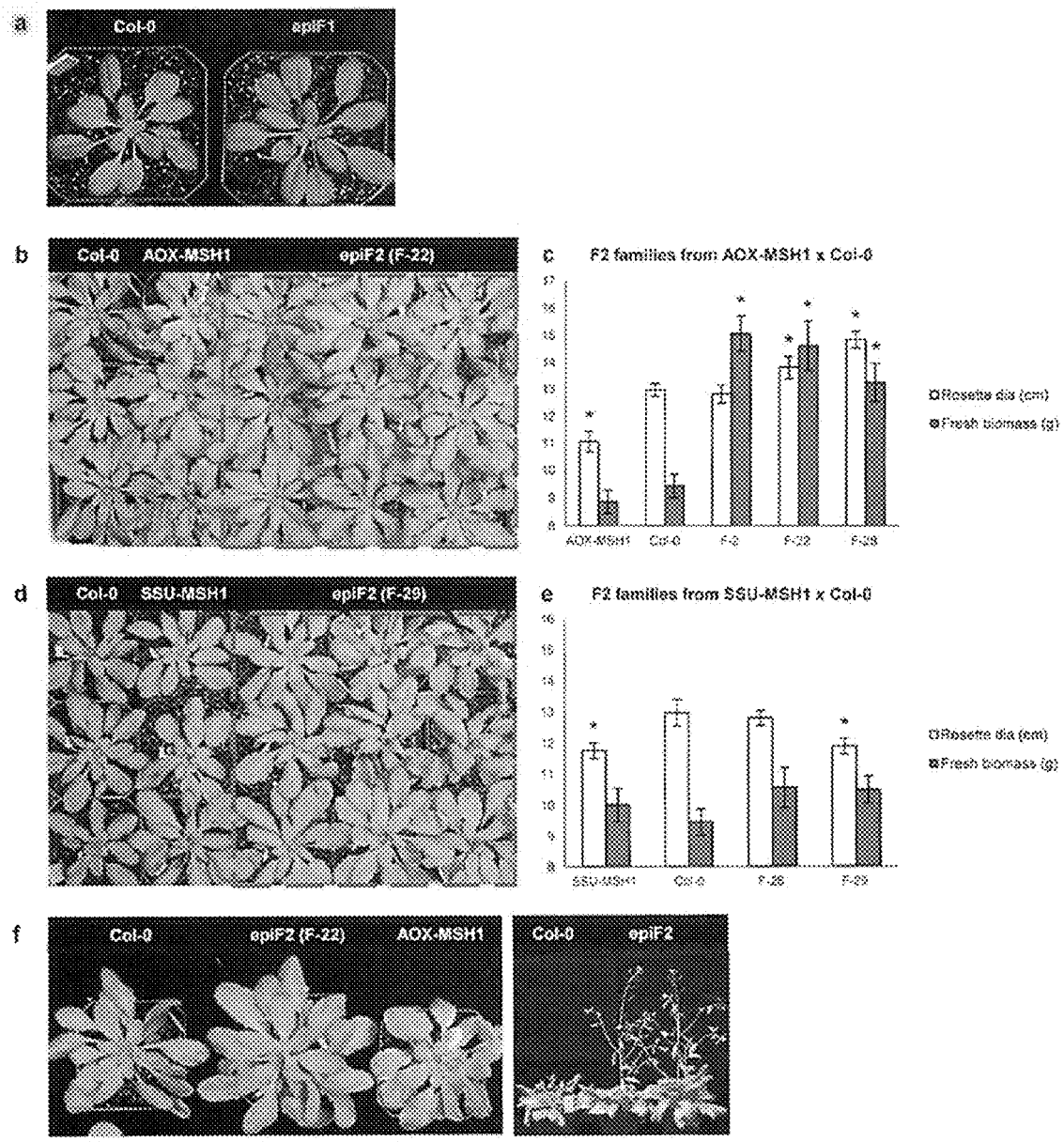
FIG. 2. MSH1-mediated enhanced growth from crossing is associated with plastid effects. a, Mitochondrial hemi-complementation line AOX-MSH1×Col-0 $F_1$. b, Mitochondrial-complemented AOX-MSH1×Col-0 $F_2$ showing enhanced growth. c, Rosette diameter and fresh biomass of AOX-MSH1-derived $F_2$ lines is significantly greater than Col-0 (* $p<0.05$). d, Plastid-complemented SSU-MSH1× Col-0 $F_2$ appears similar to wild type Col-0. e, Rosette diameter and fresh biomass of SSU-MSH1-derived $F_2$ lines compared to Col-0. f, Enhanced growth phenotype in the $F_2$ generation of AOX-MSH1×Col-0.
Figure 3:
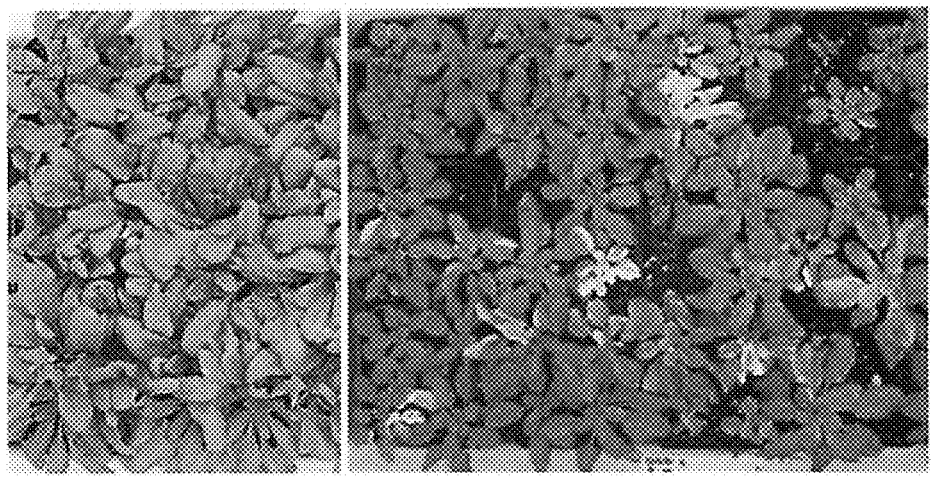
FIG. 3. Top panels: Arabidopsis Columbia 0 (Col-0) seedlings are on the left and the msh1–/– Col 0 seedlings complemented with the MSH1 FYA mutant (denoted FYE/FYA) are on the right, with indications of plant color variation due to a lack of MSH1 function in the plastids. Middle panels: the left photo shows Col-0 and control "Empty vector", which lacks any functional MSH1 gene in the msh1–/– Col 0 background, and therefore displays the small plant dr phenotype. The right panel displays plants of the msh1–/– Col 0 seedlings complemented with the MSH1 FYA mutant (denoted FYE/FYA). Note the very small plant (third from right), indicating this genotype also displays the small plant dr phenotype. Bottom panels (Mitochondrial DNA recombination assay): A PCR analysis of recombination in the mitochondrial genome. The bottom right "Col-0" sample displays a single band, indicative of no recombination in normal plants with functional MSH1 in their mitochondria. The "msh1" null sample shows two bands, indicative of recombination. The Empty vector samples display recombination (two bands) as expected for a lack of MSH1 function. The FYE/FYA plants display a single band, indicating no mitochondrial recombination is occurring, indicating the FYA mutation in MSH1 is providing functional MSH1 in the mitochondria. "T+" indicates a line is transgenic for either the empty vector or the FYA mutant gene.
Figure 3:
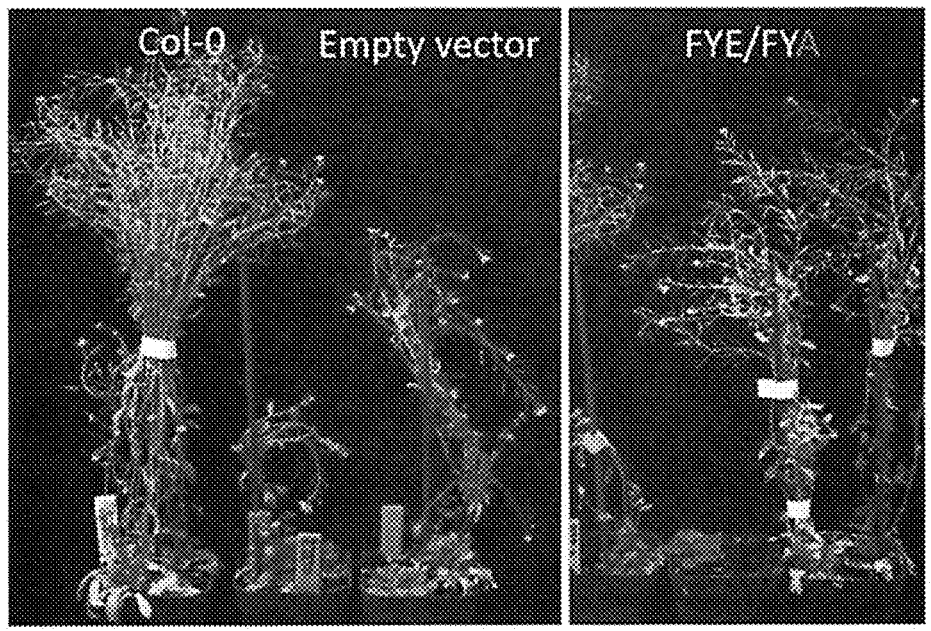
Figure 3:
Figure 3:
Figure 4:
FIG. 4. Transgenic wheat lines suppressed for MSH1 display a MSH1-dr phenotype. Control wild type and two transgenic T2 (second generation) wheat lines derived from MSH1 suppressed T1 (first generation plants with a RNAi construct suppressing wheat MSH1) plants displaying a smaller plant size and smaller head size indicative of the MSH1-dr phenotype.

Example 1. Msh1-Deprived Plastids are Necessary for the Growth Vigor Changes Seen after Crossing Since altered plant development in *Arabidopsis* msh1 is conditioned by plastid changes[1], we tested whether the enhanced growth vigor in $F_2$ lines also emanated from these plastid effects. *Arabidopsis* MSH1 hemi-complementation lines, derived by introducing a mitochondrial-versus chloroplast-targeted MSH1 transgene to the msh1 mutant[11], distinguish mitochondrial and plastid contributions to the phenomenon. Plastid hemi-complementation lines crossed as female to Col-0 resulted in a normal phenotype for some $F_1$ progeny, but with 10% to 77% showing slow germination, leaf curling and delayed flowering (FIG. 1a). The altered phenotypes may be due to mitochondrial changes. In $F_1$ progeny from crosses to the mitochondrial-complemented line, over 30% showed enhanced growth, larger rosette diameter, and earlier flowering time, closely resembling $F_4$ phenotypes from chm1-1×Col-0 (FIGS. 1b and 2a). These results were further confirmed in derived $F_2$ populations (FIG. 1b, 2b-e), indicating that msh1-deprived plastids are necessary for the growth vigor changes seen after crossing.

Methods for Example 1

Plant Materials and Growth Conditions.

*Arabidopsis* Col-0 and msh1 mutant lines were obtained from the *Arabidopsis* stock center and grown at 12 hr day length at 22° C. The segregating T-DNA insertion line, SAIL_877_F01, was genotyped using forward (SEQ ID NO: 14; ACGGAAAAAGTTCTTTCCAGG) and reverse (SEQ ID NO: 15; GCTTTCCATCGGCTAGGTTAG) primers for MSH1 (At3G24320) together with SAIL primer LB3 (SEQ ID NO: 16; TAGCATCTGAATTTCATAACCAATCTCGA-TACAC). Seed from individual plants segregating for the T-DNA insertion in MSH1 was collected from heterozygous and null msh1 mutant plants. Progeny from a single heterozygous parent were grown to produce wild type segregants, heterozygote segregants and first generation msh1 mutant segregants. Second generation msh1 mutants were derived from individual first generation msh1 mutant plants. The advanced generation chmin-1 mutant was described previously[24]. *Arabidopsis* plant measurements and leaf material used for DNA methylome analysis were conducted on 4-5 week-old plants prior to bolting. *Arabidopsis* flowering time was measured as date of first visible flower bud appearance. For hemi-complementation crosses, mitochondrial (AOX-MSH1) and plastid (SSU-MSH1) complemented homozygous lines were crossed to Col-0 wild type plants. Each $F_1$ plant was genotyped for transgene and wild type MSH1 allele and harvested separately. Three F2 families from AOX-MSH1×Col-0 and two F2 families from SSU-MSH1×Col-0 were evaluated for growth parameters. All families were grown under the same conditions, and biomass, rosette diameter and flowering time were measured. Two-tailed Student t-test was used to calculate p-values.

REFERENCES FOR EXAMPLE 1 a. Xu, Y.-Z. et al. The chloroplast triggers developmental reprogramming when MUTS HOMOLOG1 is suppressed in plants. Plant Physiol. 159, 710-720 (2012).

b. Bonasio, R., Tu, S. & Reinberg, D. Molecular signals of epigenetic states. Science 33, 612-616 (2010).
c. Mirouze, M. & Paszkowski, J. Epigenetic contribution to stress adaptation in plants. Curr Opin Plant Biol. 14, 267-274 (2011).
d. Dowen, R. H. et al. Widespread dynamic DNA methylation in response to biotic stress. Proc. Natl. Acad. Sci. USA 109, E2183-2191 (2012).
e. Youngson, N. A. & Whitelaw, E. Transgenerational epigenetic effects. Annu. Rev. Genom. Human Genet 9, 233-257 (2008).
f. Paszkowski, J. & Grossniklaus, U. Selected aspects of transgenerational epigenetic inheritance and resetting in plants. Curr. Opin. Plant Biol. 14, 195-203 (2011).
g. Reinders, J. et al. Compromised stability of DNA methylation and transposon immobilization in mosaic *Arabidopsis* epigenomes. Genes Dev. 23, 939-950 (2009).
h. Cortijo, S et al. Mapping the epigenetic basis of complex traits. Science. 5, epub ahead of print (2014).
i. Roux, F. et al. Genome-wide epigenetic perturbation jump-starts patterns of heritable variation found in nature. Genetics 188, 1015-1017 (2011).
j. Abdelnoor, R. V. et al. Substoichiometric shifting in the plant mitochondrial genome is influenced by a gene homologous to MutS. Proc. Natl. Acad. Sci. USA 100, 5968-5973 (2003).
k. Xu, Y.-Z. et al. MutS HOMOLOG1 is a nucleoid protein that alters mitochondrial and plastid properties and plant response to high light. Plant Cell 23, 3428-3441 (2011).
l. Santa Maria, R., et al. MSH1-induced non-genetic variation provides a source of phenotypic diversity in *Sorghum bicolor*. Submitted.
m. Stroud, H., et al. Comprehensive analysis of silencing mutants reveals complex regulation of the *Arabidopsis* methylome. Cell 152, 352-364 (2013).
n. Becker, C. et al. Spontaneous epigenetic variation in the *Arabidopsis thaliana* methylome. Nature 480, 245-249 (2011).
o. Schmitz, R. J. et al. Transgenerational epigenetic instability is a source of novel methylation variants. Science 334, 369-373 (2011).
p. Shedge, V., Arrieta-Montiel, M. P., Christensen, A. C. & Mackenzie, S. A. Plant mitochondrial recombination surveillance requires unusual RecA and MutS homologs. Plant Cell 19, 1251-1264 (2007).
q. Shedge, V., Davila, J., Arrieta-Montiel, M. P., Mohammed, S. & Mackenzie S. A. Extensive rearrangement of the *Arabidopsis* mitochondrial genome elicits cellular conditions for thermotolerance. Plant Physiol. 152, 1960-1970 (2010).
r. Kalisz, S. & Kramer, E. M. Variation and constraint in plant evolution and development. Hered. 100, 171-177 (2008).
s. Greaves, I., Groszmann, M., Dennis, E. S. & Peacock, W. J. Trans-chromosomal methylation. Epigenetics 7, 800-805 (2012).
t. Shivaprasad, P. V., Dunn, R. M., Santos, B. A., Bassett, A. & Baulcombe, D. C. Extraordinary transgressive phenotypes of hybrid tomato are influenced by epigenetics and small silencing RNAs. EMBO J 31, 257-266 (2012).
u. Wheeler, B. S. Small RNAs, big impact: small RNA pathways in transposon control and their effect on the host stress response. Chromosome Res. 21, 587-600 (2013).
v. Ito, H. Small RNAs and regulation of transposons in plants. Genes Genet Syst. 88, 3-7 (2013).
w. Zhang, C. C, Yuan, W-Y, Zhang, Q-F. RPL1: A gene involved in epigenetic processes regulates phenotypic plasticity in rice. Mol. Plant 5, 482-493 (2012).
x. Redei, G. P. Extra-chromosomal mutability determined by a nuclear gene locus in *Arabidopsis*. Mutat. Res. 18, 149-162 (1973).
y. Langmead, B. & Salzberg, S. Fast gapped-read alignment with Bowtie 2. Nat. Methods 9, 357-359 (2012).
z. Martin M. Cutadapt removes adapter sequences from high-throughput sequencing reads. EMBnet Journal. 17, 1 (2011).

Patel R. K., Jain M. NGS QC Toolkit: A toolkit for quality control of next generation sequencing data PLoS ONE 7(2): e30619 (2012)

28. Hannon Lab. FASTX-Toolkit. http internet site hannonlab.cshl.edu/fastx_toolkit/
29. Zerbino D. R., McEwen G. K., Margulies E. H., Birney E. Pebble and Rock Band: Heuristic Resolution of Repeats and Scaffolding in the Velvet Short-Read de Novo Assembler. PLoS ONE 4(12): e8407 (2009).
30. Camacho, C. et al. BLAST+: architecture and applications. BMC Bioinformatics 10, 421 (2009).
31. Li, H. et al. The Sequence alignment/map (SAM) format and SAMtools. Bioinformatics 25, 2078-2079 (2009).
32. Lu, P. et al. Analysis of *Arabidopsis* genome-wide variations before and after meiosis and meiotic recombination by resequencing *Landsberg erecta* and all four products of a single meiosis. Genome Res. 22, 508-518 (2012).
33. Krueger, F. & Andrews, S. R. Bismark: a flexible aligner and methylation caller for Bisulfite-Seq applications. Bioinformatics 27, 1571-1572 (2011).
34. Storey, J. D. & Tibshirani, R. Statistical significance for genome-wide studies. Proc. Natl. Acad. Sci. USA 100, 9440-9445 (2003).
35. Hebestreit, K., Dugas, M. & Klein, H.-U. Detection of significantly differentially methylated regions in targeted bisulfite sequencing data. Bioinformatics 29, 1647-53 (2013).
36. Jombart, T. & Ahmed, I. adegenet 1.3-1: new tools for the analysis of genome-wide SNP data. Bioinformatics 27, 3070-1 (2011).
37. Jombart, T. adegenet: a R package for the multivariate analysis of genetic markers. Bioinformatics 24, 1403-5 (2008).
38. Maechler, M., Rousseeuw, P., Anja Struyf, M. H. & Hornik, K. cluster: Cluster Analysis Basics and Extensions. R package version 1.15.1. (2013).
39. Joe H. Ward, J. Hierarchical Grouping to Optimize an Objective Function. J. Am. Stat. Assoc. 58, 236-244 (1963).
40. Akalin, A. et al. methylKit: a comprehensive R package for the analysis of genome-wide DNA methylation profiles. Genome Biol. 13, R87 (2012).
41. Nisar, N., Verma, S., Pogson, B. J. & Cazzonelli, C. I. Inflorescence stem grafting made easy in *Arabidopsis*. Plant Methods 8(1):50. (2012).
42. Boyko, A. et al. Transgenerational adaptation of *Arabidopsis* to stress requires DNA methylation and the function of Dicer-like proteins. PLoS ONE. 5(3):e95149. (2010).

Example 2. The FYA Mutation of MSH1 DNA Binding Domain 1 Creates a Plastid Deficient but Mitochondrially Functional MSH1

The MSH1 DNA binding domain is highly conserved, particularly in the FYE amino acid motif located in Domain 1 (SEQ ID NO: 17; VLLCRVGEFYEAIGIDA; Abdelnoor et al., Proc Natl Acad Sci USA. 2003 May 13; 100(10): 5968-73). This FYE amino acid sequence is present in most if not all plant species (Table 1). To construct a MSH1 gene containing a FYE to FYA mutation, a full length 7.1 kb genomic gene of MSH1 with its native promoter and lacking its stop codon (Xu et al., Plant Cell. 2011 September; 23(9):3428-41) was first cloned into pBluescript SK (+) vector. A PCR based QuikChange Site-Directed Mutagenesis Kit was used to create a specific codon mutation (to change FYE to FYA), and the expected mutation was confirmed with DNA sequencing in the resulting isolated plasmid DNA. The mutated MSh1 genomic clone (FYA) DNA fragment was released with restriction enzymes from pBluescript SK and recloned into binary vector pCambia 1302, resulting in an inframe fusion of MSH1 with mGFP. For genetic complementation assays, MSH1 heterozygous (MSH1/msh1) plants were dipped with *Agrobacterium* containing the genomic MSH1-GFP binary plasmid construct and T1 transformed plants were selected on hygromycin (30 ug/ml) plates. Plants carrying homozygous MSH1 mutations (msh1/msh1) and the MSH1-GFP transgene were identified for further analysis. Mutation of FYE to FYA was observed to disrupt plastid MSH1 function in *Arabidopsis* seedlings as a FYA MSH1 transgene expressed in a msh1/msh1 genotype displayed leaf varigation (FIG. 3 top panel). This indicates MSH1 was not functioning in the plastids. Additionally, when older, these plants also displayed a MSH1-dr phenotype (FIG. 3 middle panel). Typically, mitochondria lacking MSH1 function display abnormal mitochondrial recombination (FIG. 3 bottom panels: compare single band in wild type Col-0 to the two bands in the msh1/msh1 genotype and the Empty vector (also msh1/msh1) samples when analyzed by PCR for mitochrondrial recombination). Importantly, plants with the FYA MSH1 transgene in msh1/msh1 did not show mitochondrial recombination, indicating the FYA form of MSH1 was functional in the mitochondria (FIG. 3 bottom panel "FYE/FYA" showing only a single PCR band size, indicative of a normal mitochondrial genome that did not recombine abnormally). The FYE to FYA change in MSH1 Domain 1 provides a method for suppression of MSH1 plastid function while maintaining MSH1 mitochondrial function (hemi-complementation) similar to the mitochondrial-targeted MSH1 hemi-complementation described in Example 1. As such, the FYA form of MSH1 causes suppression of MSH1 plastid function while maintaining MSH1 mitochondrial function and will produce plants with useful traits and/or epigenetic changes useful for plant breeding as described for the hemi-complementation methods in Example 1 when said plants are outcrossed to recover MSH1 function. Mutation of an endogenous MSH1 gene from FYE to FYA by random mutagenesis and screening or targeted genome editing methods such as homologous recombination or CAS9 systems provides a method for suppression of MSH1 plastid function while maintaining MSH1 mitochondrial function to produce plants with useful traits and/or epigenetic changes useful for plant breeding that does not require adding mitochondrial targeting sequences to MSH1.

The following MSH1 proteins in the following species have been found to contain a FYE domain in the DNA binding domain (Table 1) and are suitable for mutating the FYE domain in accordance with an embodiment of the present disclosure.

TABLE 1

MSH1 protein sequences from plant species containing a FYE sequence in the conserved DNA binding domain of MSH1.

| Species | NCBI Genbank Protein Accession Number |
|---|---|
| *Capsella rubella* | XP_006299281.1 |
| *Ricinus communis* | XP_002528340.1 |
| *Populus trichocarpa* | XP_002314510.1 |
| *Theobroma cacao* | XP_007035297.1 |
| *Citrus sinensis* | XP_006480235.1 |
| *Citrus clementine* | XP_006420379.1 |
| *Vitis vinifera* | XP_002282256.1 |
| *Prunus persica* | XP_007225427.1 |
| *Fragaria vesca* subsp. *Vesca* | XP_004297941.1 |
| *Solanum tuberosum* | XP_006340883.1 |
| *Cucumis sativus* | XP_004134396.1 |
| *Solanum lycopersicum* | XP_004247788.1 |
| *Cicer arietinum* | XP_004497789.1 |
| *Glycine max* | NP_001238217.1 |
| *Phaseolus vulgaris* | AAX31514.1 |
| *Oryza sativa* Japonica Group | NP_001053261.1 |
| *Oryza sativa* Indica Group | CAH67334.1 |
| *Oryza brachyantha* | XP_006652491.1 |
| *Setaria italic* | XP_004976164.1 |
| *Medicago truncatula* | XP_003590183.1 |
| *Zea mays* | AFW58800.1 |
| *Cucumis sativus* | ACA35268.1 |
| *Hordeum vulgare* subsp. *Vulgare* | BAK01143.1 |
| *Sorghum bicolor* | XP_002448138.1 |
| *Aegilops tauschii* | EMT01808.1 |
| *Triticum_aestivum* | SEQ ID NO: 1 |

Example 3. Transgenic Containing a Wheat MSH1 RNAi Hairpin Construct for Suppressing MSH1

A wheat MSH1 cDNA sequence (SEQ ID NO: 2) provided sequences of PCR primers to PCR a cDNA from wheat (*Triticum aestivum* var CB037) across a region corresponding to Domain VI of wheat MSH1 (SEQ ID NO: 3), which was cloned in the forward and reverse directions into pUCRNAi-intron vector, which harbors the second intron of the *Arabidopsis* small nuclear riboprotein (At4g02840), provided by H. Cerutti (University of Nebraska, Lincoln, Nebr.). This intron and flanking sequence serves as a spacer region between the inverted regions of the Domain VI of wheat MSH1 (SEQ ID NO: 3). The/Wheat MSH1 reverse/intron/Wheat MSH1 forward/DNA fragment was subcloned into pRTL2 such that a CaMV 35S terminator (polyadenylation region) was downstream. The 5' maize ubiquitin promoter/intron (U.S. Pat. No. 5,510,474) was excised from pLZ-P3 and inserted upstream of the MSH1/intron/MSH1 hairpin region. The resulting RNAi construct (FIG. 5.1) has the following order of DNA fragments: HindIII/5'-Maize Ubiquitin promoter/intron/Wheat MSH1 Domain VI (SEQ ID NO: 3 reverse orientation)/At4g02840 intron 2/Wheat MSH1 Domain VI (SEQ ID NO: 3 forward orientation)/CaMV35S terminator/HindIII. This DNA fragment was excised as a HindIII cassette and inserted into the HindIII site of pPZP212, which is an *Agrobacterium* binary vector containing a plant kanamycin resistance selectable marker (Hajdukiewicz et al., Plant Mol. Biol. 25:989-99, 1994). Transgenic wheat containing said Wheat MSH1 RNAi (FIG. 5.1) construct were produced as described using a G418 selection (Fu et al., Plant Mol Biol (2008) 68:277-288) and have a MSH1 dr-phenotype (FIG. 4). These wheat MSH1-dr phenotype lines are useful for altering the epigenome of wheat to produce plants with increased yields and that are useful for plant breeding when self pollinated and/or outcrossed, and each subsequent non-transgenic generation is self pollinated to produce wheat plants with enhanced yields, relative to their parental control plants.

Example 4. Transgenic Rice with Suppression of Plastidic MSH1 in the Presence of Mitochondrial-Targeted MSH1 Using the *Arabidopsis* AOX1 Mitochondrial Targeting Signal The binary vector for suppression of plastidic MSH1 in the presence of mitochondrial-targeted MSH1 T-DNA region is CAMBIA1300-BAR, a CAMBIA1300 derived vector that is modified to replace the hygromycin selectable marker with a *Streptomyces hygroscopicus* bar gene for selection of transformed plant cells with bialophos or phosphinothricin. The BAR gene is commercially synthesized with flanking XhoI sites (SEQ ID NO: 6) and ligated into pCAMBIA1300 restricted with XhoI to remove the hygromycin gene. The resulting pCAMBIA1300-BAR (FIG. 5.2) binary plasmid has the BAR selectable gene as a CaMV35S promoter/BAR/CaMV 35S terminator (polyadenylation site) cassette for use as a selectable marker in plants. A mitochondrial targeted MSH1 gene is constructed as follows. A 2,047 bp rice MSH1 promoter is isolated from rice genome DNA (*Oryza sativa* ssp *japonica* cv. Nipponbare) by PCR with Phusion DNA polymerase with PCR primers to obtain the DNA fragment with the sequence in SEQ ID NO: 4. The PCR primers introduce a 5' BglII and a 3' XhoI sites flanking the rice MSH1 promoter (SEQ ID NO: 4). A synthetic coding region for targeting MSH1 to mitochondria in rice encodes an *Arabidopsis* Alternative Oxidase 1 (AOX1) mitochondrial targeting sequence (Xu et al., Plant Physiol. 2012 June; 159(2):710-20) attached to a rice MSH1 protein lacking a organellar dual targeting sequence. This coding region is attached to a Nopaline Synthase 3' polyadenylation region, and the entire sequence is commercially synthesized (SEQ ID NO: 5). The coding region of this *Arabidopsis* AOX1-Rice MSH1/NOS3' DNA fragment (SEQ ID NO: 5) has altered codon choices to change the *Arabidopsis* AOX1 codons to be more representative of monocot codons and for the region encoding rice MSH1 to have low homology to the native endogenous rice MSH1 gene sequences. This low homology allows for RNAi silencing of the endogenous gene by a MSH1 RNAi gene without silencing the mitochondrial targeted *Arabidopsis* AOX1-Rice MSH1/NOS3' gene (SEQ ID NO: 5). A BLAST analysis of the homology between the native rice MSH1 coding region (such as the sequence of rice NM_001059796.1 at NCBI) and the synthetic rice MSH1 sequence (SEQ ID NO: 5) found only 74% sequence identity, with 15 or less sequential identical bases in any region, between the two genes. The synthetic *Arabidopsis* AOX1-Rice MSH1/NOS3' DNA fragment has a 5' SalI site and 3' SbfI site (SEQ ID NO: 5). A 5' BglII and 3' XhoI restricted rice MSH1 promoter, a 5' SalI and 3' SbfI restricted *Arabidopsis* AOX1-Rice MSH1/NOS3' DNA fragment, and a BamHI and SbfI restricted pCAMBIA1300-BAR plasmid vector are gel purified, recovered on Qiagen DNA columns, ligated as a 3 piece DNA ligation, transformed into *E. coli*, and a CAMBIA1300-BAR vector containing a rice MSH1 promoter (SEQ ID NO: 4)/*Arabidopsis* AOX1-Rice MSH1/NOS3 (SEQ ID NO: 5) is obtained (herein named pCAMBIA1300-BAR//Arab-AOX1-Rice-MSH1; FIG. 5.3). A 5' SbfI/maize Ubiquitin promoter/intron/3' BamHI (U.S. Pat. No. 5,510,474) DNA fragment is present in pPRH1-RNAi. A region of Domain VI of the native rice MSH1 gene is used for a hairpin RNAi construct, in both the forward (SEQ ID NO: 7) and reverse orientations. Commercially synthesized DNA is used to generate 2 DNA fragments of the following design: BamHI/reverse rice MSH1 domain VI (SEQ ID NO: 7)/caster bean catalase intron/EcoRI+EcoRI/forward rice MSH1 domain VI (SEQ ID NO: 7)/Octapine Synthase 3' polyadenylation region/HindIII. These are ligated into pUC19 in a 3 piece ligation to form an insert of the following order of DNA regions: BamHI/reverse rice MSH1 domain VI (SEQ ID NO: 7)/catalase intron/EcoRI/forward rice MSH1 domain VI (SEQ ID NO: 7)/Octapine Synthase 3' polyadenylation region/HindIII. A 5' SbfI/maize Ubiquitin promoter/intron/3' BamHI DNA fragment, a BamHI/reverse rice MSH1 domain VI (SEQ ID NO: 7)/catalase intron/EcoRI/forward rice MSH1 domain VI (SEQ ID NO: 7)/Octapine Synthase 3' polyadenylation region/HindIII DNA fragment, and a pCAMBIA1300-BAR//Arab-AOX1-Rice-MSH1 binary vector digested with SbfI and HindIII DNA fragment are gel purified, recovered on Qiagen DNA columns, ligated as a 3 piece DNA ligation, transformed into *E. coli*, and a pCAMBIA1300-BAR//Arab-AOX1-Rice-MSH1 vector containing a Rice MSH1 RNAi gene (5' SbfI/maize Ubiquitin promoter/intron/reverse rice MSH1 domain VI (SEQ ID NO: 7)/catalase intron/EcoRI/forward rice MSH1 domain VI (SEQ ID NO: 7)/Octapine Synthase 3' polyadenytion region/HindIII and is named Rice MSH1 RNAi herein; FIG. 5.4) is obtained (herein named pCAMBIA1300-BAR//Arab-AOX1-Rice-MSH1//Rice MSH1 RNAi; FIG. 5.5). Rice embryogenic callus (*Oryza sativa* ssp *japonica* cv. Nipponbare) is transformed by *Agrobacterium*-mediated transformation methods as described in Shrawat and Lorz (Plant Biotechnology Journal (2006) 4, pp. 575-603) and references therein, using the bar gene of pCAMBIA1300-BAR//Arab-AOX1-Rice-MSH1//Rice MSH1 RNAi as a selectable marker and bialophos as the selective agent, and regenerated transgenic rice plants are obtained. Said transgenic rice plants are screened for those that suppress endogenous rice MSH1 by real time PCR analysis of cDNA made from isolated RNA from the plants. Transgenic rice plants suppressed for MSH1 will be self pollinated and outcrossed to each parental line to obtain non-transgenic progeny, and each subsequent non-transgenic generation is self pollinated to produce rice plants with enhanced yields, relative to their parental control plants.

Example 5. Transgenic Rice with Suppression of Plastidic MSH1 in the Presence of Mitochondrial-Targeted MSH1 Using the Rice AOX1 Mitochondrial Targeting Signal Substitution of a rice mitochondrial targeting signal into the mitochondrial targeted MSH1 construct of Example 4 is accomplished by replacement of SEQ ID NO: 5 with SEQ ID NO: 8. SEQ ID NO: 8 has the following sequence elements: 5' SalI site/rice AOX mitochondrial targeting signal/synthetic rice MSH1 (lacking its dual targeting sequence and with limited homology to endogenous rice MSH1 due to codon changes as in Example 4)/NOS3'/SbfI 3' site. Because the flanking restriction sites are the same, the methods of Example 4 are followed with just this substitution. The first resulting binary plasmid containing a rice AOX1-rice MSH1 gene is named pCAMBIA1300-BAR//Rice-AOX1-Rice-MSH1 (FIG. 5.6). A 5' SbfI and 3' HindIII Rice MSH1 RNAi DNA fragment from the binary vector pCAMBIA1300-BAR//Arab-AOX1-Rice-MSH1//Rice MSH1 RNAi in Example 4 is inserted into the SbfI and HindIII sites of pCAMBIA1300-BAR//Rice-AOX1-Rice-MSH1 to obtain pCAMBIA1300-BAR//Rice-AOX1-Rice-MSH1//Rice MSH1 RNAi (FIG. 5.7). Rice embryogenic callus (*Oryza sativa* ssp *japonica* cv. Nipponbare) is transformed by *Agrobacterium*-mediated transformation methods as described in Shrawat and Lorz (Plant Biotechnology Journal (2006) 4, pp. 575-603) and references therein, using the bar gene of pCAMBIA1300-BAR//Rice-AOX1-Rice-MSH1//Rice MSH1 RNAi as a selectable marker and phosphinothricin as the selective agent, and regenerated transgenic rice plants are obtained. Said transgenic rice plants are screened for those that suppress endogenous rice MSH1 by real time PCR analysis of cDNA made from isolated RNA from the plants. Transgenic rice plants suppressed for MSH1 are self pollinated and outcrossed to each parental line to obtain non-transgenic progeny, and each subsequent non-transgenic generation is self pollinated to produce rice plants with enhanced yields, relative to their parental control plants.

Example 6. Transgenic Wheat with Suppression of Plastidic MSH1 in the Presence of Mitochondrial-Targeted MSH1 Using the *Arabidopsis* AOX1 Mitochondrial Targeting Signal Construct pCAMBIA1300-BAR//Arab-AOX1-Rice-MSH1 of Example 4 expresses a fusion of the *Arabidopsis* AOX1 mitochondrial targeting signal fused to the rice synthetic MSH1 coding region, wherein the sequences encoding the MSH1 dual targeting signals have been removed and replaced by the *Arabidopsis* AOX1 sequences. The expression of this construct will target and provide MSH1 function in the mitochondria of transgenic wheat containing this construct. Endogenous wheat MSH1 is suppressed by the expression of a hairpin RNAi construct with homology against the endogenous wheat MSH1 genes and is constructed as follows. A 5' SbfI/maize Ubiquitin promoter/intron/3' BamHI (U.S. Pat. No. 5,510,474) DNA fragment is present in pPRH1-RNAi plasmid DNA. A region of Domain VI of the native wheat MSH1 gene is used for a hairpin RNAi construct, in both the forward (SEQ ID NO: 3) and reverse orientations. Commercially synthesized DNA is used to generate 2 DNA fragments of the following design: BamHI/reverse wheat MSH1 domain VI (SEQ ID NO: 3)/caster bean catalase intron/EcoRI+EcoRI/forward wheat MSH1 domain VI (SEQ ID NO: 3)/Octapine Synthase 3' polyadenyation region/HindIII. These are ligated into pUC19 in a 3 piece ligation to form an insert of the following order of DNA regions: BamHI/reverse wheat MSH1 domain VI (SEQ ID NO: 3)/catalase intron/EcoRI/forward wheat MSH1 domain VI (SEQ ID NO: 3)/Octapine Synthase 3' polyadenyation region/HindIII. A 5' SbfI/maize Ubiquitin promoter/intron/3' BamHI DNA fragment, a BamHI/reverse wheat MSH1 domain VI (SEQ ID NO: 3)/catalase intron/EcoRI/forward wheat MSH1 domain VI (SEQ ID NO: 3)/Octapine Synthase 3' polyadenyation region/HindIII DNA fragment, and a pCAMBIA1300-BAR//Arab-AOX1-Rice-MSH1 binary vector digested with SbfI and HindIII DNA fragment are gel purified, recovered on Qiagen DNA columns, ligated as a 3 piece DNA ligation, transformed into *E. coli*, and a pCAMBIA1300-BAR//Arab-AOX1-Rice-MSH1 vector containing a Wheat MSH1 RNAi gene (FIG. 5.8: maize Ubiquitin promoter/intron/reverse wheat MSH1 domain VI (SEQ ID NO: 3)/catalase intron/EcoRI/forward wheat MSH1 domain VI (SEQ ID NO: 3)/Octapine Synthase 3' polyadenyation region, named Wheat MSH1 RNAi herein) is obtained (herein named pCAMBIA1300-BAR//Arab-AOX1-Rice-MSH1//Wheat MSH1 RNAi; FIG. 5.9). For producing transgenic wheat plants of Bobwhite, 251BW012 and Autry525 genotypes, a wheat genotype-independent transformation method is used as described in U.S. Pat. No. 8,212,109, using the bar gene of pCAMBIA1300-BAR//Arab-AOX1-Rice-MSH1//Wheat MSH1 RNAi as a selectable marker and bialaphos as the selective agent as described in U.S. Pat. No. 7,705,215, and regenerated transgenic wheat plants are obtained. Said transgenic wheat plants are screened for those that suppress endogenous wheat MSH1 by real time PCR analysis of cDNA made from isolated RNA from the plants. Transgenic wheat plants suppressed for MSH1 will be self pollinated and outcrossed to each parental line to obtain non-transgenic progeny, and each subsequent non-transgenic generation is self pollinated to produce wheat plants with enhanced yields, relative to their parental control plants.

Example 7. Transgenic Wheat with Suppression of Plastidic MSH1 in the Presence of Mitochondrial-Targeted MSH1 Using the Rice AOX1 Mitochondrial Targeting Signal Construct pCAMBIA1300-BAR//Rice-AOX1-Rice-MSH1 of Example 5 expresses a fusion of a Rice AOX1 mitochondrial targeting signal fused to the rice synthetic MSH1 coding region, wherein the sequences encoding the MSH1 dual targeting signals have been removed and replaced by the Rice AOX1 sequences. The expression of this construct targets and provides MSH1 function in the mitochondria of transgenic wheat containing this construct.

Endogenous wheat MSH1 is suppressed by the expression of a hairpin RNAi construct with homology against the endogenous wheat MSH1 genes contained in the Wheat MSH1 RNAi gene cassette of Example 6. A SbfI and HindIII digested pCAMBIA1300-BAR//Rice-AOX1-Rice-MSH1 and a similarly digest Wheat MSH1 RNAi gene cassette isolated from pCAMBIA1300-BAR//Arab-AOX1-Rice-MSH1//Wheat MSH1 RNAi are gel purified, recovered on Qiagen DNA columns, ligated as a 2 piece DNA ligation, transformed into *E. coli*, and a CAMBIA1300-BAR//Rice-AOX1-Rice-MSH1 vector containing Wheat MSH1 RNAi is obtained (FIG. 5.10: herein named pCAMBIA1300-BAR//Rice-AOX1-Rice-MSH1//Wheat MSH1 RNAi). For producing transgenic wheat plants of Bobwhite, 251BW012 and Autry525 genotypes, a wheat genotype-independent transformation method is used as described in U.S. Pat. No. 8,212,109, and references therein, using the bar gene of pCAMBIA1300-BAR//Rice-AOX1-Rice-MSH1//Wheat MSH1 RNAi as a selectable marker and bialaphos as the selective agent as described in U.S. Pat. No. 7,705,215, and regenerated transgenic wheat plants are obtained. Said transgenic wheat plants are screened for those that suppress endogenous wheat MSH1 by real time PCR analysis of cDNA made from isolated RNA from the plants. Transgenic wheat plants suppressed for MSH1 will be self pollinated and outcrossed to each parental line to obtain non-transgenic progeny, and each subsequent non-transgenic generation is self pollinated to produce wheat plants with enhanced yields, relative to their parental control plants.

Example 8. Transgenic Maize with Suppression of Plastidic MSH1 in the Presence of Mitochondrial-Targeted MSH1 Using the *Arabidopsis* AOX1 Mitochondrial Targeting Signal The methods of Example 6, with substitution of a 315 bp region of maize (*Zea mays*) MSH1 Domain VI (SEQ ID NO:

9) for the wheat Domain VI region, to produce a Maize MSH1 RNA hairpin RNAi gene for suppressing maize MSH1 (FIG. 6.11). Said Maize MSH1 RNA gene cassette is moved into pCAMBIA1300-BAR//Arab-AOX1-Rice-MSH1 as a SbfI and HindIII restricted fragment, following the methods of Example 6. The resulting pCAMBIA1300-BAR//Arab-AOX1-Rice-MSH1//Maize MSH1 RNAi (FIG. 6.12) binary vector expresses a mitochondrial targeted Arab-AOX1-Rice-MSH1 while suppressing the endogenous maize MSH1 via the RNAi hairpin cassette. Transgenic maize cells are produced using the bar gene of pCAMBIA1300-BAR//Arab-AOX1-Rice-MSH1//Maize MSH1 RNAi as a selectable marker and bialaphos as the selective agent as described in U.S. Pat. Nos. 5,489,520 and 5,550,318 and regenerated transgenic maize plants are obtained. Said transgenic maize plants are screened for those that suppress endogenous maize MSH1 by real time PCR analysis of cDNA made from isolated RNA from the plants. Transgenic maize plants suppressed for MSH1 will be self pollinated and outcrossed to each parental line to obtain non-transgenic progeny, and each subsequent non-transgenic generation is self pollinated to produce maize plants with enhanced yields, relative to their parental control plants.

Example 9. Transgenic Maize with Suppression of Plastidic MSH1 in the Presence of Mitochondrial-Targeted MSH1 Using the Rice AOX1 Mitochondrial Targeting Signal The methods of Examples 6 and 7, with substitution of a 315 bp region of maize (*Zea mays*) MSH1 Domain VI (SEQ ID NO: 9) for the wheat Domain VI region, are followed to produce a Maize MSH1 RNA hairpin RNAi gene for suppressing maize MSH1 (FIG. 6.11). Said Maize MSH1 RNA gene cassette is moved into pCAMBIA1300-BAR//Rice-AOX1-Rice-MSH1 as a SbfI and HindIII restricted fragment, following the methods of Example 7. The resulting pCAMBIA1300-BAR//Rice-AOX1-Rice-MSH1//Maize MSH1 RNAi (FIG. 6.13) binary vector expresses a mitochondrial targeted Rice MSH1 while suppressing the endogenous maize MSH1 via the RNAi hairpin cassette (Maize MSH1 RNAi).

Transgenic maize cells are produced using the bar gene of pCAMBIA1300-BAR//Rice-AOX1-Rice-MSH1//Maize MSH1 RNAi as a selectable marker and bialaphos as the selective agent as described in U.S. Pat. Nos. 5,489,520 and 5,550,318 and regenerated transgenic maize plants are obtained. Said transgenic maize plants are screened for those that suppress endogenous maize MSH1 by real time PCR analysis of cDNA made from isolated RNA from the plants. Transgenic maize plants suppressed for MSH1 will be self pollinated and outcrossed to each parental line to obtain non-transgenic progeny, and each subsequent non-transgenic generation is self pollinated to produce maize plants with enhanced yields, relative to their parental control plants.

Example 10. Transgenic Soybeans with Suppression of Plastidic MSH1 in the Presence of Mitochondrial-Targeted MSH1 Using the *Arabidopsis* AOX1 Mitochondrial Targeting Signal A synthetic coding region for targeting soybean MSH1 to mitochondria in soybeans encodes an *Arabidopsis* Alternative Oxidase 1 (AOX1) mitochondrial targeting sequence (Xu et al., Plant Physiol. 2012 June; 159(2):710-20) attached to a synthetic soybean MSH1 protein lacking a organellar dual targeting sequence. This coding region is attached to a Nopaline Synthase 3' polyadenylation region, and the entire sequence is commercially synthesized (SEQ ID NO: 10). The soybean MSH1 coding region of this DNA fragment (SEQ ID NO: 10) has altered codon choices to have low homology to the native endogenous soybean MSH1 gene sequences. This low homology allows for RNAi silencing of the endogenous gene by a MSH1 RNAi gene without silencing the mitochondrial targeted *Arabidopsis* AOX1-Soy MSH1/NOS3' gene. A BLAST analysis of the homology between two native soybean MSH1 coding regions (such as the sequence of NM_001251288 or XM_003555649.2 at NCBI) and the synthetic soybean MSH1 sequence (SEQ ID NO: 10) found only 74% or 71% sequence identity, respectively, with less than 15 sequential identical bases in any region, between SEQ ID NO: 10 and either of the two soybean MSH1 genes. This synthetic *Arabidopsis* AOX1-Soy-MSH1/NOS3' DNA fragment has a 5' SalI site and 3' SbfI site (SEQ ID NO: 10). A 5' BamHI and 3' SalI restricted 758 bp *Arabidopsis* MSH1 promoter (Xu et al., The Plant Cell, Vol. 23: 3428-3441, September 2011), a 5' SalI and 3' SbfI restricted *Arabidopsis* AOX1-Soy-MSH1/NOS3' DNA fragment, and a BamHI and SbfI restricted pCAMBIA1300-BAR plasmid vector are gel purified, recovered on Qiagen DNA columns, ligated as a 3 piece DNA ligation, transformed into *E. coli*, and a CAMBIA1300-BAR vector containing an *Arabidopsis* MSH1 promoter attached to an *Arabidopsis* AOX1-Soy MSH1/NOS3 (SEQ ID NO: 10) is obtained (herein named pCAMBIA1300-BAR//Arab PRO-Arab-AOX1-Soy-MSH1; FIG. 6.14).

To construct a Soybean MSH1 RNAi gene cassette (FIG. 6.15), a region of Domain VI of a native soybean MSH1 gene lacking a HindIII site (SEQ ID NO: 11) is used for a hairpin RNAi construct, in both the forward and reverse orientations. Commercially synthesized DNA is used to generate 2 DNA fragments of the following design: BamHI/reverse Soy MSH1 domain VI (SEQ ID NO: 11)/caster bean catalase intron/EcoRI+EcoRI/forward Soy MSH1 domain VI (SEQ ID NO: 11)/Octapine Synthase 3' polyadenyation region/HindIII. These are ligated into pUC19 in a 3 piece ligation to form an insert of the following order of DNA regions: BamHI/reverse Soy MSH1 domain VI (SEQ ID NO: 11)/catalase intron/EcoRI/forward Soy MSH1 domain VI (SEQ ID NO: 11)/Octapine Synthase 3' polyadenyation region/HindIII. A 5' SbfI/CaMV 35S promoter/3' BamHI DNA fragment, a BamHI/reverse Soy MSH1 domain VI (SEQ ID NO: 11)/catalase intron/EcoRI/forward Soy MSH1 domain VI (SEQ ID NO: 11)/Octapine Synthase 3' polyadenyation region/HindIII DNA fragment, and a pCAMBIA1300-BAR//Arab PRO-Arab-AOX1-Soy-MSH1 binary vector digested with SbfI and HindIII DNA fragment are gel purified, recovered on Qiagen DNA columns, ligated as a 3 piece DNA ligation, transformed into *E. coli*, and a pCAMBIA1300-BAR//Arab PRO-Arab-AOX1-Soy-MSH1 vector containing a Soy MSH1 RNAi gene (5' SbfI/CaMV 35S promoter/reverse Soy MSH1 domain VI (SEQ ID NO: 11)/catalase intron/EcoRI/forward Soy MSH1 domain VI (SEQ ID NO: 11)/Octapine Synthase 3' polyadenyation region/HindIII) is obtained (FIG. 6.16; herein named pCAMBIA1300-BAR//Arab PRO-Arab-AOX1-Soy-MSH1//Soy MSH1 RNAi).

Transgenic soybeans plants are produced with pCAMBIA1300-BAR//Arab PRO-Arab-AOX1-Soy-MSH1//Soy MSH1 RNAi in Agrobacteria and using glufosinate as the selection system as described (Zhang et al., Plant Cell, Tissue and Organ Culture 56: 37-46, 1999). Said transgenic soybean plants are screened for those that suppress endogenous soybean MSH1 (sequences homologous to NM_001251288 or XM_003555649.2 at NCBI) by real time PCR analysis of cDNA made from isolated RNA from the plants. Transgenic soybean plants suppressed for MSH1 are self pollinated and outcrossed to each parental line to obtain non-transgenic progeny, and each subsequent non-transgenic generation is self pollinated to produce soybean plants with enhanced yields, relative to their parental control plants.

Example 11. Transgenic Tomatoes with Suppression of Plastidic MSH1 in the Presence of Mitochondrial-Targeted MSH1 Using the *Arabidopsis* AOX1 Mitochondrial Targeting Signal A synthetic coding region for targeting potato MSH1 to mitochondria in tomato encodes an *Arabidopsis* Alternative Oxidase 1 (AOX1) mitochondrial targeting sequence (Xu et al., Plant Physiol. 2012 June; 159(2):710-20) attached to a potato (which is 98% identical to a tomato MSH1 sequence) MSH1 protein lacking a organellar dual targeting sequence. This coding region is attached to a Nopaline Synthase 3' polyadenylation region, and the entire *Arabidopsis* AOX1-Potato MSH1/NOS3' DNA sequence is commercially synthesized (SEQ ID NO: 12). The potato MSH1 coding region of this DNA fragment (SEQ ID NO: 12) has altered codon choices to have low homology to the native endogenous tomato MSH1 gene sequences. This low homology allows for RNAi silencing of the endogenous tomato MSH1 gene by a MSH1 RNAi gene without silencing the mitochondrial targeted *Arabidopsis* AOX1-Potato MSH1/NOS3' gene. A BLAST analysis of the homology between a native tomato MSH1 coding regions (such as the sequence of AY866434) and the synthetic potato MSH1 sequence (SEQ ID NO: 12) found only 72% sequence identity, respectively, with less than 15 sequential identical bases in any region, between SEQ ID NO: 12 and the tomato native MSH1 gene. This synthetic *Arabidopsis* AOX1-Potato-MSH1/NOS3' DNA fragment has a 5' SalI site and 3' SbfI site (SEQ ID NO: 12). A 5' BamHI and 3' SalI restricted 758 bp *Arabidopsis* MSH1 promoter (Xu et al., The Plant Cell, Vol. 23: 3428-3441, September 2011), a 5' SalI and 3' SbfI restricted *Arabidopsis* AOX1-Potato-MSH1/NOS3' DNA fragment, and a BamHI and SbfI restricted pCAMBIA2300 plasmid vector are gel purified, recovered on Qiagen DNA columns, ligated as a 3 piece DNA ligation, transformed into *E. coli*, and a CAMBIA2300 vector containing an *Arabidopsis* MSH1 promoter attached to an *Arabidopsis* AOX1-Potato MSH1/NOS3 (SEQ ID NO: 12) is obtained (herein named pCAMBIA2300//Arab PRO-Arab-AOX1-Potato-MSH1; FIG. 6.17). To construct a Tomato MSH1 RNAi gene cassette (FIG. 6.18), a region of Domain VI of a native tomato MSH1 gene lacking a HindIII site (SEQ ID NO: 13) is used for a hairpin RNAi construct, in both the forward and reverse orientations. Commercially synthesized DNA is used to generate 2 DNA fragments of the following design: BamHI/reverse Tomato MSH1 domain VI (SEQ ID NO: 13)/caster bean catalase intron/EcoRI+EcoRI/forward Tomato MSH1 domain VI (SEQ ID NO: 13)/Octapine Synthase 3' polyadenyation region/HindIII. These are ligated into pUC19 in a 3 piece ligation to form an insert of the following order of DNA regions: BamHI/reverse Tomato MSH1 domain VI (SEQ ID NO: 13)/catalase intron/EcoRI/forward Tomato MSH1 domain VI (SEQ ID NO: 13)/Octapine Synthase 3' polyadenyation region/HindIII. A 5' SbfI/CaMV 35S promoter/3' BamHI DNA fragment, a BamHI/reverse Tomato MSH1 domain VI (SEQ ID NO: 13)/catalase intron/EcoRI/forward Tomato MSH1 domain VI (SEQ ID NO: 13)/Octapine Synthase 3' polyadenyation region/HindIII DNA fragment, and a pCAMBIA2300//Arab PRO-Arab-AOX1-Potato-MSH1 binary vector digested with SbfI and HindIII DNA fragment are gel purified, recovered on Qiagen DNA columns, ligated as a 3 piece DNA ligation, transformed into *E. coli*, and a pCAMBIA2300//Arab PRO-Arab-AOX1-Potato-MSH1 vector containing a Tomato MSH1 RNAi gene is obtained (herein named pCAMBIA2300//Arab PRO-Arab-AOX1-Potato-MSH1//Tomato MSH1 RNAi; FIG. 6.19). Transgenic tomato plants are produced pCAMBIA2300//Arab PRO-Arab-AOX1-Potato-MSH1//Tomato MSH1 RNAi in Agrobacteria and using kanamycin as the selection system as described (McCormick et al. 1986 Plant Cell Rep 5:81-84). Said transgenic tomato plants are screened for those that suppress endogenous tomato MSH1 (sequences homologous to AY866434) by real time PCR analysis of cDNA made from isolated RNA from the plants. Transgenic tomato plants suppressed for MSH1 are self pollinated and outcrossed to each parental line to obtain non-transgenic progeny, and each subsequent non-transgenic generation is self pollinated to produce tomato plants with enhanced yields, relative to their parental control plants.

Example 12. Transgenic Potatoes with Suppression of Plastidic MSH1 in the Presence of Mitochondrial-Targeted MSH1 Using the *Arabidopsis* AOX1 Mitochondrial Targeting Signal Transgenic potato plants are produced pCAMBIA2300//Arab PRO-Arab-AOX1-Potato-MSH1//Tomato MSH1 RNAi (FIG. 6.19) in Agrobacteria and using kanamycin as the selection system as described (De Block 1988 Theor Appl Genet 76:767-774). Said transgenic potato plants are screened for those that suppress endogenous potato MSH1 (sequences homologous to XM_006340821 at the NCBI) by real time PCR analysis of cDNA made from isolated RNA from the plants. Transgenic potato plants suppressed for MSH1 are self pollinated and outcrossed to each parental line to obtain non-transgenic progeny, and each subsequent non-transgenic generation is self pollinated and/or vegetatively propagated to produce potato plants with enhanced yields, relative to their parental control plants.

Those skilled in the art recognize there are many possible ways to cause suppression of plastidic MSH1 in the presence of mitochondrial-targeted MSH1. In one embodiment, a mutation can attenuate or create a null mutation in an endogenous MSH1 gene. This mutation is then complemented, transiently or stably, with a source of MSH1 functional in the mitochondria but not functional in the plastids. In one embodiment this can be accomplished by mutation of the FYE domain. In other embodiments, attachment of a signal peptide that targets MSH1 to mitochondria but not plastids can be used. In certain embodiments the endogenous MSH1 gene is suppressed by RNAi and a synthetic transgene with limited homology to the RNAi construct expresses mitochondrial targeted MSH1 without being subjected to RNAi suppression. Those skilled in the art will recognize many different mitochondrial targeting proteins are known for targeting MSH1 to the mitochondria.

The embodiments were chosen and described in order to best explain the principles of the disclosure and its practical application to thereby enable others skilled in the art to best utilize the disclosure in various embodiments and with various modifications as are suited to the particular use contemplated. As various modifications could be made in the constructions and methods herein described and illustrated without departing from the scope of the disclosure, it is intended that all matter contained in the foregoing description or shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

Sample claims of various inventive aspects of the disclosure, not to be considered as exhaustive or limiting, all of which are fully described so as to satisfy the written description, enablement, and best mode requirement of the Patent Laws, are as follows:

What is claimed is:

1. A plant or plant cell comprising a mutation in a MutS Homolog 1 (MSH1) gene polynucleotide sequence encoding the FYE amino acid sequence of the DNA binding domain 1 of the MSH1 polypeptide, wherein the mutation encodes the amino acid sequence FYZ in the DNA binding domain 1 wherein Z is any amino acid other than E, wherein such mutation is not present in control plants of the same species, wherein MSH1 function is suppressed in plastids of the plant or plant cell, and wherein MSH1 function is maintained in mitochondria of the plant or plant cell.

2. The plant or plant cell of claim 1, wherein the mutation in the polynucleotide sequence that encodes the FYE amino acid sequence of the DNA binding domain 1 of MSH1 is a mutation that encodes the amino acid sequence FYA in the DNA binding domain.

3. The plant or plant cell of claim 1, wherein the plant or plant cell is a *Capsella rubella, Ricinus communis, Populus trichocarpa, Theobroma cacao, Citrus sinensis, Citrus clementine, Vitis vinifera, Prunus persica, Fragaria vesca* subsp. *Vesca, Solanum tuberosum, Cucumis sativus, Solanum lycopersicum, Cicer arietinum, Glycine max, Phaseolus vulgaris, Oryza sativa Japonica* Group, *Oryza sativa* Indica Group, *Oryza brachyantha, Setaria italica, Medicago truncatula, Zea mays, Cucumis sativus, Hordeum vulgare* subsp. *Vulgare, Sorghum bicolor, Aegilops tauschii,* or *Triticum aestivum* plant or plant cell.

* * * * *